(12) United States Patent
Kotb et al.

(10) Patent No.: US 6,696,279 B1
(45) Date of Patent: Feb. 24, 2004

(54) PURIFIED AND ISOLATED MAT II β SUBUNIT NUCLEIC ACIDS AND POLYPEPTIDES AND THERAPEUTIC AND SCREENING METHODS USING SAME

(75) Inventors: Malak Kotb, Memphis, TN (US); H. Leighton LeGros, Jr., Memphis, TN (US); Arthur M. Geller, Memphis, TN (US)

(73) Assignee: University of Tennessee Research Foundation, Memphis, TN (US)

( * ) Notice: Subject to any disclaimer, the term of this patent is extended or adjusted under 35 U.S.C. 154(b) by 80 days.

(21) Appl. No.: 09/609,133

(22) Filed: Jun. 30, 2000

Related U.S. Application Data
(60) Provisional application No. 60/142,020, filed on Jul. 1, 1999.

(51) Int. Cl.[7] .............................. C12N 9/10; C12N 1/21; C12N 15/52; C12Q 1/68; C07M 21/04
(52) U.S. Cl. ..................... 435/193; 435/6; 435/252.3; 435/320.1; 435/325; 435/410; 536/23.2
(58) Field of Search ............................. 435/193, 252.3, 435/320.1, 325, 410, 6; 536/23.2

(56) References Cited

PUBLICATIONS

LeGros et al. (Jan. 28, 2000) J. Biol. Chem., vol. 275 (4), 2359–2366.*

Wozney (1991) in Methods in Enzymology, vol. 182, pp. 738–751.

De La Rosa et al., "Chromosomal Localization and Catalytic Properties of the Recombinant a Subunit of Human Lymphocyte Methionine Adenosyltransferase," J. Biol. Chem., vol. 270 (No. 37), p. 21860–21868 (1995).

Dwivedi et al., "S–Adenosylmethionine Synthetase is Overexpressed in murine Neuroblastoma Cells Resistant to Nucleoside Analogue Inhbitors of S–Adenosylhomocysteine Hydrolase: A Novel Mechanism of Drug Resistance," Canc. Res., p. 1852–1856, (Apr. 15, 1999).

Halim et al., "Expression and Functional Interaction of the Catalytic and Regulatory Subunits of Human Methionine Adenosyltransferase in Mammalian Cells," J. Biol. Chem., p. 29720–29725, (1999).

Legros, Jr. et al., "Differential Regulation of Methionine Adenosylatransferase in Superantigen and Mitogen Stimulated Human T Lymphocytes," J. Biol. Chem., vol. 272 (No. 25), p. 16040–16047, (Jun. 20, 1997).

PCT International Search Report for International Application No. PCT/US00/18269 dated Oct. 13, 2000.

* cited by examiner

*Primary Examiner*—Elizabeth Slobodyansky
(74) *Attorney, Agent, or Firm*—Jenkins, Wilson & Taylor, P.A.

(57) ABSTRACT

MAT II β subunit proteins and cDNAs encoding the same. Recombinant host cells, recombinant nucleic acids and recombinant proteins are also disclosed, along with methods of producing each. Isolated and purified antibodies to MAT II β subunit homologs, and methods of producing the same, are also disclosed. MAT II β subunit gene products are characterized as having activity in modulating the biological activity of MAT II. Thus, therapeutic methods involving these activities are also disclosed.

19 Claims, 21 Drawing Sheets

MAT IIβ Protein Subunit Sequence cDNA

```
        -60 CGTCGATCCTGGGTTGGAGGAGGTGGGCGGCCGTGAGGCTGCGGCGTGAAGACGGCGGGC     -1

M  V  G  R  E  K  E  L  S  I  H  F  V  P  G  S  C  R  L  V  E  E  E  V  N  I  P  N  R  R  V  L  V     (33)
  (1) ATGGTGGGCGGGAGAAAGAACTGTCTATACACTTGTTCCCGGGAGCTGTCGGCTGGTGGAGGAAGAAGTTAACATCCCTAATAGGAGGGTTCTGGTT      99
   +1

T  G  A  T  G  L  L  G  R  A  V  H  K  E  F  Q  Q  N  N  W  H  A  V  G  C  G  F  R  R  A  R  P  K    (66)
 (34) ACTGGTGCCACTGGGCTTCTTGGCAGAGCTGTACACAAAGAATTTCAGCAGAATAATTGGCATGCAGTTGGCTGTGTTCAGAAGAGCAAGACCAAAA      198

F  E  Q  V  N  L  L  D  S  N  A  V  H  H  I  I  H  D  F  Q  P  H  V  I  V  H  C  A  A  E  R  R  P     (99)
 (67) TTTGAACAGGTTAATCTGTTGGATTCTAATGCAGTTCATCACATCATTCATGATTTTCAGCCCCATGTTATAGTACATTGTGCAGCAGAGAGACCA       297

D  V  V  E  N  Q  P  D  A  A  S  Q  L  N  V  D  A  S  G  N  L  A  K  E  A  A  V  G  A  F  L  I      (132)
(100) GATGTTGTAGAAAATCAGCCAGATGCTGCCTCTCAACTTAATGTGGATGCTTCTGGGAATTTAGCAAAGGAAGCAGCTGTGTTGGAGCATTTCTCATC      396

Y  I  S  S  D  Y  V  F  D  G  T  N  P  P  Y  R  E  E  D  I  P  A  P  L  N  L  Y  G  K  T  K  L  D    (165)
(133) TACATTAGCTCAGATTATGTATTTGATGGAACAAATCCACCTTACAGAGAAGACATACCAGCTCCCTAAATTTGTATGGCAAACAAAATTAGAT        495

G  E  K  A  V  L  E  N  N  L  G  A  V  L  R  I  P  I  L  Y  G  E  V  E  K  L  E  E  S  A  V  T      (198)
(166) GGAGAAAAGGCTGTCCTGGAGAACAATCTAGGAGCTGTGTTTGAGGATTCCTATTCGTATGGGGAAGTTGAAAAGCTCGAAGAAAGTGCTGTGACT      594

V  M  F  D  K  V  Q  F  S  N  K  S  A  N  M  D  H  W  Q  Q  R  F  P  T  H  V  K  D  V  A  T  V  C    (231)
(199) GTTATGTTTGATAAAGTGCAGTTCAGCAACAAGTCAGCAAACATGGATCACTGGCAGCAGAGGTTCCCCACACATGTCAAAGATGTGGCCACTGTGC      693

R  Q  L  A  E  K  R  M  L  D  P  S  I  K  G  T  F  H  W  S  G  N  E  Q  M  T  K  Y  E  M  A  C  A    (264)
(232) CGGCAGCTAGCAGAGAAGAGAATGCTGGATCCATCAATTAAGGAACCTTTCACTGGTCTGGCAATGAACAGATGACTAAGTATGAAATGGCATGTGCA      792

I  A  D  A  F  N  L  P  S  S  H  L  R  P  I  T  D  S  P  V  L  G  A  Q  R  P  R  N  A  Q  L  D  C    (297)
(265) ATTGCAGATGCCTTCAACCTCCCCAGCAGTCACTTAAGACCTATTACTGACAGCCCTGTCCTAGGAGCACAACGTCCGAGAAATGCTCAGCTTGACTGC      891

S  K  L  E  T  L  G  I  G  Q  R  T  P  F  R  I  G  I  K  E  S  L  W  P  F  L  I  D  K  R  W  R  Q    (330)
(298) TCCAAATTGGAGACCTTGGGCATTGGCCAACAGACACCATTTCGAATTGGAATCAAAGAATCACTTTGGCCTTTCCTCATTGACAAGAGATGGAGACAA      990

T  V  F  H  Ter                                                                                      (334)
(331) ACGGTCTTTCATTAGTCTATTGTGTTGGGTTCTCTTTTTTTTTTAAATGAAAAGTATAGTATGTGGCACTTTTAAAGAACAAAGGAAATAGTTTTGTAT     1089
 991  GAGTACTTTAATTGTGACTCTTAGGATCTTTCAGTAAATGATGCTCTTGCACTAGTAAATTGTCTAGTGAAATTGTCATAAGGCAGTCATGCCCTGTTTG     1089
1090  CAGTAATTTTCTTTTTATCATTTCAGATGAAATTTGTTGTCCTGGCTAAACTTGGAGTTTGAGTAGTAAATTATGATCCTTAAATATTGAGAGTCAGATGAAGC     1188
1189  AGACCTGCTCTGTAGACTTTTGAAATAGTAAAAATCATTGGTACATTATTGAACTTGCTTGCCTGAGCTCAGATCAAAATGTTGAAGAAGAACTTATTTTGCAAGTT     1287
1288  AATTGTGTGAAATTTTATGCTTGAGATATTTCAACATGTTATGTATATTGGAACATGTCTACACGTTGTGTACAGTTGAACTTCTACACGTTGAACTTTATGGGAGCAC     1386
1387  ACGTACAGTTTTTATGCTTGAGATATTTTTTTTTCTAGCAAACATTGAATGCAAACATTATTAATATAAATATATAAATAACTGTCCTTTCATCCCAT     1485
1486  TTGAAAGAGCGTGTGTACATGTATATTTCATATGTGGTTATACTCATAATAATGGGCCTTGTAAGCCTTTTCACCATTCATGAATAATAAATATGTACTGCT     1584
1585  GTTGCCGCTAAGTGATATTTCATATGTGGTTATACTCATAATAATGGGCCTTGTAAGCCTTTTCACCATTCATGAATAATAAATATGTACTGCT     1683
1684  GGCATGT(A)18+                                                                                          1783
```
▼ polyadenylation signal

FIG. 1

MAT II β Protein Subunit Sequence cDNA

```
       -60 CGTCGATCCTGGGTTGAGGAGGTGGCGCCGCTGAGGCTGCGGCGTGAAGACGGCGGGC            -1
  (1)      M  V  G  R  E  K  E  I  S  I  H  F  V  P  G  S  C  R  L  V  E  E  E  V  N  I  P  N  R  R  V  L  V    (33)
  +1       ATGGTGGGCCGGGAGAAAGAAATCTCTATACACTTTGTTCCCGGGAGCTGTCGGCTGTTGGAGGAGAAGTTAACATCCCTAATAGGAGGGTTCTGGTT     99

(34)      T  G  A  T  G  L  L  G  R  A  V  H  K  E  F  Q  N  N  W  H  A  V  G  C  G  F  R  R  A  R  P  K        (66)
  100      ACTGGTGCCACTGGCTTCTTGGCAGAGCTGTACACAAAGAATTTCAGCAGAATAATTGGCATGCAGTTGGCTGTGTTCAGAGAGCAAGACCAAAA          198

(67)      F  E  Q  V  N  L  L  D  S  N  A  V  H  H  I  I  H  D  F  Q  P  H  V  I  V  H  C  A  A  E  R  R  P      (99)
  199      TTTGAACAGGTTAATCTGTTGGATTCTAATGCAGTTCATCACATCATTCATGATTTTCAGCCCCATGTTATAGTACATTGTGCAGCAGAGAAGACCA         297

(100)      D  V  V  E  N  Q  P  D  A  A  S  Q  L  N  V  D  A  S  G  N  L  A  K  E  A  A  V  G  A  F  L  I        (132)
  298      GATGTTGTAGAAAATCAGCCAGATGCTGCTTCTCAACTTAATGTGGATGCTTCTGGAATTTAGCAAAGGAAGCAGCTGCTGTTGGAGCATTTCTCATC         396

(133)      Y  I  S  S  D  Y  V  F  D  G  T  N  P  P  Y  R  E  E  D  I  P  A  P  L  N  L  Y  G  K  T  K  L  D      (165)
  397      TACATTAGCTCAGATTATGTATTTGATGGAACAAATCCACCTTACAGAGAGGAAGACATACCAGCTCCCTAAATTGTATGGCAAAACAAAATTAGAT         495

(166)      G  E  K  A  V  L  E  N  N  L  G  A  A  V  L  R  I  P  I  L  Y  G  E  V  E  K  L  E  E  S  A  V  T      (198)
  496      GGAGAAAAGGCTGTCCTGGAGAACAATCTAGGAGCTGCTGTGTTTGAGATTCCTATTCTGTATGGGGAAGTTGAAAAGCTCGAAGAAAGTGCTGTGACT       594

(199)      V  M  F  D  K  V  Q  F  S  N  K  S  A  N  M  D  H  W  Q  Q  R  F  P  T  H  V  K  D  V  A  T  V  C      (231)
  595      GTTATGTTTGATAAAGTGCAGTTCAGCAACAAGTCAGCAAACATGGATCACTGGCAGCAGAGATTCCCCACACATGTCAAAGATGTGGCCACTGTGTGC      693

(232)      R  Q  L  A  E  K  R  M  L  D  P  S  I  K  G  T  F  H  W  S  G  N  E  Q  M  T  K  Y  E  M  A  C  A      (264)
  694      CGGCAGCTAGCAGAGAAGAGAATGCTGGATCCATCAATTAAGGAAACCTTCACTGGTCTGGCAATGAACAGATGACTAAGTATGAAATGGCATGTGCA       792

(265)      I  A  D  A  F  N  L  P  S  S  H  L  R  P  I  T  D  S  P  V  L  G  A  Q  R  P  R  N  A  Q  L  D  C      (297)
  793      ATTGCAGATGCCTTCAACCTCCCCAGCAGTCACTTAAGACCTATTACTGACAGCCCTGTCCTAGGAGCACAACGTCCGAGAAATGCTCAGCTTGACTGC      891

(298)      S  K  L  E  T  L  G  I  G  Q  R  T  P  F  F  R  I  G  I  K  E  S  L  W  P  F  L  I  D  K  R  W  R  Q   (330)
  892      TCCAAATTGGAGACCTTGGGCATTGGCCAACGAACACCATTTTTCCGAATTGGAATCAAAGAATCACTTTGGCCTTTCCTCATTGACAAGAGATGGAGACAA   990

(334)
(331)      T  V  F  H  Ter
  991      ACGGTCTTTCATTAGTCTATTTGTGTTGGGTTCTTTTTTTTTAAATGAAAAGTATAGTTATGTGGCACTTTTTAAAGAACAAAGGAAATAGTTTTGTAT      1089
 1090      GAGTACTTTAATTGTGACTCTTCAGGTAAATGATGCTCTTGCACTAGTGAATTGTCTAAGAAACTAAAGGCAGTCATGCCCTGTTTG
 1189      CAGTAATTTTCTTTTATCATTTGTTTGTCCTGGCTAAACTGGAGTTTGAGTAGTATAGTAAATTATGATCCTTAAATATTTGAGAGTGCAGGATGAAGC
 1288      AGACCTGCTGTAGACTTTTCAGATGAAATTCATTGGTGTACATTTCAGCTCAGATCAAAATGTTGAAGAAAGGAACTTATTTTTGCAAGTT
 1387      AATTGTGTGAAATAGTATAAAATCATTGTGTACATGTTATGTTATATTGAACTTCTACACAGTTCTCGCTTTTATGCAGTTATGGGGAGCAC
 1486      ACGTACAGTTTTATGCTTGAGATATTTCTAGGCAAACATTGAATGCAAACGTGTATTTTTAATAATAAATATAACTGTCCTTTCATCCCAT
 1585      TTGAAAGAGCGTGTGATATTTCATATGTGGTTATACTCATAATAATAAATGGCCTTGTAAGCCTTTCACCATTCATGAATAATAAATAATATGTACTGCT
 1684      GTTGCCCGCTAAGTGATATTTCATATGTGGTTATACTCATAATAATAAATGGCCTTGTAAGCCTTTCACCATTCATGAATAATAAATAATATGTACTGCT
 1783      GGCATGT (A) 18+
                                                                                    polyadenylation signal
```

FIG. 2

MAT II β Protein Subunit Sequence cDNA

```
                -60 CGTCGATCCTGGGTTGGAGGAGTGGCGGCCGCTGAGGCTGCGGCGTGAAGACGGCGGGC    -1

(1)    M  V  G  R  E  K  E  L  S  I  H  F  V  P  G  S  C  R  L  V  E  E  V  N  I  P  N  R  R  V  I  V   (33)
  +1    ATGGTGGGCCGGGAGAAAGAACTGTCTATACACTTTGTTCCCGGGAGCTGTGCGGCTGGTGGAGGAAGTTAACATCCCTAATAGGAGGGTTATCGTT    99

(34)    T  G  A  T  G  L  L  G  R  A  V  H  K  E  F  Q  N  N  W  H  A  V  G  C  G  F  R  R  A  R  P  K   (66)
 100    ACTGGTGCCACTGGGCTTCTTGGCAGAGCTGTACACAAAGAATTTCAGCAGAATAATTGGCATGCAGTTGGCTGTGGTTTCAGAAGAGCAAGACCAAAA    198

(67)    F  E  Q  V  N  L  L  D  S  N  A  V  H  I  I  H  D  F  Q  P  H  V  I  V  H  C  A  A  E  R  R  P   (99)
 199    TTTGAACAGGTTAATCTGTTGGATTCTAATGCAGTTCATCACATCATTCATGATTTTCAGCCCCATGTTATAGTACATTGTGCAGCAGAGAGAAGACCA    297

(100)    D  V  V  E  N  Q  P  D  A  A  S  Q  L  N  V  D  A  S  G  N  L  A  K  E  A  A  A  V  G  A  F  L  I  (132)
 298    GATGTTGTAGAAAATCAGCCAGATGCTGCCTCTCAACTTAATGTGGATGCTTCTGGGAATTTAGCAAAGGAAGCAGCTGCTGTTGGAGCATTTCTCATC    396

(133)    Y  I  S  S  D  Y  V  F  D  G  T  N  P  P  Y  R  E  E  D  I  P  A  P  L  N  L  Y  G  K  T  K  L  D  (165)
 397    TACATTAGCTCAGATTATGTATTTGATGGAACAAATCCACCTTACAGAGAAGACATACCAGCTCCCTAAATTTGTATGCAAAACAAAATTGAT    495

(166)    G  E  K  A  V  L  E  N  N  L  G  A  A  V  L  R  I  P  I  L  Y  G  E  V  E  K  L  E  E  S  A  V  T  (198)
 496    GGAGAAAAGGCTGTCCTGGAGAACAATCTAGGAGCTGCTGTTTTGAGGATTCCTATTCTGTATGGGGAAGTTGAAAAGCTCGAAGAAGTGCTGTGACT    594

(199)    V  M  F  D  K  V  Q  F  S  N  K  S  A  N  M  D  H  W  Q  Q  R  F  P  T  H  V  K  D  V  A  T  V  C  (231)
 595    GTTATGTTTGATAAAGTGCAGTTCAGCAACAAGAGTGCAAACATGGATCACTGGCAGCAGAGAGTTCCCACACATGTCAAAGATGTGGCCACTGTGTGC    693

(232)    R  Q  L  A  E  K  R  M  L  D  P  S  I  K  G  T  F  H  W  S  G  N  E  Q  M  T  K  Y  E  M  A  C  A  (264)
 694    CGGCAGCTAGCAGAGAAGAGAATGCTGGATCCATCAATTAAGGGAACCTTCACTGGTCTGGCAATGAACAGATGACTAAGTATGAAATGGCATGTGCA    792

(265)    I  A  D  A  F  N  L  P  S  S  H  L  R  P  I  T  D  S  P  V  L  G  A  Q  R  P  R  N  A  Q  L  D  C  (297)
 793    ATTGCAGATGCCTTCAACCTCCCCAGCAGTCACTTAAGACCTATTACTGACAGCCCTGTCCTGGAGGCACAACGTCCGAGAAATGCTCAGTTGACTGC    891

(298)    S  K  L  E  T  L  G  I  G  Q  R  T  P  F  R  I  G  I  K  E  S  L  W  P  F  L  I  D  K  R  W  R  Q  (330)
 892    TCCAAATTGGAGACCTTGGGCATTGGCCAACGAACACCATTTGCCAACGAACACCATTTGGCCTTTCCTCATTGACAAGAGATGGAGACAA    990

(331)    T  V  F  H  Ter                                                                                   (334)
 991    ACGGTCTTTCATTAGTCTATTGTCTTTTTGTGGGTCTTCTTTTTTTTTAAATGAAAAGTATAGTAGTGAAAAGTATCCCTGTTTG    1089
1090    GAGTACTTGACTCTTAATGTGACTCTTAGGATCTTTCAGGTAAATGATGCTCTTGCACTTGTCTAAAGAACTAAAGGCAGTCATGCCCTGTTTG
1189    CAGTAATTTTCTTTTATCATTTGTTTGTCCTGGCTAAACTTGGAGTTGAATGTAAATTATGATCCTTAAATATTGAGTCAGGATGAAGC
1288    AGACCTGCTGTAGACTTTTCAGATGAATAAATCATTGTTCATTCTCGAAACATGTTCCTTGCCTGACTCAGATCAAAATGTTTGAAGAAGAACTTATTTTTGCAAGTT
1387    AATTGTGTGAAATAGTATAAAAATCATTGGTATGACATTGTTATATGTATATTGAACTTCTACACGTTCAGATCAAAATGTTGAAGAAGAACTTTATTTTGCAAGTT
1486    ACGTACAGTTTTATGCTGTACATGTATTTCAACATGTTCAAACATGTGATCCCTCGTCCTGTTTGATGCTGCTTTATGGGAGCAC
1585    TTGAAAGAGCGTGTACATGTATTTTTTTTCTAGGCAAACATTGAATGCAAACGTGTATTTTTTAATATAAATATATAACTGTCCTTTCATCCAT
1684    GTTGCCGCTAAGTAGTGATATATTTCATATGTGTTATACTCATATAATATAATGGGCCTTGTAAGCCTTTTCACCATTCATGAATAATA̲A̲T̲A̲A̲ATGTACTGCT
1783    GGCATGT(A) 18+                                                                polyadenylation signal
```

FIG. 3

MAT II β Protein Subunit Sequence cDNA

```
         -60 CGTCGATCCTGGGTTGGAGGAGGTGGCGGCCGCTGAGCCTGCGGCGTGAAGACGGCGGGC        -1

M  V  G  R  E  K  E  L  S  I  H  F  V  P  G  S  C  R  L  V  E  E  E  V  N  I  P  N  R  R  V  L  V      (33)
 (1) ATGGTGGGCCGGGAGAAAGAACTGTCTATACACTTTGTTCCCGGGAGCTGTCGCCTGGTGGAGGAGGAAGTTAACATCCCTAATAGAGGGGTTCTGGTT      99
 +1

T  G  A  T  G  L  L  G  R  A  V  H  K  E  F  Q  Q  N  N  W  H  A  V  G  C  G  F  R  R  A  R  P  K      (66)
(34) ACTGGTGCCACTGGGCTTCTTGGCAGAGCTGTACACAAAGAATTTCAGCAGAATAATTGGCATGCAGTTGGCTGTGTTTCAGAAGAGCAAGACCAAAA     198

F  E  Q  V  N  L  L  D  S  N  A  V  H  H  I  I  H  D  F  Q  P  H  V  I  V  H  C  A  A  E  R  R  P      (99)
(67) TTTGAACAGTTAATCTGTTGGATTCAATGCAGTTCATCACATCATTCATGATTTTCAGCCCCATGTTATAGTTCATTGTGCAGCAGAGAGAAGACCA     297

D  V  V  E  N  Q  P  D  A  A  S  Q  L  N  V  D  A  S  G  N  L  A  K  E  A  A  A  V  G  A  F  L  I     (132)
(100) GATGTTGTAGAAAATCAGCCAGATGCTGCCTCTCAACTTAATGTGGATGCTTCTGGGAATTTAGCAAAGGAAGCAGCTGCTGTTGGAGCATTTCTCATC     396

Y  I  S  S  D  Y  V  F  D  G  T  N  P  P  Y  R  E  E  D  I  P  A  P  L  N  L  Y  G  K  T  K  L  D     (165)
(133) TACATTAGCTCAGATTATGTATTTGATGGAACAAATCCACCTTACAGAGAGGAAGACATACCAGCTCCCTAAATTTGTATGGCAAAACAAAATTAGAT     495

G  E  K  A  V  L  E  N  N  I  G  A  A  V  L  R  I  P  I  I  Y  G  E  V  E  K  L  E  E  S  A  V  T     (198)
(166) GGAGAAAAGGCTGTCCTGGAAAACATATCGGAGCTGCTGTTTGAGGATTCCTATTATCTATGGGAAGTTGAAAAGCTCGAAGAAAGTGCTGTGACT     594

V  M  F  D  K  V  Q  F  S  N  K  S  A  N  M  D  H  W  Q  Q  R  F  P  T  H  V  K  D  V  A  T  V  C     (231)
(199) GTTATGTTTGATAAAGTCCAGTTCAGCAACAAGTCAGCAACATGGATCACTGGCAGAGAGGTTCCCCACACATGTCAAAGATGTGGCCACTGTGTGC     693

R  Q  L  A  E  K  R  M  L  D  P  S  I  K  G  T  F  H  W  S  G  N  E  Q  M  T  K  Y  E  M  A  C  A     (264)
(232) CGGCAGCTAGCAGAGAAGAGAATGCTGGATCCATCCATCAAGGGAACCTTTCACTGGTCTGGCAATGAACAGATGACTAAGTACGAAATGGCATGTGCA     792

I  A  D  A  F  N  L  P  S  S  H  L  R  P  I  T  D  S  P  V  L  G  A  Q  R  P  R  N  A  Q  L  D  C     (297)
(265) ATTGCAGATGCCTTCAACCTCCCCAGCAGTCACTTAAGACCTATTACTGACAGCCCTGTCCTAGGAGCCCAACGTCCGAGAAATGCTCAGCTTGACTGC     891

S  K  L  E  T  L  G  I  Q  R  T  P  F  R  I  G  I  K  E  S  L  W  P  F  L  I  D  K  R  W  R  Q       (330)
(298) TCCAAATTGGAGACCCTTGGGCATTGGCCAACGAACACCATTTCGAATTGGAATCAAAGAATCACTTTGGCCTTTCCTCATTGACAAGAGATGGAGACAA     990

T  V  F  H  Ter                                                                                        (334)
(331) ACGGTCTTTCATTAGTCTATTTGTGTTGGGTTCTCTTTTTTTTTAAATGAAAAGTATAGTATGTGGCACTTTTAAAGAACAAAGGAATAGTTTTGTAT    1089
 991 GAGTACTTTAATTGTGACTCTTAGGATCTTTCAGGTAAATGATGCTCTTCAGTGAGTAAATTGTCTAAAGAAACTAAAGGCAGTCATGCCCTGTTTG
1090 CAGTAATTTTCTTTTTATCATTTGTTTCTTTGTTGTCCTGCTCAAACTTGGAGTTTGAGTATAGTAAATTGATCCTTAAATATTTGAGAGTCAGGATGAAGC
1189 AGACCTGCTGTAGAACTTTTCAGATGGAAATTGTTCATTCTGCGTACCTCGTATCTCGTAACCTCCATATTTTCAGGATTTTGAAGCTGTGACCTTTCATGTTGATTATTTA
1288 AATTGTGTGAAATAGTATAAAAATCATTGGTGTACATTATTTGCCTTGCCTGAGTCAGATCAAAATGTTTGAAGAAAGGAACTTTATTTTTGCAAGTT
1387 ACGTACAGTTTTTATGCTTGAGATATTTCAAGCTGTATGTATATTGGAACTTCTACACGTTGATGCCTGTTATACAGTTTATGGAGCAC
1486 TTGAAAGAGCGTGTACATGTATTTTTCTAGGCAAACATTGAATGCAAACGTGTATTTTTTTAATTATAAATATAACTGTCTTTCATCCAT
1585 GTTGCCGCTAAGTGCATGATATTTCATATGTGTGTTATACTTCATAATAATGGGCCTTGTAAGCCTTTTCACCATTCATGAATAATAAATATGTACTGCT
1684 GGCATGT(A)18+
1783
                                                ↑
                                            polyadenylation signal
```

FIGURE 4

MAT II β Protein Subunit Sequence cDNA

```
                -60 CGTCGATCCTGGGTTGGAGGAGGTGGCGGCCTGCGGCTGAAGACGGCGGGC    -1

M  V  G  R  E  K  E  L  S  I  H  F  V  P  G  S  C  R  L  V  E  E  V  N  I  P  N  R  R  V  L  V   (33)
 (1)  ATGGTGGGCGGGAGAAAGAACTGTCTATACACTTTGTTCCCGGGAGCTGTCGGCTGTGGAGGAGAAGTAACATCCTAATAGGAGGGTTCTGTT    99
 +1

T  G  A  T  G  L  L  L  G  R  A  V  H  K  E  F  Q  Q  N  N  W  H  A  V  G  C  G  F  R  R  A  P  K   (66)
 (34) ACTGGGTGCCACTGGGCTTCTTGGCAGAGCTGTACACAAAGAATTTCAGCAGAATAATTGGCATGCAGTTGGCTGTGTTCAGAAGAGCAAGACCAAAA   198

F  E  Q  V  N  L  L  D  S  N  A  V  H  H  I  I  H  D  F  Q  P  H  V  I  V  H  C  A  A  E  R  R  P   (99)
 (67) TTTGAACAGGTTAATCTGTTGGATTCTAATGCAGTTCATCACATCATTCATGATTTTCAGCCCCATGTTATAGTACATTGTGCAGCAGAGAGACCA    297

D  V  V  E  N  Q  P  D  A  A  S  Q  L  N  V  D  A  S  G  N  L  A  K  E  A  A  V  G  A  F  L  I   (132)
(100) GATGTTGTAGAAAATCAGCCAGATGCTGCCTCTCAACTTAATGTGGATGCTTCTGGGAATTTAGCAAAGGAAGCAGCTGTGTTGGAGCATTTCTCATC    396

Y  I  S  S  D  Y  V  F  D  G  T  N  P  P  Y  R  E  E  D  I  P  A  P  L  N  L  Y  G  K  T  K  L  D   (165)
(133) TACATTAGCTCAGATTATGTATTTGATGGAACAAATCCACCTTACAGAGAGGAAGACATACCAGCTCCCCTAAATTTGTATGGCAAAACAAAATTAGAT   495

G  E  K  A  V  L  E  N  N  L  G  A  A  V  L  R  I  P  I  L  Y  G  E  V  E  K  L  E  E  S  A  V  T   (198)
(166) GGAGAAAAGGCTGTCCTGGAGAACAATCTAGGAGCTGCTGTTTTGAGGATTCCTATTCTGTATGGGAAGTTGAAAAGCTCGAAGAAAGTGCTGTGACT    594

V  M  F  D  K  V  Q  F  S  N  K  S  A  N  M  D  H  W  Q  Q  R  F  P  T  H  V  K  D  V  A  T  V  C   (231)
(199) GTTATGTTTGATAAAGTGCAGTTCAGCAACAAGTCAGCAAACATGGATCACTGGCAGCAGAGAGTTCCCACACATGTCAAAGATGTGGCCACTGTGTGC    693

R  Q  L  A  E  K  R  M  L  D  P  S  I  K  G  T  F  H  W  S  G  N  E  Q  M  T  K  Y  E  M  A  C  A   (264)
(232) CGGCAGCTAGCAGAGAAGAGAATGCTGGATCCATCAATTAAGGGAACCTTTCACTGGTCTGGCAATGAACAGATGACTAAGTATGAAATGGCATGTGCA   792

I  A  D  A  F  N  I  P  S  S  H  L  R  P  I  T  D  S  P  V  L  G  A  Q  R  P  R  N  A  Q  L  D  C   (297)
(265) ATTGCAGATGCCTTCAACATCCCCAGCAGTCACTTAAGACCTATTACTGACAGCCCTGTCCTAGGAGCACAACGTCCGAGAAATGCTCAGCTTGACTGC    891

S  K  L  E  T  L  G  I  G  Q  R  T  P  F  R  I  G  I  K  E  S  L  W  P  F  L  I  D  K  R  W  R  Q   (330)
(298) TCCAAATTGGAGACCTTGGGCATTGGCCAACGAACCACCATTTGAATTGAAATCAAAGAATCACTTGGCCTTTCCTCATTGACAAGAGATGGAGACAA    990

T  V  F  H Ter                                                                                        (334)
(331) ACGGTCTTTCATTAGTCTATTGTGTTGGGTTCTTTTTTTTTTAAATGAAAAGTATAGTATGTGGCACTTTTAAAGAACAAAGGAAATAGTTTTGTAT    1089
1090  GAGTACTTTAATTGTGACTCTTGACTCTTCAGTGAATCTTTCAGTAAATGATGCTCTTGCACTAGTGAAATTGTCTAAAGAACTAAAGGCATGCCCTGTTTG
1189  CAGTAATTTTCTTTCATTTTATCATTTGTTTGTCCTGGCTAAACTTGGAGTTGAGTATAAATTATGATCCTTAAATATTGAGAGTCAGGATGAAGC
1288  AGACCTGCTGTAGACTTTTCAGATGAAATTGTCATCTCGTAACCTCCATATTTTCGAGCTGTTGACCTTTCATGTTGATTATTTTA
1387  AATTGTGTGAAATAGTATAAAATCATTGGTGTACAATGTTATGTATATTCAACATGTTATCAGATCAAAATGTTGAAGAAAGAACTTATTTGCAAGTT
1486  ACGTACAGTTTTATGCTTGAGATATTTCAACATGTTATGTATATTCTACGCTTGGAACTTCTACACGTTATTTTTTAATATAACTGTCCTTTTCATCCCAT
1585  TTGAAAGAGCGTGTGTACATGTATTTTTTTCTAGGCAAACATTGAATGCAAACATGTAATTTTTAATATAATATAAACTGTCCTTTTCATCCCAT
1684  GTTGCCGCTAAGTGATATTTCATATGTGTGTTATACTCATAATATGGGCCTTGTAAGCCTTTCACCATTCATGAATAATAATA<u>TAT</u>ACTGCT
1783  GGCATGT(A)18+                                                                polyadenylation signal
```

FIG. 5

```
tttgcaaaag aaactccagg attcttgaca gaaagttgtt gggttttggt tttggttttg  60
ttaagtagtt agttctacca atagtttgca aatagaccca ggcttgactg gcaattaacc 120
atgaaacttc tcattgggta ttttcgagac tactacgggg aatcagctac cagcttact  180
gccatgtgga gaactgcacg agattccggg attggaatca aaatgctaat ttaaaaggtc 240
aagtgaagct gctcctcacg ttttggcgtg cctgcgctct ctgcaggcag aagcgaacaa 300
agacccagca agagaaggca gaggctaaga cccatcccgt atctgctctc ctgaaataat 360
tctggagtca tgcctgaaat gccagaggac atggagcagg taagaactag caattcaaga 420
aatgaagcat tctagagtaa gagatgcttt aaaagcattc cagtgaacgc tgctaaaac  480
cagaattgtt gtgtaaagaa aatagaaacg ggtgtcattc atttccttaa aacataacct 540
cgggacatgg aagaataagc caactttagt tactgacccg gagaaccagg ttatgaaggg 600
ctcagctaag tctcactagc tgacaataca gaattgcact tcatttacc attttaaatg  660
caattatgta tataaagttt ctacataaat aaggatttta tctgtagtgt gttcccttcc 720
agatgttctt tgtctttgta tgaattgaat ctgctaacat aacttttagt ttcaggctgc 780
tctctttaaa tgtatagact tagccaccac acgaagttgt atattgtcta tgttaagaat 840
ggcgtttgat tcgcatagac cctaccatca ttaaagaaaa tgattaaaaa ccatatccaa 900
acatatgccc ctagaactgt acccaacttt tacggggaaa gtatcaagtc agattttcaa 960
aagcagccaa gttaaattct ttctgttcct caagactagg ctgctctgag aatcagaatg 1020
ctaattgcat atgcttgccc ttaaacctgc ttcacgttga agaatgaaga attaattttc 1080
ttttctccca tagaaaggta agattacatc acgtgttgcg actagaaact taaaccgaa  1140
ttcccagtta agagaaaaag tagtaagatg atcttggctg ctcccccggc cctcttccg  1200
ccctcttctt tgttgtcccc tgattatgct tgtttagcgc tggggcagtc ctcaaggatt 1260
ccctaaataa agccaaactg atgaacagta atagcctgtg tttaaaaaaa aaaaaatcgg 1320
aacataagaa acctcaggct gtcttcgatt actgttctag agaaacttta tgtttacacg 1380
aataaggaaa tgagtttttg ttggggggttg aggaggaagg aaagtcatgg tgttctgacg 1440
tggaaaactt ctttaaaagg ctgcttagtc tttagtttga aaataaacca aaaaggttta 1500
ggagtcgggg aaaggcccta ggaaaatcca gacagtggtc acgtttgtgg acgacgttta 1560
gagcttgcta tcctgggcac acaagaaccc ttggactgtt cggtgcaaag ttggcaaatc 1620
ctacacggcc tgtgccaggg tttactttct gcatcaattt cacaggcgtc cagcctggct 1680
gaggactttt tgcggttttt aactggaagg gaaataagtc ggcatcagca cttaggctg  1740
cttaactttt aaaaggtggt agaacgccca gccttacacg ctgctgctta aattctcggt 1800
gctcaccaag gctgggctcg tgtggcccaa tcctgcaatc cccgaggcgg tgtttcttaa 1860
agagtgggct tgattctggt taaacccatt aagaagtcgg accccgggct cgtttcttgt 1920
tctgtaatta tgggtaaagt ccaaggatct gcgttttgaa gaggtaccta agtagttcat 1980
cttccttccc cctacaactt tttattttta attagttaaa aatagttta catttttgat  2040
atctcacaca caggtttttt ctttttttaa gcatcccagg aagacaaatg gctcagacgc 2100
caacccttt atttttattc cttgtctttt tctaaatctt tcaaaccccc cacctagagc  2160
tctagagatg tgtccattat gctctaccca cctccgcccc cgcccccatg actttaaaat 2220
gctttttatt ccacttttta tattgctcag tcgatcctca tgcactgcgc agtctgcaaa 2280
cttgaaactc aaggcgatcc acttcaatct ttcccgagt caagaaaaaa aggaaaaaaa  2340
gtagaataaa aagcactcaa ataaaatctc cgaaacaaaa cctgaattca ctgcctaagg 2400
tcagggcctt tcttttgtgt gtcgctttaa gcatcggcgc gtgggctggg ggcagaccgc 2460
gcgtacccgc cctctttctg gggcgtcggc ggagcgtggc caatcaacgg gcgcggctat 2520
ggcagcggaa gccggaagcg gcgagcgggg tcgttctggg cctagggag gcgggccgag 2580
ggcgtctgag ctgaggcccg cgtcgatcct gggttggagg aggtggcggc cgctgaggct 2640
gcggcgtgaa gacggcgggc                                            2660
```

FIG. 6 cDNA        -60 CGTCGATCCTGGGTTGAGGAGGAGGTGGCGGCCGCTGAGGCTGCGGCGTGAAGACGCGGGC    -1

(1)    M  V  G  R  E  K  E  L  S  I  H  F  V  P  G  S  C  R  L  V  E  E  E  V  N  I  P  N  R  R  V  L  V   (33)
+1     ATGGTGGGCCGGGAGAAAGAACTGTCTATACACTTTGTTCCCGGGAGCTGTCGGCTGTGGAGGAGAAGTTAACATCCCTAATAGGAGGGTTCTGGTT    99

(34)   T  G  A  T  G  L  L  G  R  A  V  H  K  E  F  Q  Q  N  N  W  H  A  V  G  C  G  F  R  R  A  R  P  K   (66)
100    ACTGGTGCCACTGGGCTTCTTGGCAGAGCTGTACACAAAGAATTCAGCAGAATAATTGGCATGCAGTTGGCTGTGTTCAGAGAGCAAGACCAAAA    198

(67)   F  E  Q  V  N  L  L  D  S  N  A  V  H  H  H  I  H  D  F  Q  P  H  V  I  V  H  C  A  A  E  R  R  P   (99)
199    TTTGAACAGGTTAATCTGTTGGATTCTAATGCAGTTCATCATCATATTCATGATTTTCAGCCCCATGTTATAGTACATTGTGCAGCAGAGAAGACCA    297

(100)  D  V  V  E  N  Q  P  D  A  A  S  Q  L  N  V  D  A  S  G  N  L  A  K  E  A  A  A  V  G  A  F  L  I   (132)
298    GATGTTGTAGAAAATCAGCCTGACGCTGCTTCTCAACTTAATGTGGATGCTTCTGGGAATTTAGCAAAGGAAGCAGCTGTTGGAGCATTTCTCATC    396

(133)  Y  I  S  S  D  Y  V  F  D  G  T  N  P  P  Y  R  E  E  D  I  P  A  P  L  N  L  Y  G  K  T  K  L  D   (165)
397    TACATTAGCTCAGATTATGTATTTGATGGAACAAATCCACCTTACAGAGAAGAAGACATACCAGCTCCCCTAAATTTGTATGGCAAAACAAAATTAGAT    495

(166)  G  E  K  A  V  L  E  N  N  L  G  A  A  V  L  R  I  P  I  L  Y  G  E  V  E  K  L  E  E  S  A  V  T   (198)
496    GGAGAAAAGGCTGTCCTGGAGAACAATCTAGGAGCTGCTGTTTTGAGGATTCCTATTCTGTATGGGGAAGTTGAAAAGCTCGAAGAAAGTGCTGTGACT    594

(199)  V  M  F  D  K  V  Q  F  S  N  K  S  A  N  M  D  H  W  Q  Q  R  F  P  T  H  V  K  D  V  A  T  V  C   (231)
595    GTTATGTTTGATAAAGTGCAGTTCAGCAACAAGTCAGCAACATGGATCACTGGCAGCAGAGGTTCCCCACACATGTCAAAGATGTGGCCACTGTGTGC    693

FIG. 8A (232) R  Q  L  A  E  K  R  M  |L  D  P  S  I  K  G  T  F  H  W  S  G  N  E  Q  M  T|  K  Y  E  M  A  C  A  (264)
694  CGGCAGCTAGCAGAGAAGAGAAATGCTGGATCCATCAATTAAGGGAACCTTTCACTGGTCTGGCAATGAACAGATGACTAAGTATGAAATGGCATGTGCA  792

(265) I  A  D  A  F  N  L  P  S  S  H  L  R  P  I  T  D  S  P  V  L  G  A  Q  R  P  R  N  A  Q  L  D  C  (297)
793  ATTGCAGATGCCTTCAACCTCCCCAGCAGTCACTTAGACCTATTACTGACAGCCCTGTCCTAGGAGCACAACGTCCAGAGAAATGCTCAGCTTGACTGC  891

(298) S  K  L  E  T  L  G  I  G  Q  R  T  P  F  F  R  I  G  I  K  E  S  L  W  P  F  L  I  D  K  R  W  R  Q  (330)
892  TCCAAATTGGAGACCCTTGGGCATTGGCCAACGAACACCATTTGAATTCGAATTCAAGAATCACTTTGGCCTTTCCTCATTGACAAGAGATGGAGACAA  990

(331) T  V  F  H  Ter  (334)
991  ACGGTCTTTCATTAGTCTATTCTGTGTTGGGTCTCTTTTTTTTTTAAAGAACAAAGGAAATAGTTTGTAT  1089
1090 GAGTACTTTAATTGTGACTCTTAGGATCTTGTTCCTCAGGTAAATGATGCTCTTGCACTAGTGAAATTGTCTAAAGAAACTAAAGGGCAGTCATGCCCTGTTTG
1189 CAGTAATTTTCTTTTTATCATTTGTTTGCTAAACTTGGAGTTTGAGTATAGTAAATTATGATCCTTAAATATTTGAGAGTCAGGATGAAGC
1288 AGACCTGCTGTAGAATAGTATGAAATCATTGGGTGTACATTATTTCCAGATTTTGCCTGAGCTCAGATCAAAATGTTTGAAGAAAGGAACTTTATTTTGCAAGTT
1387 AATTGTGTGAAATCATTTTTATGCTTGAGATATATATGCTTGAGATGTATTGCAACATGTTATGTATATTGAGCCTCCTGCTTTTATGCCTTTATGCAGTTTATGGGGAGCAC
1486 ACGTACAGTTTTATGCTGTGTACATGTATTTTTTCTAGGCAAACATTGAAATGCAAACGTGTATTTTTAATATAAACTGTCCTTTTCATCCAT
1585 TTGAAAGAGCGTGTGATAATTTCATATGTGTATTACATAATAAATGGGCCTTGTAAGCCTTGTAAGCCTTGTAATAATGTACTGCT
1684 GTTGCCGCTAAGTGCTAAGTGATATTTCATATGTGGTTATACTCCATAATAATGTGTAAGCCTTGTAAGCCTTGTAATAATGTACTGCT
1783 GGCATGT(A)₁₈₊ polyadenylation signal ▼

FIG. 8B

PURIFIED AND ISOLATED MAT II β SUBUNIT NUCLEIC ACIDS AND POLYPEPTIDES AND THERAPEUTIC AND SCREENING METHODS USING SAME

PRIORITY APPLICATION INFORMATION

This application is based on and claims priority to U.S. Provisional Application Ser. No. 60/142,020 filed Jul. 1, 1999, the entire contents of which are herein incorporated by reference.

GRANT STATEMENT

This work was supported by NIH grant GM-54892. Thus, the U.S. Government has certain rights in the invention.

TECHNICAL FIELD

The present invention relates generally to isolated and purified proteins and nucleic acids which modulate the biological activity of methionine adenosyltransferase II (MAT II). More particularly, the present invention relates to isolated and purified MAT II β subunit polypeptides and isolated and purified nucleic acids encoding the same.

| Table of Abbreviations | |
|---|---|
| BSA | bovine serum albumin |
| CDR(s) | complementarity determining region(s) |
| EST | expressed sequence tags |
| GC-MS | gas chromatography-Mass spectroscopy |
| HAT | cell culture media comprising hypoxanthine, aminopterin, and thymidine |
| HBSS | Hank's balanced salt solution |
| HPLC | high pressure liquid chromatography |
| KLH | keyhole limpet hemocyanin |
| MAT II | methionine adenosyltransferase II |
| myc | human oncogene used herein as molecular tag |
| ORF | open reading frame |
| PCR | polymerase chain reaction |
| PBMC | peripheral blood mononuclear cells. |
| RACE | rapid amplification of cDNA ends |
| RNAi | RNA interference assay |
| UTR | untranslated region |

BACKGROUND ART

Methionine adenosyltransferase (MAT; S-adenosyl-L-methionine (AdoMet) synthetase, EC 2.5.1.6) is an essential enzyme that catalyzes the synthesis of S-adenosylmethionine (AdoMet) from L-methionine (L-Met) and ATP (Cantoni, G. L. (1953) *J. Biol. Chem.* 204: 403–416; Mudd, S. H. (1973) The Adenosyltransferases, Third Edition Ed. The Enzymes, Group Transfer (Part A) (Bayer, P. D., Ed.), III). AdoMet is the major methyl group donor, participating in the methylation of proteins, DNA, RNA, phospholipids and other small molecules (reviewed in Finkelstein et al. (1975) *Biochem. Biophys. Res. Commun.* 66: 81–7; Tabor, C. W., and Tabor, H. (1984) *Adv. Enzymol. Relat. Areas Mol. Biol.* 56: 251–82; Mudd et al. (1995) Disorders of transsulfuration, 7th Ed. The Molecular and Metabolic Basis of Inherited Diseases (Scriver, C. R., Beaudet, A. L., Sly, W. S., and Valle, D., Eds.), McGraw-Hill Inc., New York). In addition, AdoMet is the ultimate source of the propylamine moiety used in polyamine biosynthesis, and it serves as co-factor for other key enzymes in the one-carbon metabolism pathway (Finkelstein et al. (1975) *Biochem. Biophys. Res. Commun.* 66: 81–7; Tabor, C. W., and Tabor, H. (1984) *Adv. Enzymol. Relat. Areas Mol. Biol.* 56: 251–82; Mudd et al. (1995) Disorders of transsulfuration, 7th Ed. The Molecular and Metabolic Basis of Inherited Diseases (Scriver, C. R., Beaudet, A. L., Sly, W. S., and Valle, D., Eds.), McGraw-Hill Inc., New York). MAT is present in all living species, including thermophilic archaebacteria, plants, yeast, and mammals (reviewed in Tabor, C. W., and Tabor, H. (1984) *Adv. Enzymol. Relat. Areas Mol. Biol.* 56: 251–82; Kotb, M., and Geller, A. M. (1993) *Pharmacol. Ther.* 59: 125–43; Chiang, et al. (1996) *FASEB J.* 10:471–80; Mato et al. (1997) *Pharmacol. Ther.* 73: 265–80). Interestingly, most species have more than one MAT isozyme (Kotb, M., and Geller, A. M. (1993) *Pharmacol. Ther.* 59: 125–43).

Mammalian MAT exists in multiple forms that differ in their physical and kinetic properties among distinct species and even among different tissues of the same species. In mammals there are three forms designated MAT I, II, and III that differ in their tissue distribution and kinetic properties (Hoffman, J. L. (1983) *Methods Enzymol.* 94, 223–8; Mato et al. (1994) *Adv. Exp. Med. Biol.* 368, 113–7; Okada et al. (1981) *Biochemistry* 20, 934–40; Kotb et al. (1997) *Trends Genet.* 13, 51–2). MAT I and III are referred to as the hepatic forms because their expression is confined to the liver. By contrast, MAT II is found in all mammalian tissues that have been examined to date, including erythrocytes, lymphocytes, brain, kidney, testis, and liver (Okada et al. (1981) *Biochemistry* 20, 934–40; Oden, K., and Clarke, S. (1983) *Biochemistry* 22, 2978–2986; Kotb, M., and Kredich, N. M. (1985) *J. Biol. Chem.* 260, 3923–30; Langkamp-Henken et al. (1994) *Biochim. Biophys. Acta* 1201, 397–404; Liau et al. (1979) *Cancer Res.* 39, 162–69; Sullivan, D. M., and Hoffman, J. L. (1983) *Biochemistry* 22, 1636–41; Mitsui et al. (1988) *J. Biol. Chem.* 263, 11211–16; Horikawa et al. (1990) *J. Biol. Chem.* 265, 13683–86).

MAT I is a tetramer and MAT III is a dimer of an identical catalytic subunit, α1, encoded by the MAT1A gene (Hoffman, J. L. (1983) *Methods Enzymol.* 94, 223–8; Horikawa, S., and Tsukada, K. (1991) *Biochem. Int.* 25, 81–90; Alvarez et al. (1993) *Biochem. J.* 293, 481–86; Sakata et al. (1993) *J. Biol. Chem.* 268, 13978–86; Ubagai et al. (1995) *J. Clin. Invest.* 96, 1943–47). On the other hand MAT II from leukemic T cells or from activated human lymphocytes is a hetero-oligmer consisting of α2 (53 kDa), α'2 (51 kDa) and β (38 kDa) subunits (Kotb, M., and Kredich, N. M. (1985) *J. Biol. Chem.* 260, 3923–30). The α2 and α'2 are the catalytic subunits while β appeared to have a regulatory function (De La Rosa et al. (1992) *J. Biol. Chem.* 267, 10699–704; De La Rosa et al. (1995) *J. Biol. Chem.* 270:21860–68; LeGros et al. (1997) *J. Biol. Chem.* 272, 16040–47; LeGros et al. (1999) Submitted). The α2 and α'2 subunits are immunologically crossreactive and essentially identical to each other, but quite different from the β subunit. The α2 subunit, which appears to be posttranslationally processed to yield α'2 (Kotb, M., and Kredich, N. M. (1985) *J. Biol. Chem.* 260, 3923–30), is encoded by the MAT2A gene which is homologous, but different from MAT1A gene (Kotb et al. (1997) *Trends Genet.* 13, 51–2; Horikawa, S., and Tsukada, K. (1991) *Biochem. Int.* 25, 81–90; De La Rosa et al. (1995) *J. Biol. Chem.* 270:21860–68).

The human MAT II from human lymphocytes has been analyzed to a certain extent (Kotb, M., and Kredich, N. M. (1985) *J. Biol. Chem.* 260: 3923–30; Kotb, M., and Kredich, N. M. (1990) *Biochim. Biophys. Acta* 1039(2): 253–60; De La Rosa et al. (1992) *J. Biol. Chem.* 267: 10699–704; De La Rosa et al. (1995) *J. Biol. Chem.* 270, 21860–8; LeGros et al. (1997) *J. Biol. Chem.* 272, 16040–7), and it has been shown that the form present in activated lymphocytes consists of distinct subunits (Kotb, M., and Kredich, N. M. (1985) J. Biol. Chem. 260, 3923–30; De La Rosa et al. (1992) J. Biol. Chem. 267, 10699–704). The catalytic MAT II α2 subunit, which is encoded by the MAT2A gene, was cloned and characterized and found to be homologous, but different from the catalytic α1 subunit of the liver MAT I/III isozyme (Horikawa, S., and Tsukada, K. (1991) Biochem. Int. 25, 81–90; Alvarez et al. (1993) Biochem. J. 293, 481–6; Sakata et al. (1993) J. Biol. Chem. 268, 13978–86; Horikawa et al. (1990) J. Biol. Chem. 265, 13683–6; De La Rosa et al. (1995) J. Biol. Chem. 270, 21860–8). The MAT II α2 subunit, which has a calculated molecular weight of 43,600, migrates on SDS-PAGE gels as a 53 kDa protein, and is postranslationally modified to generate MAT II α2' subunit (Kotb, M., and Kredich, N. M. (1985) J. Biol. Chem. 260, 3923–30). The catalytic α2/α2' subunits are found in native MAT II associated with a catalytically inactive subunit designated MAT II β, which migrates on SDS-PAGE as a 38-kDa protein (Kotb, M., and Kredich, N. M. (1985) J. Biol. Chem. 260, 3923–30; De La Rosa et al. (1992) J. Biol. Chem. 267, 10699–704; LeGros et al. (1997) J. Biol. Chem. 272, 16040–7).

Earlier work has shown that physiological activation of human lymphocytes induces downregulation of the β subunit with co-incidental alterations in MAT II kinetic properties (LeGros et al. (1997) J. Biol. Chem. 272, 16040–47). However, this differential expression of the β subunit has not been fully characterized. Further characterization of the MAT II β subunit, including the regulatory role of the MAT II β subunit, thus represents an ongoing need in the art.

SUMMARY OF THE INVENTION

The present invention discloses isolated and purified nucleic acids encoding the subunit of methionine adenosyltransferase II (MAT II), to isolated and purified MAT II β subunit polypeptides, and to the characterization of the role played by the MAT II β subunit in modulating the biological activity of MAT II. More preferably, a polypeptide of the invention is a recombinant polypeptide. Even more preferably, a polypeptide of the present invention comprises a vertebrate MAT II β subunit polypeptide. Even more preferably, a polypeptide of the present invention comprises a mammalian MAT II β subunit polypeptide. Even more preferably, a polypeptide of the present invention comprises a human MAT II β subunit polypeptide. Even more preferably, a polypeptide of the present invention comprises an amino acid sequence from the amino acid residue sequences of any of FIGS. 1–5 (corresponding to SEQ ID NOs: 17, 19, 21, 23 and 25, respectively).

The present invention also provides an isolated and purified polynucleotide that encodes a MAT II β subunit polypeptide that modulates the biological activity of MAT II. In a preferred embodiment, a polynucleotide of the present invention comprises a DNA molecule from a vertebrate species. A preferred vertebrate is a mammal. A preferred mammal is a human. More preferably, a polynucleotide of the present invention encodes a polypeptide comprising an amino acid residue sequence of any of FIGS. 1–5 (corresponding to SEQ ID NOs: 17, 19, 21, 23 and 25, respectively). Most preferably, an isolated and purified polynucleotide of the invention comprises a nucleotide base sequence of any of FIGS. 1–5.

In another embodiment, the present invention provides an antibody immunoreactive with a MAT II β subunit polypeptide as described above. FIGS. 1–5 (SEQ ID NOs: 16–25) set forth nucleotide and amino acid sequences from an exemplary vertebrates, human. Also provided by the present invention are antibodies immunoreactive with homologues or biologically equivalent MAT II β subunit polynucleotides and polypeptides found in other vertebrates. Preferably, an antibody of the invention is a monoclonal antibody. More preferably, the MAT II β subunit polypeptide comprises a human MAT II β subunit polypeptide. Even more preferably, the MAT II β subunit polypeptide comprises an amino acid residue sequence of any of FIGS. 1–5 (corresponding to SEQ ID NOs: 17, 19, 21, 23 and 25, respectively).

In another aspect, the present invention provides a process of producing an antibody immunoreactive with a MAT II β subunit polypeptide as described above, the process comprising the steps of (a) transfecting a recombinant host cell with a polynucleotide that encodes a biologically active MAT II β subunit polypeptide; (b) culturing the host cell under conditions sufficient for expression of the polypeptide; (c) recovering the polypeptide; and (d) preparing the antibody to the polypeptide. FIGS. 1–5 (SEQ ID NOs: 16–25) set forth nucleotide and amino acid sequences from an exemplary vertebrate, human. Preferably, the host cell is transfected with a polynucleotide of any of FIGS. 1–5 (SEQ ID NOs: 16, 18, 20, 22, 24, respectively). Even more preferably, the present invention provides an antibody prepared according to the process described above. Also provided by the present invention is the use of homologues or biologically equivalent polynucleotides and polypeptides found in other vertebrates to produce antibodies.

Alternatively, the present invention provides a process of detecting a MAT II β subunit polypeptide as described above, wherein the process comprises immunoreacting the polypeptide with an antibody prepared according to the process described above to form an antibody-polypeptide conjugate, and detecting the conjugate.

In yet another embodiment, the present invention provides a process of detecting a messenger RNA transcript that encodes a MAT II β subunit polypeptide as described above, wherein the process comprises hybridizing the messenger RNA transcript with a polynucleotide sequence that encodes that polypeptide to form a duplex; and detecting the duplex. Alternatively, the present invention provides a process of detecting a DNA molecule that encodes a MAT II β subunit polypeptide as described above, wherein the process comprises hybridizing DNA molecules with a polynucleotide that encodes a biologically active MAT II β subunit polypeptide to form a duplex; and detecting the duplex.

In another aspect, the present invention provides an assay kit for detecting the presence of a MAT II β subunit polypeptide in a biological sample, where the kit comprises a first container containing a first antibody capable of immunoreacting with a biologically active MAT II β subunit polypeptide, with the first antibody. Preferably, the first antibody is present in an amount sufficient to perform at least one assay. Also preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label, a fluorescent label or an enzyme.

In an alternative aspect, the present invention provides an assay kit for detecting the presence, in biological samples, of a MAT II β subunit polypeptide, the kits comprising a first container that contains a second polynucleotide identical or complementary to a segment of at least 10 contiguous nucleotide bases of a polynucleotide that encodes a biologically active MAT II β subunit polypeptide.

In another embodiment, the present invention provides an assay kit for detecting the presence, in a biological sample, of an antibody immunoreactive with a MAT II β subunit polypeptide, the kit comprising a first container containing a biologically active MAT II β subunit polypeptide that immunoreacts with the antibody, with the polypeptide present in an amount sufficient to perform at least one assay.

In still a further embodiment, this invention pertains to therapeutic methods based upon the modulation of the biological activity of MAT II via MAT II β subunit polynucleotides and polypeptides as described herein. Such therapeutic methods include administration of a soluble form of the MAT II β subunit polypeptide as well as gene therapy approaches using an isolated and purified polynucleotide of the present invention.

Thus, a key aspect of this invention pertains to the discovery of the novel MAT II β subunit polypeptides and nucleic acids. Preferred nucleic acid and amino acid sequences are described in FIGS. 1–5 (SEQ ID NOs: 16–25).

It is thus another aspect of this invention to provide a purified and isolated MAT II β subunit polypeptide having a role in the biological activity of MAT II.

The foregoing aspects and embodiments have broad utility given the biological significance of the MAT II enzyme. By way of example, the foregoing aspects and embodiments are useful in the preparation of screening assays and assay kits that are used to identify compounds that affect or modulate MAT II biological activity, or that are used to detect the presence of the proteins and nucleic acids of this invention in biological samples. Additionally, it is well known that isolated and purified polypeptides have utility as feed additives for livestock and further polynucleotides encoding the polypeptides are thus useful in producing the polypeptides.

Some of the aspects and objects of the invention having been stated hereinabove, other aspects and objects will become evident as the description proceeds, when taken in connection with the accompanying drawings and examples as best described hereinbelow.

BRIEF DESCRIPTION OF THE DRAWINGS

FIGS. 1 through 5 set forth MAT II β subunit nucleotide and amino acid sequences from an exemplary vertebrate, human, and the sequences correspond respectively to SEQ ID NOs: 16–17 (FIG. 1); 18–19 (FIG. 2); 20–21 (FIG. 3): 22–23 (FIG. 4); and 24–25 (FIG. 5). The sequences were determined from 10 clones that were amplified using sequence specific primers. The deduced amino acid sequences are shown for the ORF. Nucleotides are numbered beginning at the first position of the ORF.

FIG. 6 sets forth MAT II β subunit promoter sequence (SEQ ID NO:1) from an exemplary vertebrate, human.

FIG. 8 depicts the nucleotide sequences of cloned cDNA (SEQ ID NO:16) for the β subunit of human lymphocyte MAT II. The sequence was determined from 10 clones that were amplified using sequence specific primers. The deduced amino acid sequence (SEQ ID NO:17) is shown for the ORF. Nucleotides are numbered beginning at the first position of the ORF. Amino acid positions are shown in parentheses. Shaded amino acid residues correspond to tryptic peptide sequences that were chemically determined from purified subunit. The arrows indicate the position and direction of primers used to elucidate the sequence of subunit cDNA.

FIG. 10A depicts a silver stained SDS-PAGE of crude protein extracts from *E. coli* cells that were transfected with the pQE-30™ vector harboring the MAT II α2 subunit cDNA and expressing the recombinant α2 subunit protein (lane 1), or *E. coli* cells that were transfected with the pQE-30™ vector harboring the MAT II β subunit cDNA (lane 2).

FIG. 10B is a Western blot of the same crude material analyzed in Panel A. The blot was probed with antibodies to the β subunit protein.

FIG. 10C is a sliver stained SDS-PAGE of His-tagged recombinant β subunit protein purified from *E. coli* cells that were transfected with the pQE-30™ vector harboring the MAT II β subunit cDNA, using Ni-agarose column purification (lane 1), and purified on Ni-agarose column then further purified and eluted from a preparative SDS-PAGE (lane 2), as detailed in Methods and Results.

FIG. 10D is a Western blot of the same material analyzed in FIG. 10C, where lane 1 is the His-tagged recombinant β subunit protein eluted from the Ni-agarose column, and lane 2 is the eluted material subjected to further purification and electroelution from a preparative SDS-PAGE. The blot shown in Panel D was probed with antibodies to both the α2 and β subunits of MAT II. The antibodies to the MAT II α2 subunit recognized the crossreactive *E. coli* MAT α subunit, which co-purified with the recombinant His-tagged β subunit (lane 1), but there was no contaminating α subunit in the SDS-PAGE eluted material, lane 2.

FIG. 11A is a Western blot of the native β subunit protein expressed in PBMC extract. Lane 1 probed with antibodies to synthetic peptides copying the sequence of the N-terminal and internal β subunit protein peptides, and lane 2 is probed with antibodies to the pure recombinant β subunit protein.

FIG. 11B is a Western blot of the recombinant β subunit protein expressed in *E. coli* and purified as in legend to FIG.

10. Lane 1 probed with antibodies to synthetic peptides copying the sequence of the N-terminal and internal β subunit protein peptides, and lane 2 is probed with antibodies to the pure recombinant β subunit protein.

FIGS. 12A–D are Lineweaver-Burk plots showing the effect of recombinant β subunit protein on MAT kinetic properties. All samples were assayed for MAT activity, as described in Materials and Methods at different concentrations of L-Met.

Figure 12A:
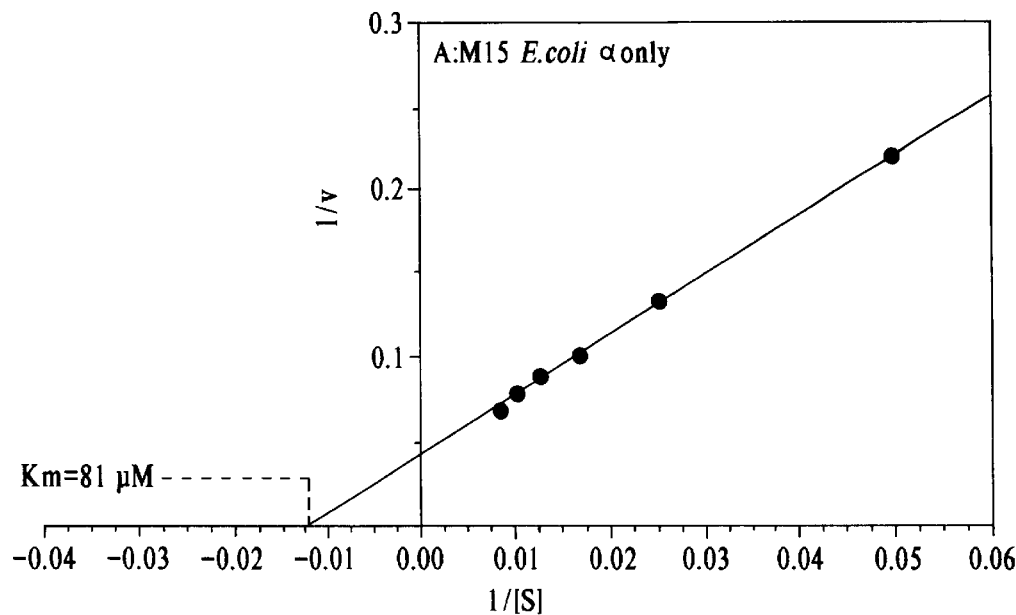

FIG. 12A is a Lineweaver-Burk plot showing MAT activity in protein extracts from untransfected E. coli cells.

Figure 12B:
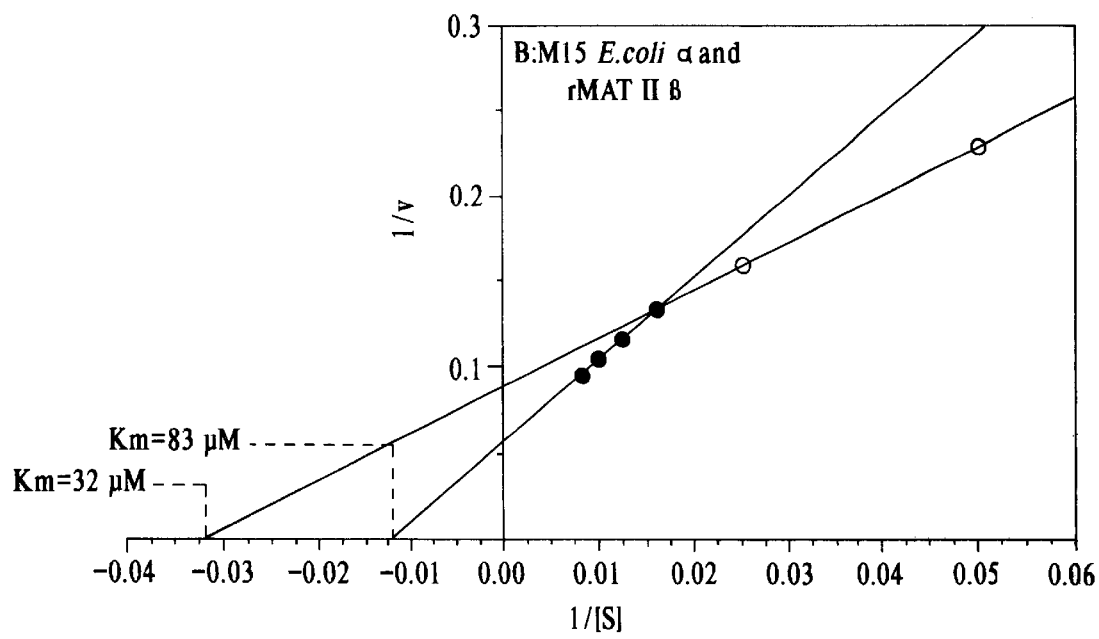

FIG. 12B is a Lineweaver-Burk plot showing MAT activity from E. coli expressing recombinant MAT II β subunit protein.

Figure 12C:
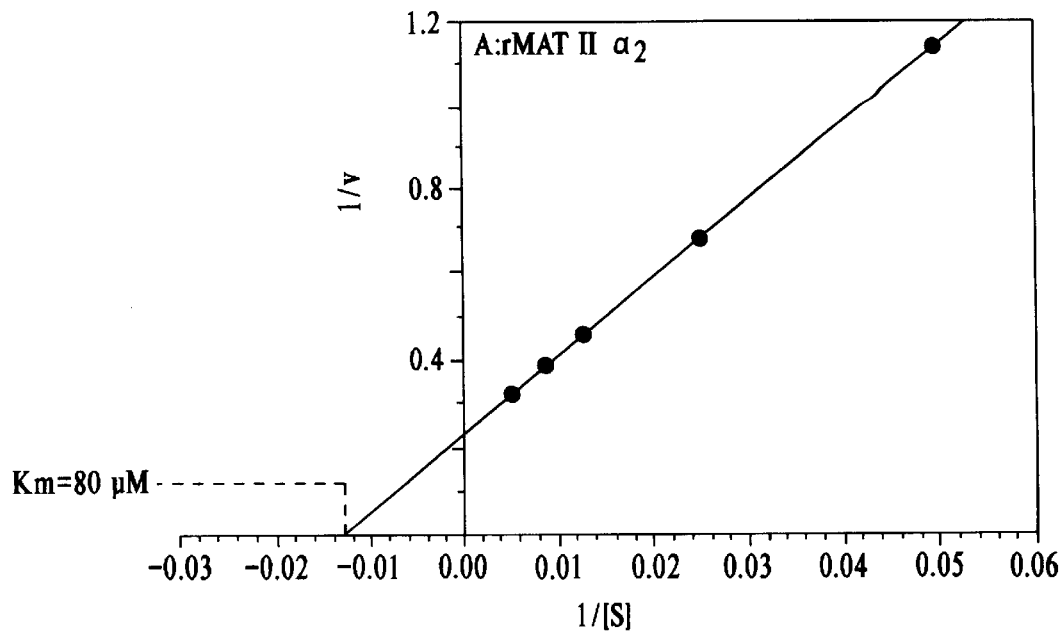

FIGS. 12C is a Lineweaver-Burk plot showing the kinetics of recombinant human MAT II α2 subunit in the absence of the recombinant MAT II β subunit protein.

Figure 12D:
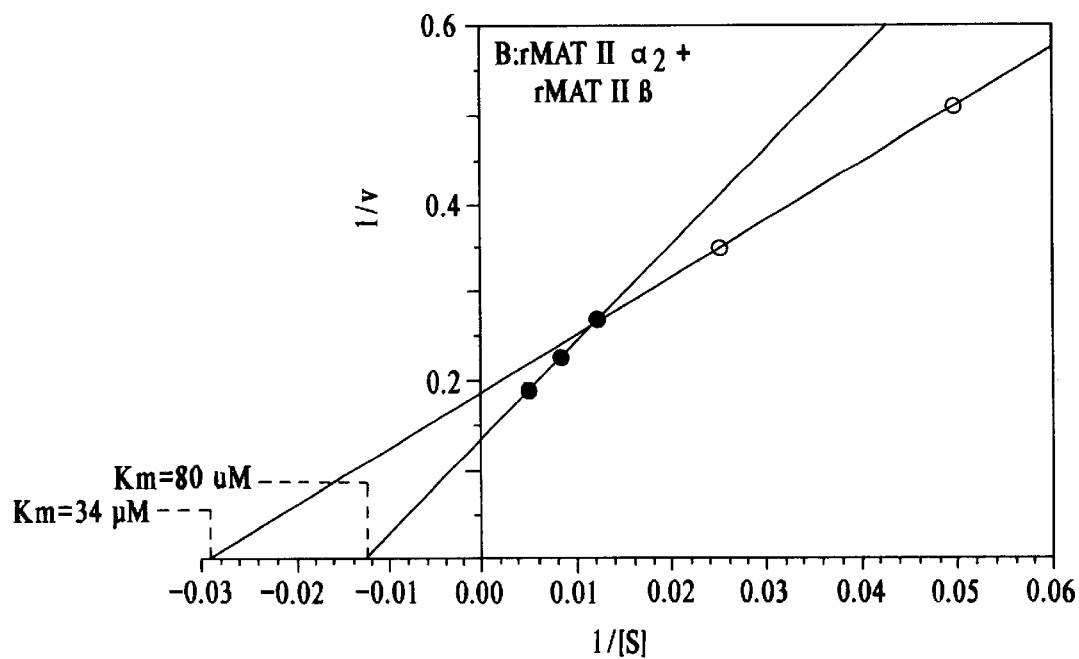

FIGS. 12D is a Lineweaver-Burk plot showing the kinetics of recombinant human MAT II α2 subunit in the presence of the recombinant MAT II β subunit protein.

Figure 13:
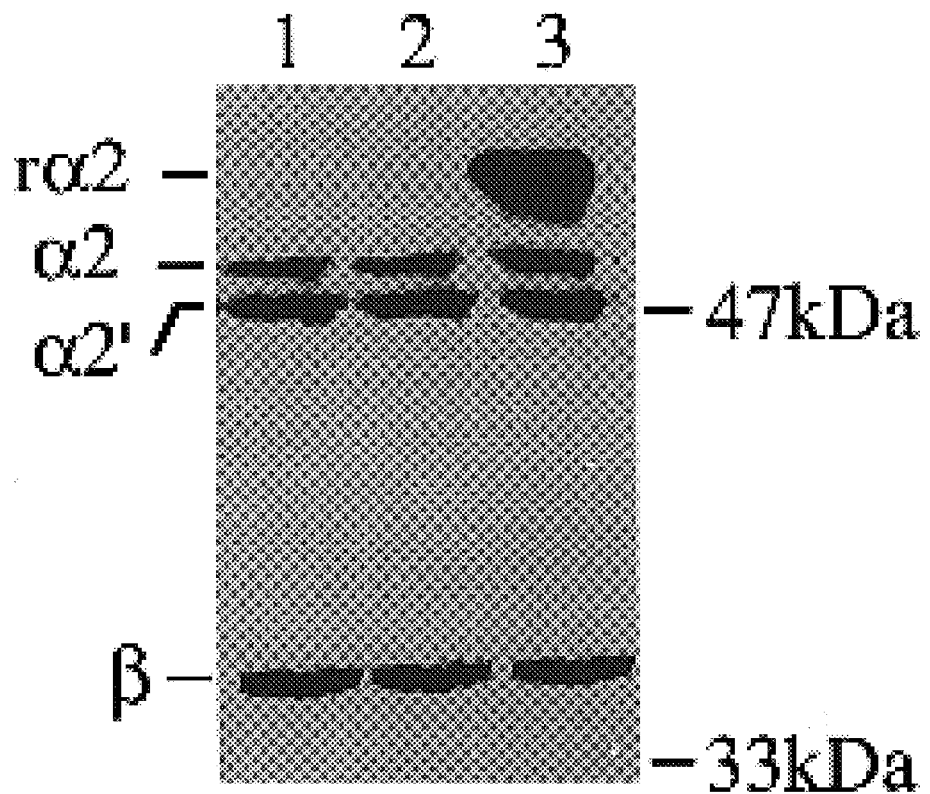

FIG. 13 depicts expression of rMAT II α2 subunit in Cos-1 cells. Cos-1 cells were transfected with pTargeT™/MAT2A vector DNA as described in the Laboratory Examples. Cells were harvested after 48 h, proteins were extracted and 40 mg were applied to 7.5% SDS-PAGE followed by transblotting onto nitrocellulose membrane which was probed with anti-MAT II α2 and b antibodies. Lane 1: untransfected Cos-1 cells; Lane 2: mock-transfected cells; and Lane 3: MAT II α2-transfected cells. The expressed r α2 protein is migrating higher than the native α2 as it contains an additional 6-His residues, and an enterokinase site at the N-terminal end.

Figure 14A:
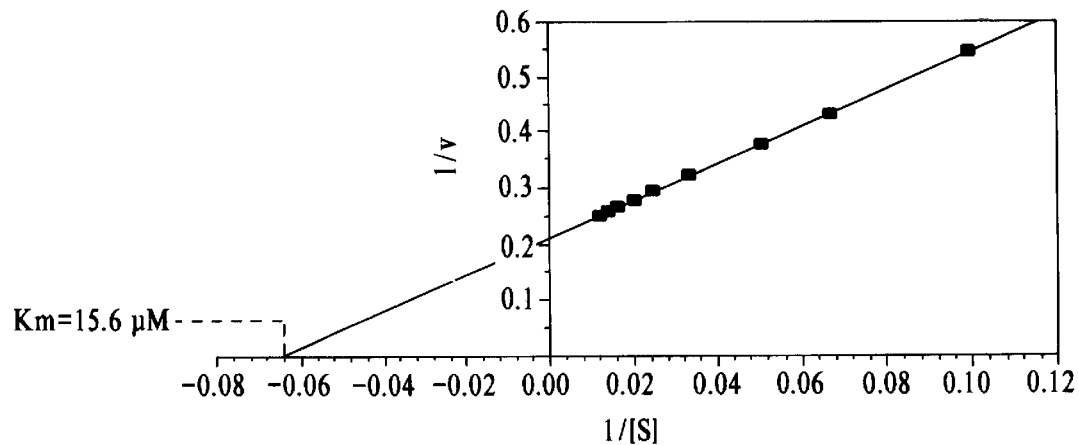
Figure 14B:
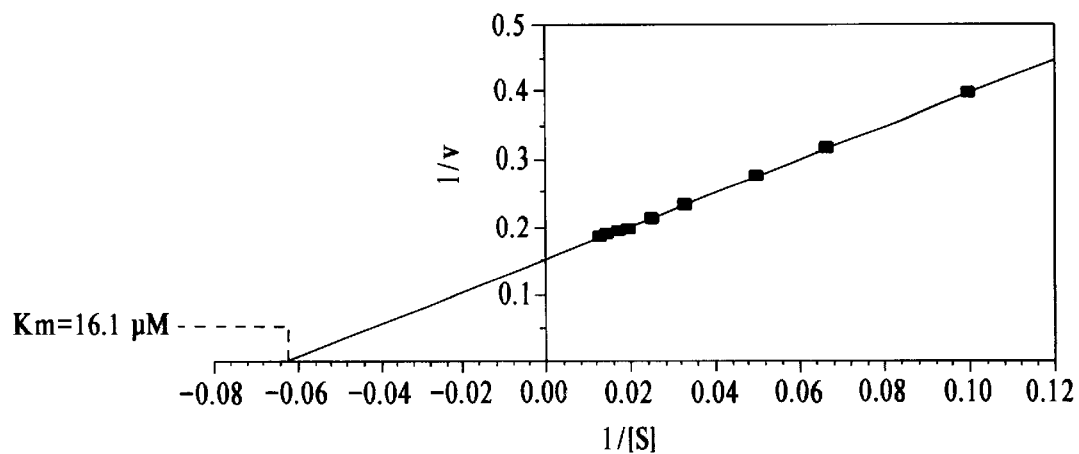
Figure 14C:
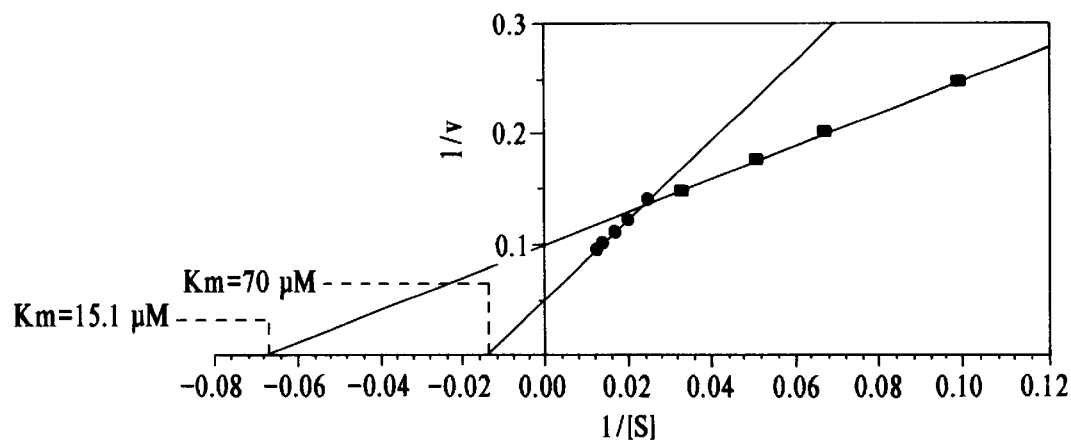

FIGS. 14A–14C depict the effect of overexpression of MAT II α2 on the enzyme kinetics in Cos-1 cells. Cellular protein extracts from untransfected, mock-transfected or pTargeT™/MAT II2A-transfected Cos-1 cells were assayed for MAT activity, at different concentrations of L-Met. Lineweaver-Burk plots (1/v versus 1/[L-Met]) were generated.

FIG. 14A depicts a Lineweaver-Burk plot of MAT activity in normal cells.

FIG. 14B depicts a Lineweaver-Burk plot of MAT activity in mock-transfected cells.

FIG. 14C depicts a Lineweaver-Burk plot of MAT activity in α2 cDNA-transfected cells.

Figure 15:
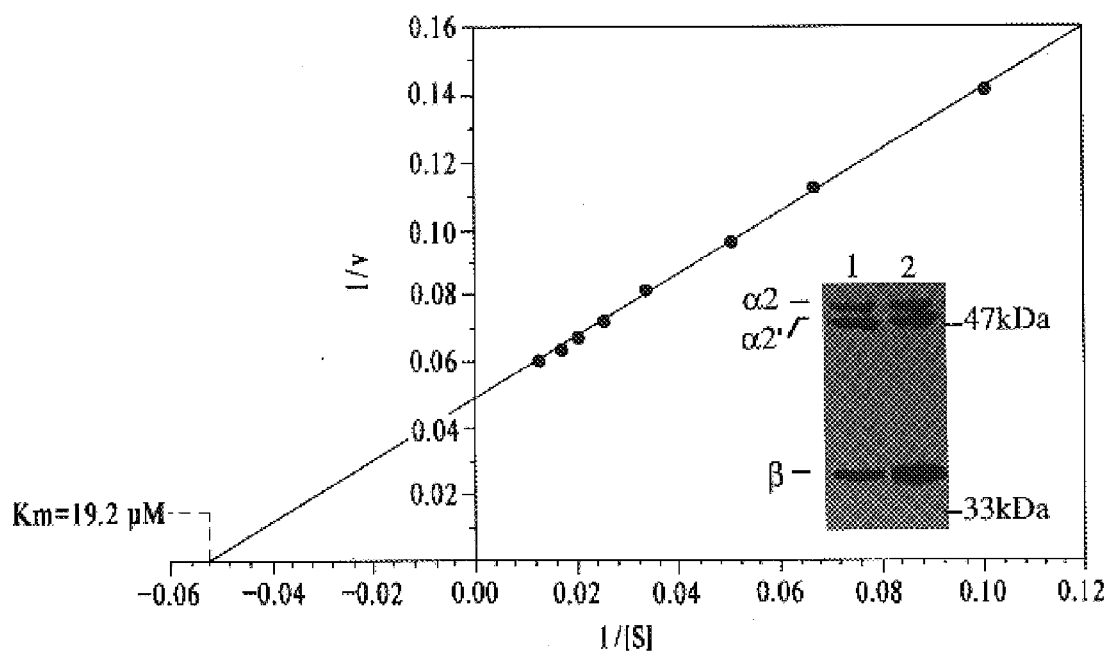

FIG. 15 depicts the effect of overexpression of MAT IIβ on the enzyme kinetics in Cos-1 cells. Cellular protein extract from pTargeT™/MATIIB-transfected Cos-1 cells was assayed for MAT activity as described in Materials and Methods, at different concentrations of L-Met. Lineweaver-Burk plot (1/v versus 1/[L-methionine]) was used to calculate Km. The figure inset depicts expression of MAT IIβ subunit in Cos-1 cells. Cos-1 cells were transfected with pTargeT™/MAT2B vector DNA. Cells were harvested after 48 h, proteins were extracted and 40 mg were applied to 7.5% SDS-PAGE followed by transblotting onto nitrocellulose membrane which was probed with anti-MAT IIα2 and β antibodies. Lane 1: untransfected Cos-1 cells; Lane 2: β cDNA-transfected cells.

Figure 16:
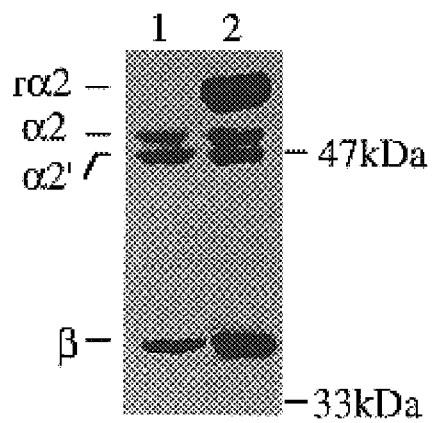

FIG. 16 depicts co-expression of rMAT IIα2 and rMAT IIβ subunits in Cos-1 cells. Cos-1 cells were co-transfected with pTargeT™/MAT2A (with His-tag and EK site) and pTargeT™/MAT2B DNA as described in Materials and Methods. Cells were harvested after 48 h, proteins were extracted and 40 mg were applied to 7.5% SDS-PAGE followed by transblotting onto nitrocellulose membrane which was probed with anti-MAT II α2 and β antibodies. Lane 1: untransfected Cos-1 cells; and Lane 2: α2 and β cDNA-transfected cells.

Figure 17A:
Figure 17B:
Figure 17C:
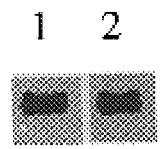

FIGS. 17A–17C depict co-migration of MAT II α2 and β subunits on native PAGE. Forty micrograms protein extracts from untransfected normal, rMAT II α2-expressing or r α2β-expressing cells were applied to 6% native polyacrylamide gel. The transblot was probed with antibody to the r α2 protein (Lane 1), developed with ECL®, stripped then reprobed with antibody to rβ protein (Lane 2).

FIG. 17A depicts co-migration of MAT II α2 and β subunits on native PAGE in untransfected cells.

FIG. 17B depicts co-migration of MAT II α2 and β subunits on native PAGE in α2-expressing cells.

FIG. 17C depicts co-migration of MAT II α2 and β subunits on native PAGE in α2β-expressing cells.

Figure 18A:
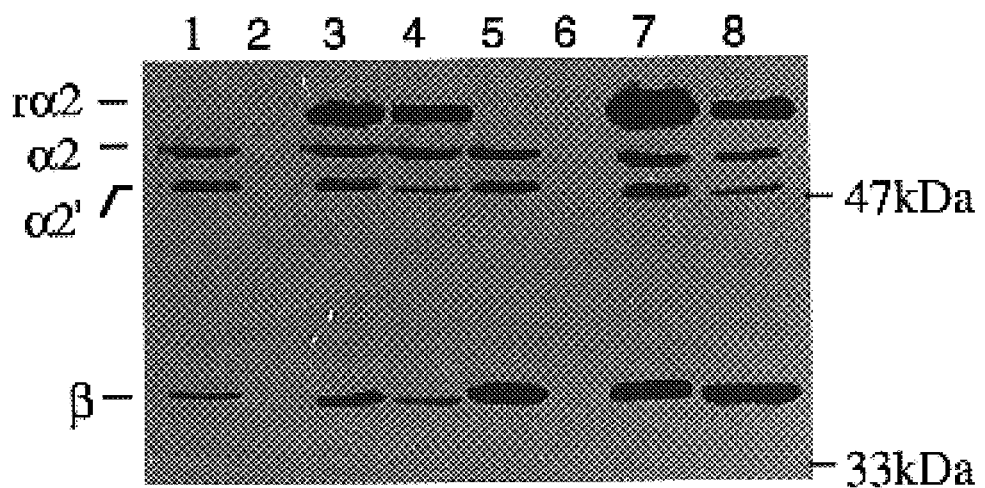
Figure 18B:
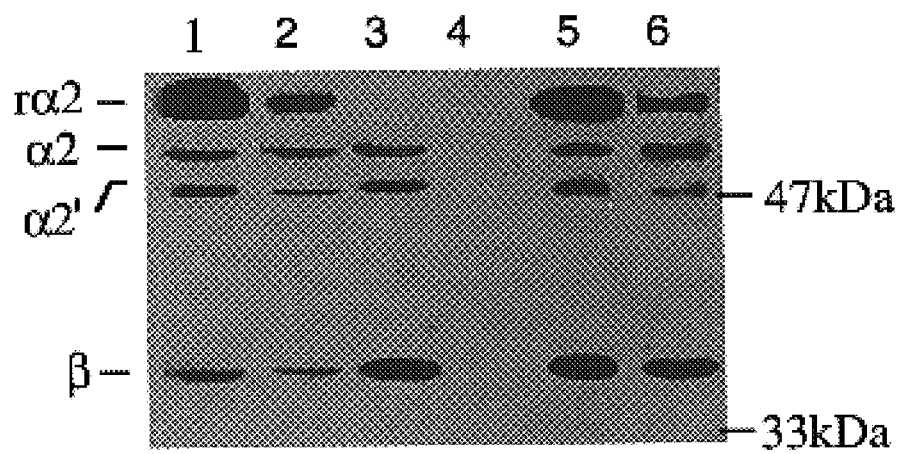

FIGS. 18A and 18B show that MAT II α2 and β subunits co-purify on Ni-agarose gel. rMAT II α2, but not rMAT II β, was expressed as a poly His-tagged protein. Cellular protein extracts from untransfected, α2, β and α2β-transfected Cos-1 cells were loaded onto Ni-agarose gel. Captured proteins were eluted in 300 mM imidazole, dialyzed against and lyophilized. Reconstituted proteins were applied to SDS-PAGE and transblotted onto nitrocellulose membranes. Transblots were probed with anti-MAT II α2 and β antibodies.

FIG. 18A depicts SDS-PAGE results in which the lane contents are as follows: Lane 1: untransfected cell extract; Lane 2: untransfected cell extract after separation on Ni-agarose; Lane 3: α2-expressing cell extract; Lane 4: α2-expressing cell extract after separation on Ni-agarose; Lane 5: β-expressing cell extract; Lane 6: β-expressing cell extract after separation on Ni-agarose; Lane 7: α2β-co-expressing cell extract; Lane 8: α2β-co-expressing cell extract after separation on Ni-agarose.

FIG. 18B depicts SDS-PAGE after the same purification procedure as described for FIG. 18A was followed for mixed extracts from 2-expressing cells and -expressing cells. In FIG. 18B, the lane contents are as follows: Lane 1: α2-expressing cell extract; Lane 2: α2-expressing cell extract after separation on Ni-agarose; Lane 3: β-expressing cell extract; Lane 4: β-expressing cell extract after separation on Ni-agarose; Lane 5: mixed extracts from α2- and β-expressing cells; Lane 6: mixed extracts from α2- and β-expressing cells after separation on Ni-agarose column.

Figure 19:
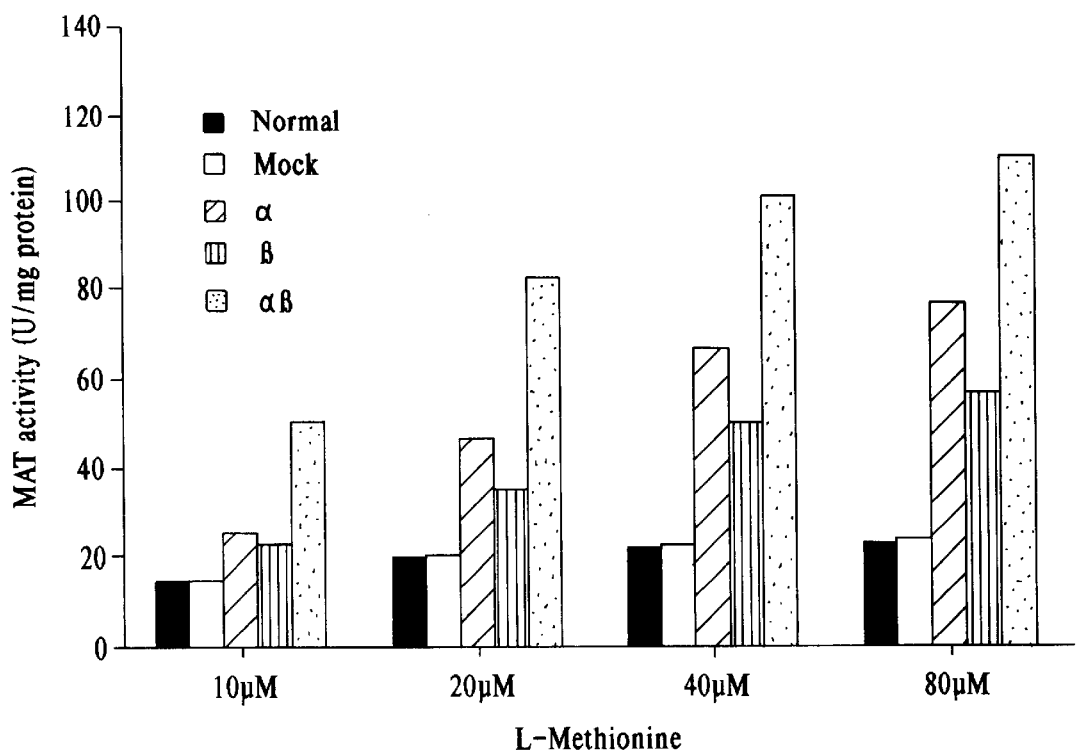

FIG. 19 depicts the effect of co-expression of MAT IIα2 and β on MAT specific activity in Cos-1 cells. Cellular protein extracts were assayed for MAT activity, as described in Materials and Methods at different concentrations of L-Met. Normal: untransfected Cos-1 cells; mock: mock-transfected; a: α2 cDNA-transfected; b: β cDNA-transfected; and ab: α2 cDNA-, and β cDNA-co-transfected Cos-1 cells.

Figure 20:
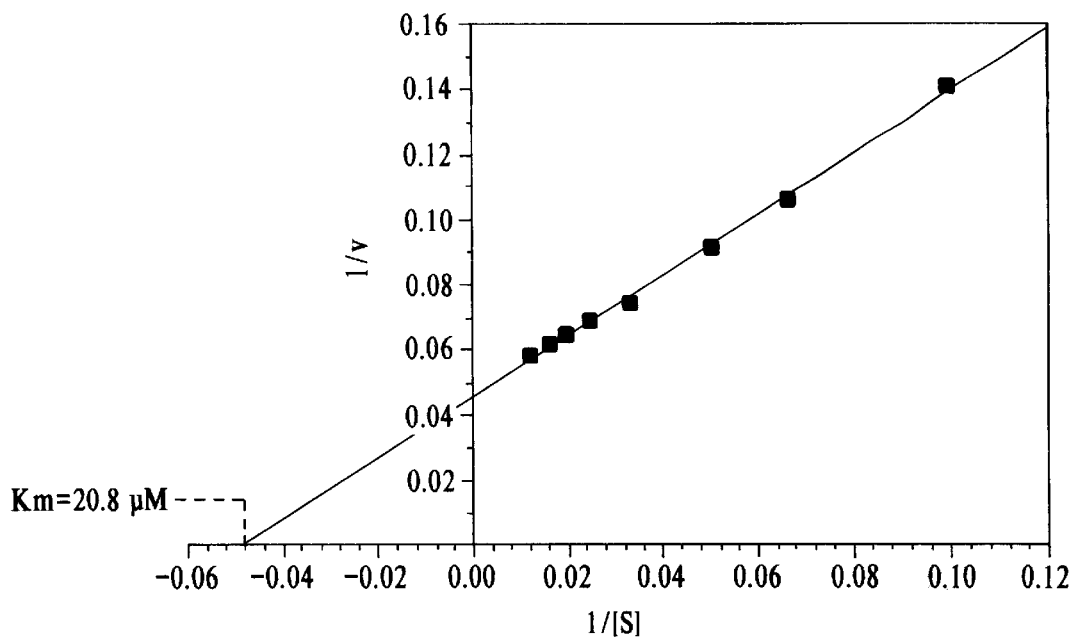

FIG. 20 depicts the effect of co-expression of MAT IIα2 and β on the enzyme kinetics in Cos-1 cells. MAT activity was assayed at different concentrations of L-Met. Lineweaver-Burk plot (1/v versus 1/[L-Met] was used to calculate Km.

Figure 21:
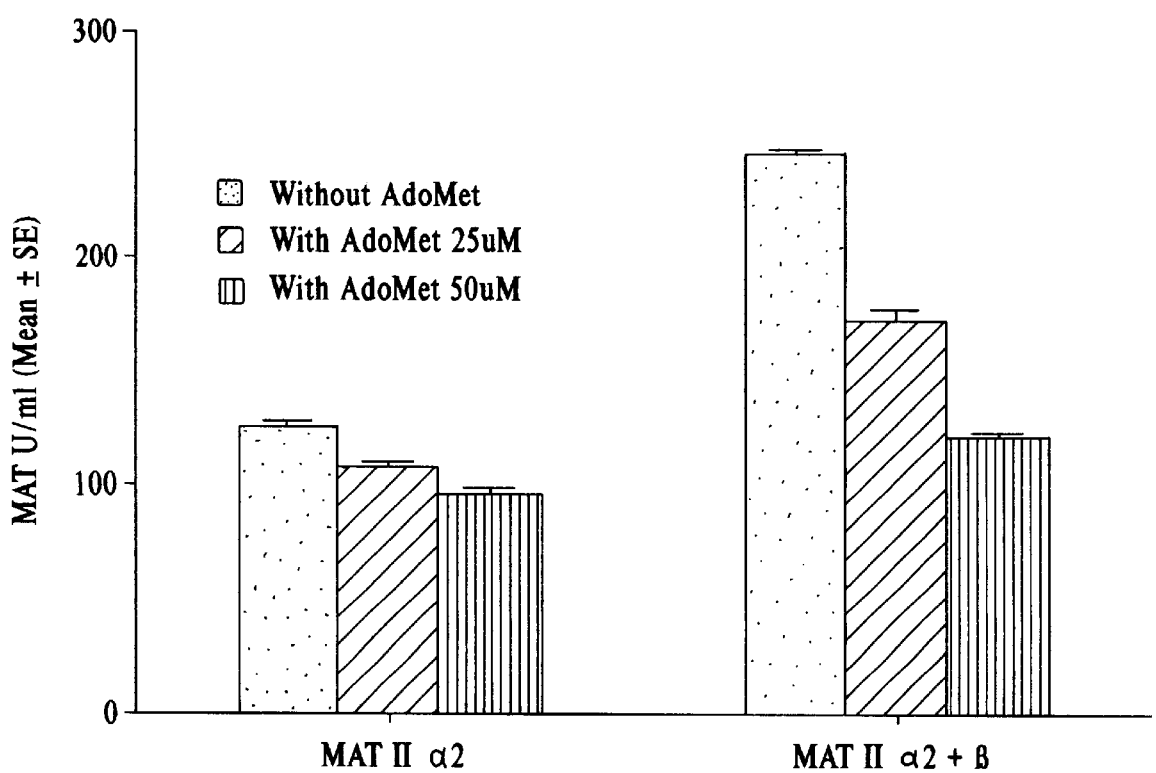

FIG. 21 depicts the effect of rMAT IIβ on the feedback inhibition of MAT II by AdoMet. MAT assay was conducted as in Materials and Methods at 20 mM of L-Met. AdoMet was added to a final concentration of 25 or 50 mM to rMAT IIα2 in the absence or presence of rMAT II β subunit.

DETAILED DESCRIPTION OF THE INVENTION

In accordance with the present invention the complete sequence of cDNA encoding the entire MAT II β subunit is disclosed. The present invention also discloses that the protein expressed in *E. coli* associates with the *E. coli* as well as the human catalytic α subunits of MAT. The association of mammalian β and α2 subunits changed the kinetic properties of the α2 subunit, thereby providing direct evidence for the regulatory role of the MAT II β subunit. The present invention also shows the association of MAT II α2 and β subunits with consequent changes in enzyme kinetic and regulatory properties. This is a mechanism by which AdoMet levels are controlled during cell growth and differentiation.

Thus, the present invention pertains to isolated and purified nucleic acids encoding the β subunit of methionine adenosyltransferase II (MAT II), to isolated and purified MAT II β subunit polypeptides, and to the characterization of the role played by the MAT II β subunit in modulating the biological activity of MAT II.

Methionine adenosyltransferase (MAT) II is a key enzyme required for every living cell. For this reason, all organisms examined thus far have at least two genes that encode for two MAT enzymes. In humans the MAT I/III enzyme is found only in liver and this protein is encoded by MATIA gene. MAT II is found in all human tissues and it is made of two nonidentical subunits that are called alpha (α2) and beta (β). The α2 subunit is encoded by the MAT2A gene, whereas, the β subunit is encoded by a putative MAT2B gene.

MAT is responsible for the synthesis of one of the most important molecules in living organisms, called S-adenosylmethionine (AdoMet, or SAM). This compound has a methyl ($-CH_3$) group that can be transferred to other molecules, resulting in major changes in their activity. For example, when certain parts of the DNA are methylated (i.e., receive the $-CH_3$ group from AdoMet), the gene can be turned on or off. It has been shown that in certain types of cancer there is abnormalities in the methylation of specific DNA regions and that this results in aberrant expression of proteins and leads to malignancy. See Belinsky et al., *Proc. Natl. Acad. Sci. USA* (1998) 20:11891–6; Ahuja et al., *Cancer Res.* (1998)23:5489–94; Klump et al., *Gastroenterology* (1998) 6:1381–6.

The importance of regulating AdoMet levels and methylation reactions can be seen in certain types of cancer where an abnormal amount of methylation can result in the suppression or over-expression of critical genes. Cells have a finely controlled cycle of division followed by cell death. A disruption of this cycle can result in abnormal amount of cell growth resulting in the development of tumors. See Belinsky et al., *Proc. Natl. Acad. Sci. USA* (1998) 20:11891–6; Ahuja et al., *Cancer Res.* (1998) 23:5489–94; Klump et al., *Gastroenterology* (1998) 6:1381–6. For the above reasons, MAT has been studied for years as a possible target for chemotherapy. Many scientists tried to develop inhibitors of this enzyme but most chemical inhibitors are highly toxic or lack specificity. Further, the synthesis of these chemical inhibitors is costly.

The present inventors have found that the activity of MAT II can be regulated by its β subunit. When β expression is absent, the MAT II α2 subunits make at least 5–10 fold more AdoMet in the cell as compared to when β is expressed. In addition in the absence of the β subunit, MAT II is less susceptible to feedback inhibition by its own product, AdoMet. Together, these two mechanisms lead to accumulation of high levels of AdoMet and this is bound to affect the methylation status of DNA, RNA, protein, lipids as well as affect the metabolism of another important class of molecules called the polyamines. This, modulation of the expression of the MAT II β subunit via molecular methods provides for changes in the activity of MAT II and this provides a tool for cancer therapy and autoimmunity therapy.

Summarily, the identification of the gene that encodes the β subunit, the cloning of the cDNA and the expression of the protein affords the molecular tool required for modulating MAT activity with application to the fields of cancer, autoimmunity and transplantation.

A. Definitions and Techniques Affecting Polypeptides and Nucleic Acids

As used in the following detailed description and in the claims, the term "MAT II β subunit" includes MAT II β subunit nucleic acids and polypeptides that modulate the biological activity of the MAT II enzyme. Preferably, MAT II β subunit nucleic acids and polypeptides are isolated from eukaryotic sources. Thus, the term "MAT II β subunit" also includes invertebrate homologs. The term "MAT II β subunit" further includes vertebrate homologs of MAT II β subunit members, including, but not limited to, mammalian and avian homologs. Preferred mammalian homologs of MAT II β subunit members include, but are not limited to, murine, bovine and human homologs.

The terms "MAT II β subunit gene product", "MAT II β subunit protein" and "MAT II β subunit polypeptide" refer to proteins having amino acid sequences which are substantially identical to the native amino acid sequences in the MAT II β subunit and which are biologically active in that they are capable of modulating MAT II biological activity, or cross-reacting with anti-MAT II β subunit antibodies raised against a MAT II β subunit polypeptide.

The terms "MAT II β subunit gene product", "MAT II β subunit protein" and "MAT II β subunit polypeptide" also include analogs of MAT II β subunit molecules which exhibit at least some biological activity in common with native MAT II β subunit gene products. Furthermore, those skilled in the art of mutagenesis will appreciate that other analogs, as yet undisclosed or undiscovered, can be used to construct MAT II β subunit analogs. There is no need for an "MAT II β subunit gene product", "MAT II β subunit protein" or "MAT II β subunit polypeptide" to comprise all, or substantially all of the amino acid sequence of a native MAT II β subunit gene product. Shorter or longer sequences are anticipated to be of use in the invention. Thus, the term "MAT II β subunit gene product" also includes fusion or recombinant MAT II β subunit polypeptides and proteins. Methods of preparing such proteins are described herein in the Laboratory Examples appended hereto, among other places.

The terms "MAT II β subunit gene", "MAT II β subunit gene sequence" and "MAT II β subunit gene segment" refer to any DNA sequence that is substantially identical to a polynucleotide sequence encoding a MAT II β subunit gene product, MAT II β subunit protein or MAT II β polypeptide as defined above. The terms also refer to RNA, or antisense sequences, compatible with such DNA sequences. A "MAT II β subunit gene", "MAT II β subunit gene sequence" and "MAT II β subunit gene segment" can also comprise any combination of associated control sequences.

The term "substantially identical", when used to define either a MAT II β subunit gene product or MAT II β subunit amino acid sequence, or a MAT II β subunit gene or MAT II β subunit nucleic acid sequence, means that a particular sequence, for example, a mutant sequence, varies from the sequence of a natural MAT II β subunit by one or more deletions, substitutions, or additions, the net effect of which is to retain at least some of biological activity of the MAT II β subunit. Alternatively, DNA analog sequences are "substantially identical" to specific DNA sequences disclosed herein if: (a) the DNA analog sequence is derived from coding regions of the natural MAT II β subunit gene; or (b) the DNA analog sequence is capable of hybridization of DNA sequences of (a) under moderately stringent conditions and which encode biologically active MAT II β subunit gene product; or (c) the DNA sequences are degenerative as a result of the genetic code to the DNA analog sequences defined in (a) and/or (b). Substantially identical analog proteins will be greater than about 60% identical to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences.

A.1. Sequence Similarity and Identity

As used herein, the term "substantially similar" means that a particular sequence varies from a MAT II β subunit nucleic acid sequence, or a MAT II β subunit amino acid sequence by one or more deletions, substitutions, or additions, the net effect of which is to retain at least some of biological activity of the natural gene, gene product, or sequence. Such sequences include "mutant" or "polymorphic" sequences, or sequences in which the biological activity is altered to some degree but retains at least some of the original biological activity.

Nucleic acids that are substantially identical to a sequence set forth in any of FIGS. 1–5 (SEQ ID NOs:16–25— preferred MAT II β subunit sequences), e.g. allelic variants, genetically altered versions of the gene, etc., bind to the provided MAT II β subunit sequences under stringent hybridization conditions. By using probes, particularly labeled probes of DNA sequences, one can isolate homologous or related genes. The source of homologous genes can be any species, e.g. primate species, rodents (such as rats and mice), canines, felines, bovines, equines, etc.

Between mammalian species, e.g. human and mouse, homologs have substantial sequence similarity, i.e. at least 75% sequence identity between nucleotide sequences. Sequence similarity is calculated based on a reference sequence, which can be a subset of a larger sequence, such as a conserved motif, coding region, flanking region, etc. A reference sequence will usually be at least about 18 nt long, more usually at least about 30 nt long, and can extend to the complete sequence that is being compared. Algorithms for sequence analysis are known in the art, such as BLAST, described in Altschul et al. (1990) J. Mol. Biol. 215: 403–10. In determining nucleic acid sequences, all subject nucleic acid sequences capable of encoding substantially similar amino acid sequences are considered to be substantially similar to a reference nucleic acid sequence, regardless of differences in codon sequences or substitution of equivalent amino acids to create biologically functional equivalents.

Percent identity or percent similarity of a DNA or peptide sequence can be determined, for example, by comparing sequence information using the GAP computer program, available from the University of Wisconsin Geneticist Computer Group. The GAP program utilizes the alignment method of Needleman et al., (1970) J. Mol. Biol. 48:443, as revised by Smith et al., (1981) Adv. Appl. Math. 2: 482. Briefly, the GAP program defines similarity as the number of aligned symbols (i.e., nucleotides or amino acids) which are similar, divided by the total number of symbols in the shorter of the two sequences. The preferred parameters for the GAP program are the default parameters, which do not impose a penalty for end gaps. See Schwartz et al., eds., (1979), Atlas of Protein Sequence and Structure, National Biomedical Research Foundation, pp. 357–358; Gribskov et al., (1986) Nucl. Acids. Res. 14: 6745.

The term "similarity" is contrasted with the term "identity". Similarity is defined as above; "identity", however, means a nucleic acid or amino acid sequence having the same amino acid at the same relative position in a given family member of a gene family. Homology and similarity are generally viewed as broader terms than the term identity. Biochemically similar amino acids, for example leucine and isoleucine or glutamate/aspartate, can be present at the same position—these are not identical per se, but are biochemically "similar." As disclosed herein, these are referred to as conservative differences or conservative substitutions. This differs from a conservative mutation at the DNA level, which changes the nucleotide sequence without making a change in the encoded amino acid, e.g. TCC to TCA, both of which encode serine.

As used herein, DNA analog sequences are "substantially identical" to specific DNA sequences disclosed herein if: (a) the DNA analog sequence is derived from coding regions of the nucleic acid sequence shown in any of FIGS. 1–5 (SEQ ID NOs: 16–25, respectively); or (b) the DNA analog sequence is capable of hybridization of DNA sequences of (a) under stringent conditions and which encode a biologically active gene product of the nucleic acid sequence shown in any of FIGS. 1–5 (SEQ ID NOs:16–25, respectively); or (c) the DNA sequences are degenerate as a result of alternative genetic code to the DNA analog sequences defined in (a) and/or (b). Substantially identical analog proteins will be greater than about 60% identical to the corresponding sequence of the native protein. Sequences having lesser degrees of identity but comparable biological activity are considered to be equivalents.

As used herein, "stringent conditions" means conditions of high stringency, for example 6×SSC, 0.2% polyvinylpyrrolidone, 0.2% Ficoll, 0.2% bovine serum albumin, 0.1% sodium dodecyl sulfate, 100 g/mL salmon sperm DNA and 15% formamide at 68° C. For the purposes of specifying additional conditions of high stringency, preferred conditions are salt concentration of about 200 mM and temperature of about 45° C. One example of such stringent conditions is hybridization at 4×SSC, at 65° C., followed by a washing in 0.1×SSC at 65° C. for one hour. Another exemplary stringent hybridization scheme uses 50% formamide, 4×SSC at 42° C.

In contrast, nucleic acids having sequence similarity are detected by hybridization under lower stringency conditions. Thus, sequence identity can be determined by hybridization under lower stringency conditions, for example, at 50° C. or higher and 0.1×SSC (9 mM NaCl/0.9 mM sodium citrate) and the sequences will remain bound when subjected to washing at 55° C. in 1×SSC.

Thus, in certain embodiments, the invention concerns the use of MAT II β subunit genes and gene products that include within their respective sequences a sequence which is essentially that of a MAT II β subunit gene, or the corresponding protein. The term "a sequence essentially as that of a MAT II β subunit gene", means that the sequence is substantially identical to a portion of a MAT II β subunit gene and contain a minority of bases or amino acids (whether DNA or protein) which are not identical to those of a MAT II β subunit protein or a MAT II β subunit gene, or which are not a biologically functional equivalent. The term "biologically functional equivalent" is well understood in the art and is further defined in detail herein.

Nucleotide sequences are "substantially identical" where they have between about 70% and about 80% or more preferably, between about 81% and about 90%, or even more preferably, between about 91% and about 99%, sequence identity for nucleic acid residues which are identical to the nucleotide sequence of a MAT II β subunit gene.

Peptide sequences which have about 35%, or 45%, or preferably from 45–55%, or more preferably 55–65%, or most preferably 65% or greater amino acids which are identical or functionally equivalent or biologically functionally equivalent to the amino acids of a MAT II β subunit polypeptide will be sequences which are "substantially similar".

The term "homology" describes a mathematically based comparison of sequence similarities which is used to identify genes or proteins with similar functions or motifs. Accordingly, the term "homology" is synonymous with the term "similarity" and "percent similarity" as defined above. Thus, the phrases "substantial homology" or "substantial similarity" have similar meanings.

A.2. Nucleic Acid Sequences

In certain embodiments, the invention concerns the use of MAT II β subunit genes and gene products that include within their respective sequences a sequence which is essentially that of a MAT II β subunit gene, or the corresponding protein. The term "a sequence essentially as that of a MAT II β subunit gene", means that the sequence substantially corresponds to a portion of a MAT II β subunit or MAT II β subunit gene and has relatively few bases or amino acids (whether DNA or protein) which are not identical to those of a MAT II β subunit protein or MAT II β subunit gene, (or a biologically functional equivalent of, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of a MAT II β subunit polypeptide or MAT II β subunit gene, will be sequences which are "essentially the same".

MAT II β subunit gene products and MAT II β subunit-encoding nucleic acid sequences which have functionally equivalent codons are also covered by the invention. The term "functionally equivalent codon" is used herein to refer to codons that encode the same amino acid, such as the six codons for arginine or serine. Thus, when referring to the sequence examples presented in FIGS. 1–5 (SEQ ID NOs: 16–25) applicants provide substitution of functionally equivalent codons of Table 1 into the sequence examples of FIGS. 1–5 (SEQ ID NOs: 16, 18, 20, 22, 24, respectively). Thus, applicants are in possession of amino acid and nucleic acids sequences which include such substitutions but which are not set forth herein in their entirety for convenience.

Alternatively, functionally equivalent proteins or peptides can be created via the application of recombinant DNA technology, in which changes in the protein structure can be engineered, based on considerations of the properties of the amino acids being exchanged, e.g. substitution of Ile for Leu at amino acids 8, 32, 175 and/or 271 for MAT II β subunit as set forth in FIGS. 1–5 and in SEQ ID NOs: 17, 19, 21, 23 and 25. Changes designed by man can be introduced through the application of site-directed mutagenesis techniques, e.g., to introduce improvements to the antigenicity of the protein or to test MAT II β subunit mutants in order to examine MAT II β subunit activity, or other activity at the molecular level.

The term "functionally equivalent codon" is also used herein to refer to codons that encode biologically equivalent amino acids (see Table 1). Thus, when referring to the sequence examples presented in FIGS. 1–5 (SEQ ID NOs: 16–25) applicants provide substitution from Table 1 of codons that encode biologically equivalent amino acids as described herein into the sequence examples of FIGS. 1–5 (SEQ ID NOs: 16, 18, 20, 22, 24, respectively). Thus, applicants are in possession of amino acid and nucleic acids sequences which include such substitutions but which are not set forth herein in their entirety for convenience.

TABLE 1

Functionally Equivalent Codons.

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic Acid | Asp | D | GAC | GAU | | | | |
| Glumatic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | ACG | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It will also be understood that amino acid and nucleic acid sequences can include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or can include various internal sequences, i.e., introns, which are known to occur within genes.

The present invention also encompasses the use of DNA segments which are complementary, or essentially complementary, to the sequences set forth in the specification. Nucleic acid sequences which are "complementary" are those which are base-pairing according to the standard Watson-Crick complementarity rules. As used herein, the term "complementary sequences" means nucleic acid sequences which are substantially complementary, as can be assessed by the same nucleotide comparison set forth above, or as defined as being capable of hybridizing to the nucleic acid segment in question under relatively stringent conditions such as those described herein. A particular example of a provided complementary nucleic acid segment is an antisense oligonucleotide.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. (See, e.g., Wetmur & Davidson, 1968).

Probe sequences can also hybridize specifically to duplex DNA under certain conditions to form triplex or other higher order DNA complexes. The preparation of such probes and suitable hybridization conditions are well known in the art.

As used herein, the term "DNA segment" refers to a DNA molecule which has been isolated free of total genomic DNA of a particular species. Furthermore, a DNA segment encoding a MAT II β subunit polypeptide refers to a DNA segment which contains MAT II β subunit coding sequences, yet is isolated away from, or purified free from, total genomic DNA of a source species, such as Homo sapiens. Included within the term "DNA segment" are DNA segments and smaller fragments of such segments, and also recombinant vectors, including, for example, plasmids, cosmids, phages, viruses, and the like.

Similarly, a DNA segment comprising an isolated or purified MAT II β subunit gene refers to a DNA segment including MAT II β subunit coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, the MAT II β subunit gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode a MAT II β subunit polypeptide that includes within its amino acid sequence an amino acid sequence selected from any of FIGS. 1–5 (corresponding to SEQ ID NOs: 17, 19, 21, 23 and 25, respectively). In other particular embodiments, the invention concerns isolated DNA segments and recombinant vectors incorporating DNA sequences which encode a protein that includes within its amino acid sequence the amino acid sequence of a MAT II β subunit polypeptide corresponding to human tissues.

It will also be understood that this invention is not limited to the particular nucleic acid and amino acid sequences of FIGS. 1–5 (SEQ ID NOs: 16–25). Recombinant vectors and isolated DNA segments can therefore variously include the MAT II β subunit polypeptide-encoding region itself, include coding regions bearing selected alterations or modifications in the basic coding region, or include encoded larger polypeptides which nevertheless include MAT II β subunit polypeptide-encoding regions or can encode biologically functional equivalent proteins or peptides which have variant amino acid sequences.

In certain embodiments, the invention concerns isolated DNA segments and recombinant vectors which encode a protein or peptide that includes within its amino acid sequence an amino acid sequence essentially as set forth in any of FIGS. 1–5 (corresponding to SEQ ID NOs: 17, 19, 21, 23 and 25, respectively). Naturally, where the DNA segment or vector encodes a full length MAT II β subunit gene product, the most preferred nucleic acid sequence is that which is essentially as set forth in any of FIGS. 1–5 (SEQ ID NOs: 16, 18, 20, 22, 24, respectively) and which encode a protein that exhibits activity in the modulation of MAT II biological activity, as can be determined by, for example, evaluating the change in MAT II kinetic properties (e.g. $K_m$ for L-Met, and feedback inhibition by AdoMet), as disclosed herein.

The term "a sequence essentially as set forth in any of FIGS. 1–5" means that the sequence substantially corresponds to a portion of an amino acid sequence of any of FIGS. 1–5 (corresponding to SEQ ID NOs: 17, 19, 21, 23 and 25, respectively) and has relatively few amino acids which are not identical to, or a biologically functional equivalent of, the amino acids of an amino acid sequence of any of FIGS. 1–5 (corresponding to SEQ ID NOs: 17, 19, 21, 23 and 25, respectively). The term "biologically functional equivalent" is well understood in the art and is further defined in detail herein. Accordingly, sequences, which have between about 70% and about 80%; or more preferably, between about 81% and about 90%; or even more preferably, between about 91% and about 99%; of amino acids which are identical or functionally equivalent to the amino acids of any of FIGS. 1–5 (corresponding to SEQ ID NOs: 17, 19, 21, 23 and 25, respectively), will be sequences which are "a sequence essentially as set forth in any of FIGS. 1–5".

In particular embodiments, the invention concerns gene therapy methods that use isolated DNA segments and recombinant vectors incorporating DNA sequences which encode a protein that includes within its amino acid sequence an amino acid sequence of any of FIGS. 1–5 (corresponding to SEQ ID NOs: 17, 19, 21, 23 and 25, respectively). In other particular embodiments, the invention concerns isolated DNA sequences and recombinant DNA vectors incorporating DNA sequences which encode a protein that includes within its amino acid sequence the amino acid sequence of the MAT II β subunit protein from human tissue.

In certain other embodiments, the invention concerns isolated DNA segments and recombinant vectors that include within their sequence a nucleic acid sequence essentially as set forth in any of FIGS. 1–5 and 6 (SEQ ID NOs: 16, 18, 20, 22, 24, 1, respectively). The term "a sequence essentially as set forth in any of FIGS. 1–6" is used in the same sense as described above and means that the nucleic acid sequence substantially corresponds to a portion of FIGS. 1–5 and 6, and has relatively few codons which are not identical, or functionally equivalent, to the codons of FIGS. 1–6 (SEQ ID NOs: 16, 18, 20, 22, 24, 1, respectively). Again, DNA segments which encode polypeptides exhibiting activity in the modulation of MAT II biological activity, or other biological activity will be most preferred. The term "functionally equivalent codon" is used herein to refer to codons that encode the same amino acid, such as the six codons for arginine or serine, and also to refer to codons that encode biologically equivalent amino acids (see Table 1).

The nucleic acid segments of the present invention, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol. For example, nucleic acid fragments can be prepared which include a short stretch complementary to a nucleic acid sequence set forth in any of FIGS. 1–5 (SEQ ID NOs: 16, 18, 20, 22, 24, respectively), such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

The DNA segments of the present invention encompass biologically functional equivalent MAT II β subunit proteins and peptides. Such sequences can rise as a consequence of codon redundancy and functional equivalency which are known to occur naturally within nucleic acid sequences and the proteins thus encoded. Alternatively, functionally equivalent proteins or peptides can be created via the application of recombinant DNA technology, in which changes in the protein structure can be engineered, based on considerations of the properties of the amino acids being exchanged. Changes designed by man can be introduced through the application of site-directed mutagenesis techniques, e.g., to introduce improvements to the antigenicity of the protein or to test MAT II β subunit mutants in order to examine activity in the modulation of MAT II, or other activity at the molecular level.

If desired, one can also prepare fusion proteins and peptides, e.g., where the MAT II β subunit coding region is aligned within the same expression unit with other proteins or peptides having desired functions, such as for purification or immunodetection purposes (e.g., proteins which can be purified by affinity chromatography and enzyme label coding regions, respectively).

Recombinant vectors form important further aspects of the present invention. Particularly useful vectors are contemplated to be those vectors in which the coding portion of the DNA segment is positioned under the control of a promoter. The promoter can be in the form of the promoter which is naturally associated with the MAT II β subunit gene, e.g., in mammalian tissues, as can be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a MAT II β subunit gene in its natural environment. Such promoters can include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al., 1989, specifically incorporated herein by reference. The promoters employed can be constitutive, or inducible, and can be used under the appropriate conditions to direct high level expression of the introduced DNA segment, such as is advantageous in the large-scale production of recombinant proteins or peptides. Appropriate promoter systems provided for use in high-level expression include, but are not limited to, the vaccina virus promoter and the baculovirus promoter.

In an alternative embodiment, the present invention provides an expression vector comprising a polynucleotide that encodes a biologically active MAT II β subunit polypeptide in accordance with the present invention. Also preferably, an expression vector of the present invention comprises a polynucleotide that encodes human MAT II β subunit gene product. More preferably, an expression vector of the present invention comprises a polynucleotide that encodes a polypeptide comprising an amino acid residue sequence of any of FIGS. 1–5 (corresponding to SEQ ID NOs: 17, 19, 21, 23 and 25, respectively). More preferably, an expression vector of the present invention comprises a polynucleotide comprising the nucleotide base sequence of any of FIGS. 1–5 (SEQ ID NOs: 16, 18, 20, 22, 24, respectively). Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes a biologically active MAT II β subunit polypeptide in accordance with the present invention. FIGS. 1–5 and 6 (SEQ ID NOs: 16–25 and 1, respectively) set forth nucleotide and amino acid sequences from exemplary vertebrate, human. Also provided by the present invention are homologous or biologically equivalent polynucleotides and MAT II β subunit polypeptides found in other vertebrates, including particularly rat, bovine and murine homologs. Preferably, a recombinant host cell of the present invention is transfected with the polynucleotide that encodes human MAT II β subunit polypeptide. More preferably, a recombinant host cell of the present invention is transfected with the polynucleotide sequence of any of FIGS. 1–5 and 6 (SEQ ID NOs: 16, 18, 20, 22, 24 and 1, respectively). Even more preferably, a host cell of the invention is a eukaryotic host cell. Still more preferably, a recombinant host cell of the present invention is a vertebrate cell. Preferably, a recombinant host cell of the invention is a mammalian cell.

In another aspect, a recombinant host cell of the present invention is a prokaryotic host cell, including parasitic and bacterial cells. Preferably, a recombinant host cell of the invention is a bacterial cell, preferably a strain of *Escherichia coli*. More preferably, a recombinant host cell comprises a polynucleotide under the transcriptional control of regulatory signals functional in the recombinant host cell, wherein the regulatory signals appropriately control expression of the MAT II β subunit polypeptide in a manner to enable all necessary transcriptional and post-transcriptional modification.

In yet another embodiment, the present invention provides a process of preparing a MAT II β subunit polypeptide comprising transfecting a cell with polynucleotide that encodes a biologically active MAT II β subunit polypeptide in accordance with the present invention, to produce a transformed host cell; and maintaining the transformed host cell under biological conditions sufficient for expression of the polypeptide. More preferably, the transformed host cell is a eukaryotic cell. More preferably still, the eukaryotic cell is a vertebrate cell. Alternatively, the host cell is a prokaryotic cell. More preferably, the prokaryotic cell is a bacterial cell of *Escherichia coli*. Even more preferably, a polynucleotide transfected into the transformed cell comprises the nucleotide base sequence of any of FIGS. 1–5 and 6 (SEQ ID NOs: 16, 18, 20, 22, 24 and 1, respectively). FIGS. 1–5 and 6 (SEQ ID NOs: 16–25 and 1, respectively) set forth nucleotide and amino acid sequences for exemplary vertebrate, human. Also provided by the present invention are homologues or biologically equivalent MAT II β subunit polynucleotides and polypeptides found in other vertebrates, particularly warm blooded vertebrates, more particularly mammals, and even more particularly bovine and murine homologs.

As mentioned above, in connection with expression embodiments to prepare recombinant MAT II β subunit proteins and peptides, it is provided that longer DNA segments will most often be used, with DNA segments encoding the entire MAT II β subunit protein, functional domains or cleavage products thereof, being most preferred. However, it will be appreciated that the use of shorter DNA segments to direct the expression of MAT II β subunit peptides or epitopic core regions, such as can be used to generate anti-MAT II β subunit antibodies, also falls within the scope of the invention.

DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full length proteins can have a minimum coding length on the order of about 4,000 nucleotides for a protein in accordance with any of FIGS. 1–5 (SEQ ID NOs: 17, 19, 21, 23 and 25).

Naturally, the present invention also encompasses DNA segments which are complementary, or essentially complementary, to the sequences set forth in any of FIGS. 1–5 and 6 (SEQ ID NOs: 16, 18, 20, 22, 24 and 1, respectively). The terms "complementary" and "essentially complementary" are defined above. Excepting intronic or flanking regions, and allowing for the degeneracy of the genetic code, sequences which have between about 70% and about 80%; or more preferably, between about 81% and about 90%; or even more preferably, between about 91% and about 99%; of nucleotides which are identical or functionally equivalent (i.e. encoding the same amino acid) of nucleotides of any of FIGS. 1–6 (SEQ ID NOs: 16, 18, 20, 22, 24 and 1, respectively), will be sequences which are "a sequence essentially as set forth in any of FIGS. 1–6". Sequences which are essentially the same as those set forth in any of FIGS. 1–5 and 6 (SEQ ID NOs: 16, 18, 20, 22, 24 and 1, respectively) can also be functionally defined as sequences which are capable of hybridizing to a nucleic acid segment containing the complement of any of FIGS. 1–5 and 6 (SEQ ID NOs: 16, 18, 20, 22, 24 and 1, respectively) under relatively stringent conditions. Suitable relatively stringent hybridization conditions are described herein and will be well known to those of skill in the art.

A.3. Biologically Functional Equivalents

As mentioned above, modification and changes can be made in the structure of the MAT II β subunit proteins and peptides described herein and still obtain a molecule having like or otherwise desirable characteristics. For example, certain amino acids can be substituted for other amino acids in a protein structure without appreciable loss of interactive capacity with structures such as, for example, in the nucleus of a cell. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated in accordance with the present invention that various changes can be made in the sequence of the MAT II β subunit proteins and peptides (or underlying DNA) without appreciable loss of their biological utility or activity.

It is also well understood by the skilled artisan that, inherent in the definition of a biologically functional equivalent protein or peptide, is the concept that there is a limit to the number of changes that can be made within a defined portion of the molecule and still result in a molecule with an acceptable level of equivalent biological activity. Biologically functional equivalent peptides are thus defined herein as those peptides in which certain, not most or all, of the amino acids can be substituted. Of course, a plurality of distinct proteins/peptides with different substitutions can easily be made and used in accordance with the invention.

It is also well understood that where certain residues are shown to be particularly important to the biological or structural properties of a protein or peptide, e.g., residues in active sites, such residues can not generally be exchanged. This is the case in the present invention, where if any changes, for example, in the functional domain of MAT II β subunit polypeptides, could result in a loss of an aspect of the utility of the resulting peptide for the present invention.

Amino acid substitutions, such as those which might be employed in modifying the MAT II β subunit proteins and peptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those which are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those which are within ±1 of the original value are particularly preferred, and those within ±0.5 of the original value are even more particularly preferred.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

A.4. Sequence Modification Techniques

Modifications to the MAT II β subunit proteins and peptides described herein can be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucleotides in length is preferred, with about 5 to 10 residues on both sides of the junction of the sequence being altered.

In general, the technique of site-specific mutagenesis is well known in the art as exemplified by publications (e.g., Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes, for example, a human MAT II β subunit polypeptide. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected gene using site-directed mutagenesis is provided as a means of producing potentially useful MAT II β subunit polypeptide or other species capable of modulating MAT II biological activity and is not meant to be limiting as there are other ways in which sequence variants of these peptides can be obtained. For example, recombinant vectors encoding the desired genes can be treated with mutagenic agents to obtain sequence variants (see, e.g., a method described by Eichenlaub, 1979) for the mutagenesis of plasmid DNA using hydroxylamine.

A.5. Other Structural Equivalents

In addition to the MAT II β subunit peptidyl compounds described herein, the inventors also provide that other sterically similar compounds can be formulated to mimic the key portions of the peptide structure. Such compounds can be used in the same manner as the peptides of the invention and hence are also functional equivalents. The generation of a structural functional equivalent can be achieved by the techniques of modeling and chemical design known to those of skill in the art. It will be understood that all such sterically similar constructs fall within the scope of the present invention.

The knowledge of the structure of the MAT II β subunit polypeptide of the present invention, provides a means of investigating the mechanism of action of these proteins in a subject. For example, binding of these proteins to various substrate molecules can be predicted by various computer models. Upon discovering that such binding in fact takes place, knowledge of the protein structure then allows chemists to design and attempt to synthesize small molecules which mimic the functional binding of the MAT II β subunit polypeptide to the substrate. This is the method of "rational" drug design.

Use of the isolated and purified MAT II β subunit polypeptide of the present invention in rational drug design is thus provided in accordance with the present invention. Additional rational drug design techniques are described in U.S. Pat. Nos. 5,834,228 and 5,872,011, the entire contents of which are herein incorporated by reference.

B. Introduction of Gene Products

Where the gene itself is employed to introduce the gene products, a convenient method of introduction will be through the use of a recombinant vector which incorporates the desired gene, together with its associated control sequences. The preparation of recombinant vectors is well known to those of skill in the art and described in many references, such as, for example, Sambrook et al. (1989), specifically incorporated herein by reference.

B.1. Vector Construction

In vectors, it is understood that the DNA coding sequences to be expressed, in this case those encoding the MAT II β subunit gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of the chosen promoter. One can also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the specific gene (i.e., a MAT II β subunit promoter as set forth in FIG. 6 for a MAT II β subunit gene) will be preferred, there is no reason why other control sequences could not be employed, so long as they are compatible with the genotype of the cell being treated. Thus, one can mention other useful promoters by way of example, including, e.g., an SV40 early promoter, a long terminal repeat promoter from retrovirus, an actin promoter, a heat shock promoter, a metallothionein promoter, and the like.

As is known in the art, a promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent interalia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

For introduction of, for example, the human MAT II β subunit gene, it is proposed that one will desire to preferably employ a vector construct that will deliver the desired gene to the affected cells. This will, of course, generally require that the construct be delivered to the targeted cells, for example, cancer cells. It is proposed that this can be achieved most preferably by introduction of the desired gene through the use of a viral vector to carry the MAT II β subunit sequence to efficiently infect the cells. These vectors will preferably be an adenoviral, a retroviral, a vaccinia viral vector, adeno-associated virus or Lenti virus. These vectors are preferred because they have been successfully used to deliver desired sequences to cells and tend to have a high infection efficiency. Suitable vector-MAT II β subunit gene constructs are adapted for administration as pharmaceutical compositions, as described herein below.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments can also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication can be provided either by construction of the vector to include an exogenous origin, such as can be derived from SV40 or other viral (e.g., Polyoma, Adeno, VSV, BPV) source, or can be provided by the host cell chromosomal replication mechanism. If the vector is integrated into the host cell chromosome, the latter is often sufficient.

Where a MAT II β subunit gene itself is employed it will be most convenient to simply use a wild type MAT II β subunit gene directly. However, it is contemplated that certain regions of a MAT II β subunit gene can be employed exclusively without employing an entire wild type MAT II β subunit gene. It is proposed that it will ultimately be preferable to employ the smallest region needed to modulate MAT II biological activity so that one is not introducing unnecessary DNA into cells which receive a MAT II β subunit gene construct. Techniques well known to those of skill in the art, such as the use of restriction enzymes, will allow for the generation of small regions of an exemplary MAT II β subunit gene. The ability of these regions to modulate cell signaling can easily be determined by the assays reported in the Examples. In general, techniques for assessing the modulation of MAT II activity are known in the art.

B.2. Transgenic Animals

It is also contemplated to be within the scope of the present invention to prepare a transgenic non-human animal which expresses a MAT II β subunit gene of the present invention. A preferred transgenic animal is a mouse.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S.

Pat. No. 5,741,957 (transgenic bovine species), the entire contents of each of which are herein incorporated by reference.

With respect to an exemplary method for the preparation of a transgenic mouse, cloned recombinant or synthetic DNA sequences or DNA segments encoding a MAT II β subunit gene product are injected into fertilized mouse eggs. The injected eggs are implanted in pseudo pregnant females and are grown to term to provide transgenic mice whose cells express a MAT II β subunit gene product. Preferably, the injected sequences are constructed having promoter sequences connected so as to express the desired protein in all nucleated cells or specifically, in lymphocytes (both T and B) of the transgenic mouse.

Additionally, a genetically modified animal of the present invention can comprise an animal with targeted modification of the MAT II β subunit gene. Animal strains with complete or partial functional inactivation of a MAT II β subunit gene are generated using standard techniques of site-specific recombination in embryonic stem cells. Capecchi, M. R. (1989) *Science* 244(4910):1288–92; Thomas, K. R., and Capecchi, M. R. (1990) *Nature* 346(6287):847–50; Delpire, E., et al. (1999) *Nat Genet* 22(2):192–5. Procedures analogous to those employed in the generation of a "knock-out" animal can be applied in the generation of a "knock-out" cell line.

Alternatives include the use of anti-sense or ribozyme MAT II β subunit constructs, driven by a universal or tissue-specific promoter, to reduce levels of a MAT II β subunit in tissues, thus achieving a "knock-down" of individual isoforms (Luyckx, V. A., et al. (1999) *Proc Natl Acad Sci USA* 96(21):12174–9). The invention also provides the generation of animal strains with conditional or inducible inactivation of individual or multiple MAT II β subunit genes (Sauer, B. (1998) *Methods* 14(4):381–92; Ding, Y., et al. (1997) *J Biol Chem* 272(44):28142–8).

The present invention also provides animal strains with specific "knocked-in" modifications in a MAT II β subunit gene. This includes animals with genetically (Forlino, A., et al. (1999) *J Biol Chem* 274(53):37923–31) and functionally (Kissel, H., et al. (2000) *Embo J* 19(6):1312–1326) relevant point mutations in the MAT II β subunit gene, in addition to manipulations such as the insertion of disease-specific repeat expansions (White, J. K., et al. (1997) *Nat Genet* 17(4):404–10).

C. Pharmaceutical Compositions

In a preferred embodiment, the present invention provides pharmaceutical compositions comprising a polypeptide or polynucleotide of the present invention and a physiologically acceptable carrier. More preferably, a pharmaceutical composition comprises a MAT II β subunit polypeptide or a polynucleotide that encodes those polypeptides.

A composition of the present invention is typically administered parenterally in dosage unit formulations containing standard, well-known nontoxic physiologically acceptable carriers, adjuvants, and vehicles as desired. The term "parenteral" as used herein includes intravenous, intramuscular, intra-arterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A transfected cell can also serve as a carrier. By way of example, a liver cell can be removed from an organism, transfected with a polynucleotide of the present invention using methods set forth above and then the transfected cell returned to the organism (e.g. injected intra-vascularly).

D. Generation of Antibodies

In still another embodiment, the present invention provides an antibody immunoreactive with a polypeptide of the present invention. Preferably, an antibody of the invention is a monoclonal antibody. Means for preparing and characterizing antibodies are well known in the art (See, e.g., *Antibodies A Laboratory Manual*, E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies. The production of polyclonal antibodies to the MAT II β subunit is also described in the Examples appended hereto.

As is well known in the art, a given polypeptide or polynucleotide can vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies, inter alia, upon the nature of the immunogen as well as the animal used for immunization. A variety of routes can be used to administer the immunogen, e.g. subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention provides a process of producing an antibody immunoreactive with a MAT II β subunit polypeptide, the process comprising the steps of (a) transfecting recombinant host cells with a polynucleotide that encodes that polypeptide; (b) culturing the host cells under conditions sufficient for expression of the polypeptide; (c) recovering the polypeptide; and (d) preparing antibodies to the polypeptide. Preferably, the MAT II β subunit polypeptide is capable of modulating MAT II biological activity in accordance with the present invention. Even more preferably, the present invention provides antibodies prepared according to the process described above.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immuno-specific reaction with the bound antibody. The polypeptide or polynucleotide is then easily removed from the substrate and purified.

E. Screening Assays

In yet another aspect, the present invention provides a process of screening substances for their ability to affect or modulate the biological activity of MAT II β subunit gene products or of MAT II, and for their ability to affect or modulate in vivo MAT II β subunit levels. The present invention also provides a process of screening substances for their ability to affect or modulate the biological activity of MAT II β subunit gene products, and for their ability to affect or modulate in vivo MAT II β subunit levels, to thereby affect or modulate the biological activity of MAT II and/or levels of S-adenosylmethionine (AdoMet), particularly in cancer cells and activated alloreactive or autoreactive lymphocytes. This modulation can affect cell growth and differentiation.

Utilizing the methods and compositions of the present invention, screening assays for the testing of candidate substances are derived. A candidate substance is a substance which potentially can promote or inhibit the biological activity of gene product by binding, or other intermolecular interaction, with the MAT II β subunit gene product or with MAT II or with the MAT II α2 subunit gene product, and/or is a substance which potentially can increase or decease in vivo MAT II β subunit levels by binding, or other intermolecular interaction, with the MAT II β subunit gene or promoter region thereof.

E.1. Method of Screening for Modulators of MAT II β Biological Activity

An exemplary method of screening candidate substances for their ability to modulate MAT II β subunit biological activity comprises the steps of: (a) establishing replicate test and control samples that comprise a biologically active MAT II β subunit polypeptide; (b) administering a candidate substance to test sample but not the control sample; (c) measuring the biological activity of the MAT II β subunit polypeptide in the test and the control samples; and (d) determining that the candidate substance modulates MAT II β subunit biological activity if the biological activity of the MAT II β subunit polypeptide measured for the test sample is greater or less than the biological activity of the MAT II β subunit polypeptide measured for the control sample. The biological activities of MAT II β subunit that can optionally be examined in connection with a screening assay of the present invention comprise modulating the biological activity of MAT II, or other biological activity in accordance with the present invention.

The replicate test and control samples can further comprise a cell that expresses a biologically active MAT II β subunit polypeptide. The present invention also provides a recombinant cell line suitable for use in the exemplary method. A candidate substance identified according to the screening assay described herein has the ability to modulate MAT II β subunit biological activity. Such as candidate compound has utility in the treatment of disorders and conditions associated with the biological activity of MAT II β subunit.

In a cell-free system, the method comprises the steps of establishing a control system comprising a MAT II β subunit polypeptide and a ligand wherein the MAT II β subunit polypeptide is capable of binding to the ligand; establishing a test system comprising the MAT II β subunit polypeptide, the ligand, and a candidate compound; measuring the binding affinity of the MAT II β subunit polypeptide and the ligand in the control and the test systems; and determining that the candidate compound modulates MAT II β subunit activity in a cell-free system if the binding affinity measured for the test system is less than or greater than the binding affinity measured for the control system. An exemplary ligand comprises a monoclonal antibody and/or MAT II and/or α2 subunit of MAT II.

A screening assay of the present invention can also involve determining the ability of a candidate substance to modulate, i.e. inhibit or promote MAT II β subunit biological activity and preferably to thereby modulate the biological activity of MAT II in target cells. Target cells can be either naturally occurring cells known to contain a polypeptide of the present invention or transformed cell produced in accordance with a process of transformation set forth hereinbefore.

As is well known in the art, a screening assay provides a cell under conditions suitable for testing the modulation of MAT II β subunit biological activity, MAT II biological activity and/or levels of S-adenosylmethonine (AdoMet). These conditions include but are not limited to pH, temperature, tonicity, the presence of relevant metabolic factors (e.g., metal ions such as for example $Ca^{++}$, growth factor, interleukins, or colony stimulating factors), and relevant modifications to the polypeptide such as glycosylation or prenylation. A polypeptide of the present invention can be expressed and utilized in a prokaryotic or eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell.

In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of factors can be required for the proper testing of MAT II β subunit biological activity, MAT II biological activity and/or levels of S-adenosylmethionine (AdoMet) in specific cells. Such factors include, for example, the presence and absence (withdrawal) of growth factor, interleukins, or colony stimulating factors. U.S. Pat. Nos. 5,837,479; 5,645,999; 5,786,152; 5,739,278; and 5,352,660 also describe exemplary screening assays, and the entire contents of each are herein incorporated by reference.

Another technique for drug screening which can be used provides for high throughput screening of compounds having suitable binding affinity to the protein of interest as described in published PCT application WO 84/03564, herein incorporated by reference. In this method, as applied to a polypeptide of the present invention, large numbers of different small test compounds are synthesized on a solid substrate, such as plastic pins or some other surface. The test compounds are reacted with the polypeptide, or fragments thereof, and washed. Bound polypeptide is then detected by methods well known in the art. The purified polypeptide can also be coated directly onto plates for use in the aforementioned drug screening techniques. Alternatively, non-neutralizing antibodies can be used to capture the peptide and immobilize it on a solid support.

In one embodiment, a method of screening for a modulator of a MAT II β subunit polypeptide comprises: providing cells from a cDNA expression library on a substrate, the cells comprising cDNA coding for the MAT II β subunit polypeptide; causing protein synthesis by the cells; subjecting the cells to a library of test samples; detecting an interaction between a test sample and a cell expressing the MAT II β subunit polypeptide; identifying a test sample that interacts with a cell expressing the MAT II β subunit polypeptide; and isolating the test sample that interacts with the MAT II β subunit polypeptide. In this method, cells can be derived from a prokaryote or a eukaryote, including *Homo sapiens*.

In another embodiment, a method of screening for a modulator of a MAT II β subunit polypeptide comprises: affixing distinct colonies of cells from a cDNA expression library on a substrate, the cells comprising cDNA coding for the MAT II β subunit polypeptide; causing protein synthesis by said colonies on the substrate; subjecting the colonies of cells to a library of test samples; detecting an interaction between a test sample and a cell expressing the MAT II β subunit polypeptide; identifying a test sample that interacts with a cell expressing a MAT II β subunit polypeptide; and isolating a test sample that interacts with a MAT II β subunit polypeptide. In this method, the cells can also be derived from a prokaryote or a eukaryote, including *Homo sapiens*.

In yet another embodiment, a method of screening for a modulator of a MAT II β subunit polypeptide encoded comprises: providing a library of test samples; contacting a MAT II β subunit polypeptide with each test sample; detecting an interaction between a test sample and a MAT II β subunit polypeptide; identifying a test sample that interacts with a MAT II β subunit polypeptide; and isolating a test sample that interacts with a MAT II β subunit polypeptide.

In each of the foregoing embodiments, an interaction can be detected spectrophotometrically, radiologically or immunologically. An interaction between the MAT II β subunit polypeptide and a test sample can also be quantified. Such an interaction can be quantified by determining MAT II β subunit activity.

In still another embodiment, a screening assay is designed to be capable of discriminating candidate substances having selective ability to interact with one or more of the polypeptides of the present invention but which polypeptides are without a substantially overlapping activity with another of those polypeptides identified herein. Exemplary assays including genetic screening assays and molecular biology screens such as a yeast two-hybrid screen which will effectively identify MAT II-interacting genes important for cell growth and differentiation division or other MAT II-mediated cellular process. One version of the yeast two-hybrid system has been described (Chien et al., 1991, *Proc. Natl. Acad. Sci. USA*, 88:9578–9582) and is commercially available from Clontech (Palo Alto, Calif.).

A method of identifying modulators of the MAT II β subunit by rational drug design is provided in accordance with the present invention. The method comprising the steps of designing a potential modulator for a MAT II β subunit that will form non-covalent bonds with amino acids in the MAT II β subunit substrate binding site based upon the structure of a MAT II β subunit polypeptide; synthesizing the modulator; and determining whether the potential modulator modulates the activity of a MAT II β subunit. Modulators are synthesized using techniques disclosed herein and as are known in the art. The determination of whether the modulator modulates the biological activity of a MAT II β subunit is made in accordance with the screening methods disclosed herein.

E.2 Method of Screening for Modulators of In Vivo MAT II β Subunit Levels

In accordance with the present invention there are also provided methods for screening candidate compounds for the ability to modulate in vivo MAT II β subunit levels. Exemplary modulators of MAT II β subunit levels can thus comprise modulators of MAT II β subunit expression. Pharmaceuticals which increase or decrease the expression of MAT II β subunit-encoding genes have important clinical application for the modulation of the biological activity of MAT II and/or levels of S-adenosylmethionine (AdoMet), particularly in cancer cells and activated alloreactive or autoreactive lymphocytes. This modulation can affect cell growth and differentiation.

This invention thus includes a method for discovery of compounds which modulate the expression of MAT II β subunit-encoding genes and describes the use of such compounds. The general approach is to screen compound libraries for substances which increase or decrease expression of MAT II β subunit encoding genes. Exemplary techniques are described in U.S. Pat. Nos. 5,846,720 and 5,580,722, the entire contents of each of which are herein incorporated by reference.

While the following terms are believed to be well understood by one of skill in the art, the following definitions are set forth to facilitate explanation of the invention.

"Antisense nucleic acid" means an RNA or DNA molecule or a chemically modified RNA or DNA molecule which is complementary to a sequence present within an RNA transcript of a gene.

"Directly transcriptionally modulate the expression of a gene" means to transcriptionally modulate the expression of the gene through the binding of a molecule to (a) the gene, (b) an RNA transcript of the gene, or (c) a protein which binds to (i) such gene or RNA transcripts, or (ii) a protein which binds to such gene or RNA transcript.

A "gene" means a nucleic acid molecule, the sequence of which includes all the information required for the normal regulated production of a particular protein, including the structural coding sequence, promoters and enhancers.

"Indirectly transcriptionally modulate the expression of a gene" means to transcriptionally modulate the expression of such gene through the action of a molecule which cause enzymatic modification of a protein which binds to (a) the gene or (b) an RNA transcript of the gene, or (c) protein which binds to (i) the gene or (ii) an RNA transcript of the gene. For example, altering the activity of a kinase which subsequently phosphorylates and alters the activity of a transcription factor constitutes indirect transcript modulation.

"Ligand" means any binding molecule, and here particularly refers to a molecule which binds to a transcription factor for a gene. The binding of the ligand to the transcription factor transcriptionally modulates the expression of the gene.

"Ligand binding domain of a transcription factor" means the site on the transcription factor at which the ligand binds.

"Modulatable transcriptional regulatory sequence of a gene" means a nucleic acid sequence within the gene to which a transcription factor binds so as to transcriptionally modulate the expression of the gene.

"Receptor" means a transcription factor containing a ligand binding domain.

"Specifically transcriptionally modulate the expression of a gene" means to transcriptionally modulate the expression of such gene alone, or together with a limited number of other genes.

"Transcription" means a cellular process involving the interaction of an RNA polymerase with a gene which directs the expression as RNA of the structural information present in the coding sequences of the gene. The process includes, but is not limited to the following steps: (a) the transcription initiation, (b) transcript elongation, (c) transcript splicing, (d) transcript capping, (e) transcript termination, (f) transcript polyadenylation, (g) nuclear export of the transcript, (h) transcript editing, and (i) stabilizing the transcript.

"Transcription factor for a gene" means a cytoplasmic or nuclear protein which binds to (a) such gene, (b) an RNA transcript of such gene, or (c) a protein which binds to (i) such gene or such RNA transcript or (ii) a protein which binds to such gene or such RNA transcript, so as to thereby transcriptionally modulate expression of the gene.

"Transcriptionally modulate the expression of a gene" means to change the rate of transcription of such gene.

"Triple helix" means a helical structure resulting from the binding of one or more oligonucleotides to double stranded DNA.

In accordance with the present invention there is provided a method of identifying a candidate compound or molecule that is capable of transcriptionally modulating the expression of a gene encoding MAT II β subunit, and thus is capable of acting as a therapeutic agent in the modulation of MAT II β subunit levels, to thereby affect or modulate the biological activity of MAT II and/or levels of S-adenosylmethonine (AdoMet), particularly in cancer cells and activated alloreactive or autoreactive lymphocytes. This modulation can affect cell growth and differentiation.

This method comprises contacting a sample which contains a predefined number of cells with a predetermined amount of candidate compound or molecule to be tested. Each such cell comprises DNA comprising (i) a modulatable transcriptional regulatory sequence of a MAT II β subunit gene, (ii) a promoter of a MAT II β subunit gene, and (iii) a DNA sequence encoding a polypeptide other than MAT II β subunit, which polypeptide being capable of producing a detectable signal. Thus, the polypeptide can be described as a reporter or marker polypeptide. Preferably, the candidate compound directly and specifically transcriptionally modulates expression of the MAT II β subunit-encoding gene.

The DNA sequence is coupled to and under the control of the promoter, under conditions such that the candidate compound or molecule, if capable of acting as a transcriptional modulator of the gene encoding MAT II β subunit, causes a measurable detectable signal to be produced by the polypeptide so expressed. This allows for quantitative determination of the amount of the signal produced. By comparing the amount so determined with the amount of produced signal detected in the absence of any molecule being tested or upon contacting the sample with any other molecule, this method allows one to identify the candidate compound or molecule as one which causes a change in the detectable signal produced by the polypeptide so expressed, and thus identifying the molecule as a molecule capable of transcriptionally modulating the expression of the gene encoding MAT II β subunit, to thereby identify the candidate compound as a therapeutic agent in the modulation of MAT II β subunit levels, to thereby affect or modulate the biological activity of MAT II and/or levels of S-adenosylmethonine (AdoMet), particularly in cancer cells and activated alloreactive or autoreactive lymphocytes. This modulation can affect cell growth and differentiation.

In the practice of the preceding method the reporter polypeptide can be a luciferase, chloramphenicol acetyltransferase, β-glucuronidase, β-galactosidase, neomycin phosphotransferase, alkaline phosphatase or guanine xanthine phosphoribosyltransferase or a natually fluorescent protein (e.g. green fluorescent protein).

This invention still further provides a method of determining whether a candidate compound or molecule is capable of directly and specifically transcriptionally modulating the expression of a gene encoding a MAT II β subunit. This method comprises contacting a sample which contains a predefined number of cells with a predetermined amount of a candidate compound or molecule to be tested. Each such cell comprises DNA comprising (i) a modulatable transcriptional regulatory sequence of the gene encoding MAT II β subunit, (ii) a promoter of the gene encoding MAT II β subunit (exemplified in FIG. 6) (SEQ ID NO:1), and (iii) a reporter gene, which expresses a polypeptide.

The reporter gene is coupled to and under the control of the promoter, under conditions such that the candidate compound or molecule, if capable of acting as a transcriptional modulator of the gene encoding MAT II β subunit, causes a measurable detectable signal to be produced by the polypeptide so expressed. This allows for quantitative determination of the amount of the signal produced. By comparing the amount so determined with the amount of produced signal detected in the absence of any molecule being tested or upon contacting the sample with any other molecule, this method allows one to identify the candidate compound or molecule as one which causes a change in the detectable signal produced by the polypeptide so expressed, and thus identifying the molecule as a molecule capable of directly and specifically transcriptionally modulating the expression of the gene encoding MAT II β subunit, to thereby identify the candidate compound as a therapeutic agent in the modulation of MAT II β subunit levels, to thereby affect or modulate the biological activity of MAT II and/or levels of S-adenosylmethonine (AdoMet), particularly in cancer cells and activated alloreactive or autoreactive lymphocytes. This modulation can affect cell growth and differentiation.

In the foregoing methods the DNA sequence encoding the polypeptide can be inserted downstream of the promoter of the gene encoding MAT II β subunit by homologous recombination. In certain embodiments of the invention the polypeptide so produced is capable of complexing with an antibody or is capable of complexing with biotin. In this case the resulting complexes can be detected.

Another method of determining whether a candidate compound or molecule is capable of transcriptionally modulating the expression of a gene encoding MAT II β subunit is provided in accordance with the present invention. This method comprises contacting a sample which contains a predefined number of cells with a predetermined amount of a candidate compound or molecule to be tested. Each such cell comprises DNA comprising (i) a modulatable transcriptional regulatory sequence of the gene encoding MAT II β subunit, (ii) a promoter of the gene encoding MAT II β subunit (exemplified in FIG. 6)(SEQ ID NO:1), and (iii) a DNA sequence transcribable into mRNA coupled to and under the control of the promoter. The contacting is under conditions such that the candidate compound or molecule, if capable of acting as a transcriptional modulator of the protein of interest, causes a measurable difference in the amount of mRNA transcribed from the DNA sequence.

This method allows for the quantitative determination of the amount of the mRNA produced. By comparing the amount so determined with the amount of mRNA detected in the absence of any molecule being tested or upon contacting the sample with any other molecule, one can thereby identify the candidate compound or molecule as one which causes a change in the detectable mRNA amount of, and thus identifying the molecule as a molecule capable of directly and specifically transcriptionally modulating the expression of the gene encoding MAT II β subunit. Such a compound is thereby identified as a therapeutic agent in the modulation of MAT II β subunit levels, to thereby affect or modulate the biological activity of MAT II and/or levels of S-adenosylmethonine (AdoMet), particularly in cancer cells and activated alloreactive or autoreactive lymphocytes. This modulation can affect cell growth and differentiation. The mRNA is optionally detected by quantitative polymerase chain reaction, Northern blot analysis or by any other method as would be apparent to one of skill in the art.

In each of the preceding methods the sample comprises cells in monolayers or cells in suspension. Preferably, such cells are animal cells or human cells. In the presently preferred method the predefined number of cells is from about 1 to about $5 \times 10^5$ cells, or about $2 \times 10^2$ to about $5 \times 10^4$ cells. In these methods the predetermined amount or concentration of the molecule to be tested is typically based upon the volume of the sample, or be from about 1.0 pM to about 20 $\mu$M, or from about 10 nM to about 500 $\mu$M.

Typically the contacting is effected from about 1 to about 24 hours, preferably from about 2 to about 12 hours. Also the contacting is typically effected with more than one predetermined amount of the molecule to be tested. The molecule to be tested in these methods can be a purified molecule or a homogenous sample. Further, in the method of the invention, the DNA is the cell can comprise, or can consist essentially of, more than one modulatable transcriptional regulatory sequence.

In accordance with the present invention there is also provided a rapid and high throughput screening method which relies on the methods described above. This screening method comprises separately contacting each of a plurality of substantially identical samples, each sample containing a predefined number of cells under conditions such that contacting is affected with a predetermined amount of each different candidate compound or molecule to be tested. In such a screening method the plurality of samples preferably comprises more that about $10^4$ samples, or more preferably comprises more than about $5×10^4$ samples. Also provided is a method of essentially simultaneously screening candidate compounds or molecules to determine whether the molecules are capable of transcriptionally modulating one or more genes encoding a MAT II β subunit according to the methods discussed above. These methods are optionally carried out with more than about $10^3$ samples per week contacted with different candidate compounds or molecules.

E.3. Animal Models

In addition, animal-based systems can be used to identify compounds capable of modulating MAT II β subunit biological activity. Such animal models can be used as test substrates for the identification of drugs, pharmaceuticals, therapies, and interventions which can be effective in modulating MAT II β subunit biological activity. For example, animal models can be exposed to a compound, suspected of exhibiting an ability to modulate MAT II β subunit biological activity symptoms, at a sufficient concentration and for a time sufficient to elicit such modulation of MAT II β subunit biological activity symptoms in the exposed animals. The response of the animals to the exposure can be monitored by assessing cell growth and differentiation, and by assessing in vivo MAT II β subunit levels.

For example, given the presence of endogenous kinases and other modulators of transcription in an animal model, indirectly transcriptional modulation of the expression of a MAT II β subunit gene can be assessed. As described above, indirectly transcriptional modulation refers to transcriptional modulation the expression of such gene through the action of a molecule which cause enzymatic modification of a protein which binds to (a) the gene or (b) an RNA transcript of the gene, or (c) protein which binds to (i) the gene or (ii) an RNA transcript of the gene.

Indirect transcriptional modulation is evaluated through the administration of a candidate compound or molecule to an animal model. A biological sample is then obtained from the animal model and is analyzed for modulation of MAT II β subunit expression in accordance with the methods described above. A candidate compound which modulates MAT II β subunit expression in the animal model can then be tested as described above for direct and specific transcriptional modulation to confirm that indirect transcriptional modulation has occurred in the animal model.

With regard to intervention, any treatments which reverse any aspect of modulating MAT II β subunit-mediated biological activity (e.g. in the modulation of MAT II β subunit levels, to thereby affect or modulate the biological activity of MAT II and/or levels of S-adenosylmethonine (AdoMet), particularly in cancer cells and activated alloreactive or autoreactive lymphocytes. This modulation can affect cell growth and differentiation) should be considered as candidates for human therapeutic intervention in accordance with the methods described hereinbelow. Dosages of test agents can be determined by deriving dose-response curves, such as those disclosed in U.S. Pat. No. 5,849,578, herein incorporated by reference.

F. Therapeutic Methods

As used herein, the terms "MAT II β subunit activity" and "MAT II β subunit biological activity" are meant to be synonymous and are meant to refer to any biological activity of a MAT II β subunit polypeptide. Exemplary biological activities of MAT II β subunit comprise activity in the modulation of MAT II biological activity, modulation of levels of AdoMet, and modulation of cell growth, proliferation and/or differentiation, or other biological activity in accordance with the present invention.

The biological activity can be accomplished by endogenous MAT II β subunit polypeptides or by MAT II β subunit polypeptide administered to a subject. Indeed, an isolated and purified MAT II β subunit polypeptide, recombinant MAT II β subunit polypeptide, and/or MAT II β subunit analog or peptidomimetic, each prepared as described herein, can administered to a subject to impart MAT II β subunit biological activity in the subject and to treat a disorder associated with MAT II β subunit biological activity in the subject. In such case the imparted MAT II β subunit biological activity comprises a MAT II β subunit biological activity in accordance with the therapeutic methods of the present invention.

The modulated MAT II biological activity can comprise MAT II biological activity endogenous to the patient, or, given the interaction between the MAT II β subunit and MAT II from *E. coli* disclosed in the Examples, modulation of MAT II biological activity in bacterial, fungal or other parasitic cells to thereby treat infection of the subject by such organisms.

With respect to the therapeutic methods of the present invention, a preferred subject is a vertebrate subject. A preferred example of a vertebrate is a warm-blooded vertebrate. A preferred example of a warm-blooded vertebrate is a mammal. A preferred example of a mammal is a human. Additionally, as used herein and in the claims, the term "patient" is contemplated to include both human and animal patients, and thus, veterinary therapeutic uses are contemplated in accordance with the present invention.

Contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

F.1. Modulation of MAT II β Subunit Biological Activity

In one embodiment, a therapeutic method according to the present invention comprises administering to a subject a substance that inhibits or promotes MAT II β subunit biological activity. Such a substance can be identified according to the screening assay set forth above. The method comprises treating a vertebrate subject suffering from a disorder associated with or mediated by MAT II β subunit biological activity by administering to the patient an effective MAT II β subunit biological activity-modulating amount of a substance identified according to a screening assay described above. By the term "modulating", the substance can either promote or inhibit the biological activity of MAT II β subunit polypeptides, depending on the disorder to be treated. For example, the administering of antibodies against a chosen region of MAT II β subunit, the administering of a protein that enhances, or the administering of a protein that inhibits the transcription of the MAT II β subunit provides treatment of disorders caused by MAT II β subunit-mediated mechanisms, including immune response, autoimmune disorders, cancer and transplantation associated disorders.

Insofar as a MAT II β subunit biological activity modulator can take the form of a polypeptide or of an anti-MAT II β subunit monoclonal antibody, or fragment thereof, it is to be appreciated that the potency, and therefore an expression of a "therapeutically effective" amount can vary. However, as shown by the present assay methods, one skilled in the art can readily assess the potency of a candidate MAT II β subunit biological activity modulator of this invention. A MAT II β subunit biological activity modulator can be measured by a variety of means including through the use of a responsive reporter, which drives expression of a reporter gene; interaction of MAT II β subunit polypeptides with a monoclonal antibody as described herein; and the like assays.

A preferred MAT II β subunit biological activity modulator has the ability to substantially interact with MAT II β subunit in solution at modulator concentrations of less than one (1) micro molar ($\mu$M), preferably less than 0.1 $\mu$M, and more preferably less than 0.01 $\mu$M. By "substantially" is meant that at least a 50 percent modulation in MAT II β subunit biological activity is observed in the presence of the MAT II β subunit biological activity modulator, and a 50% modulation is referred to herein as an IC50 value.

A therapeutically effective amount of a MAT II β subunit biological activity modulator of this invention in the form of a monoclonal antibody, or fragment thereof, is typically an amount such that when administered in a physiologically tolerable composition is sufficient to achieve a plasma concentration of from about 0.01 microgram (ug) per milliliter (ml) to about 100 ug/ml, preferably from about 1 ug/ml to about 5 ug/ml, and usually about 5 ug/ml.

A therapeutically effective amount of a MAT II β subunit biological activity modulator of this invention in the form of a polypeptide is typically an amount of polypeptide such that when administered in a physiologically tolerable composition is sufficient to achieve a plasma concentration of from about 0.001 microgram ($\mu$g) per milliliter (ml) to about 10 $\mu$g/ml, preferably from about 0.05 $\mu$g/ml to about 1.0 ug/ml.

The monoclonal antibodies or polypeptides of the invention can be administered parenterally by injection or by gradual infusion over time. Although the tissue to be treated can typically be accessed in the body by systemic administration and therefore most often treated by intravenous administration of therapeutic compositions, other tissues and delivery means are provided where there is a likelihood that the tissue targeted contains the target molecule. Thus, monoclonal antibodies or polypeptides of the invention can be administered intravenously, intraperitoneally, intramuscularly, subcutaneously, intra-cavity, transdermally, and can be delivered by peristaltic means.

The therapeutic compositions containing a monoclonal antibody or a polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are provided. Polypeptide modulators can also be modified as described herein below with respect to biologically active MAT II β subunit proteins and protein therapy methods using the same.

F.2. Monoclonal Antibodies

The present invention describes, in one embodiment, MAT II β subunit modulators in the form of monoclonal antibodies which immunoreact with a MAT II β subunit polypeptide and bind the MAT II β subunit polypeptide to modulate biological activity as described herein. The invention also describes above cell lines which produce the antibodies, methods for producing the cell lines, and methods for producing the monoclonal antibodies.

The term "antibody or antibody molecule" in the various grammatical forms is used herein as a collective noun that refers to a population of immunoglobulin molecules and/or immunologically active portions of immunoglobulin molecules, i.e., molecules that contain an antibody combining site or paratope. An "antibody combining site" is that structural portion of an antibody molecule comprised of heavy and light chain variable and hypervariable regions that specifically binds antigen.

Exemplary antibodies for use in the present invention are intact immunoglobulin molecules, substantially intact immunoglobulin molecules, single chain immunoglobulins or antibodies, those portions of an immunoglobulin molecule that contain the paratope, including those portions known in the art as Fab, Fab', F(ab')2 and F(v), and also referred to as antibody fragments. Indeed, it is within the scope of the present invention that a monovalent modulator can optionally be is used in the present method. Thus, the terms "modulate", "modulating", and "modulator" are meant to be construed to encompass such promotion.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody can therefore contain an antibody molecule having a plurality of antibody combining sites, each immunospecific for a different epitope, e.g., a bispecific monoclonal antibody. Methods of producing a monoclonal antibody, a hybridoma cell, or a hybridoma cell culture are described above.

It is also possible to determine, without undue experimentation, if a monoclonal antibody has the same (i.e., equivalent) specificity (immunoreaction characteristics) as a monoclonal antibody of this invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the target molecule with which it is normally reactive, and then add the monoclonal antibody being tested to determine if the monoclonal antibody being tested is inhibited in its ability to bind the target molecule. If the monoclonal antibody being tested is inhibited then, in all likelihood, it has the same, or functionally equivalent, epitopic specificity as the monoclonal antibody of the invention.

An additional way to determine whether a monoclonal antibody has the specificity of a monoclonal antibody of the invention is to determine the amino acid residue sequence of the CDR regions of the antibodies in question. "CDRs" (complementarity determining regions) mean the three subregions of the light or heavy chain variable regions which have hypervariable sequences and form loop structures that are primarily responsible for making direct contact with antigen. Antibody molecules having identical, or functionally equivalent, amino acid residue sequences in their CDR regions have the same binding specificity. Methods for sequencing polypeptides are well known in the art.

The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin that comprises the antibody, and in part by the light chain variable region amino acid residue sequence. Use of the terms "having the binding specificity of" or "having the binding preference of" indicates that equivalent monoclonal antibodies exhibit the same or similar immunoreaction (binding) characteristics and compete for binding to a preselected target molecule.

Humanized monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention. Thus, the invention provides, in one embodiment, a monoclonal antibody of this invention that is humanized by grafting to introduce components of the human immune system without substantially interfering with the ability of the antibody to bind antigen.

The use of a molecular cloning approach to generate antibodies, particularly monoclonal antibodies, and more particularly single chain monoclonal antibodies, is also provided. The production of single chain antibodies has been described in the art, see e.g., U.S. Pat. No. 5,260,203, the contents of which are herein incorporated by reference. For this, combinatorial immunoglobulin phagemid libraries are prepared from RNA isolated from the spleen of the immunized animal, and phagemids expressing appropriate antibodies are selected by panning on endothelial tissue. The advantages of this approach over conventional hybridoma techniques are that approximately $10^4$ times as many antibodies can be produced and screened in a single round, and that new specificities are generated by H and L chain combination in a single chain, which further increases the chance of finding appropriate antibodies. Thus, an antibody of the present invention, or a "derivative" of an antibody of the present invention pertains to a single polypeptide chain binding molecule which has binding specificity and affinity substantially similar to the binding specificity and affinity of the light and heavy chain aggregate variable region of an antibody described herein.

F.3. Other Modulators

Given the disclosure of the MAT II β subunit activity in tissues herein, chemical compounds (e.g. small molecule mimetics) can be used to modulate MAT II β subunit activity in tissues in accordance with the methods of the present invention. The identification of such compounds is facilitated by the description of screening assays directed to MAT II β subunit activity in tissues presented above.

Such a candidate compound has utility in the treatment of disorders and conditions associated with the biological activity of a MAT II β subunit. Candidate compounds are typically about 500–1000 daltons, and can be hydrophobic, polycyclic, or both, molecules. Such compounds should be considered as candidates for therapeutic intervention in accordance with the methods described herein below. Thus, compounds identified via the screening methods of the present invention have application as agents for modulation of other biological events mediated by a MAT II β subunit. Dosages of test agents can be determined by deriving dose-response curves, such as those disclosed in U.S. Pat. No. 5,849,578, herein incorporated by reference.

F.4. Protein Therapy

In another embodiment, the direct introduction of the MAT II β subunit proteins into a tissue is provide to deliver a therapeutic effect in human and animals. Such a therapeutic method comprises administering to a patient a therapeutic composition which comprises a biologically active MAT II β subunit polypeptide of the present invention in amount effective to modulate MAT II biological activity and/or levels of S-adenosylmethionine (AdoMet). The modulated MAT II biological activity can comprise MAT II biological activity endogenous to the patient, or, given the interaction between the MAT II β subunit and MAT II from *E. coli* disclosed in the Examples, MAT II biological activity in bacterial, fungal or other parasitic cells to thereby treat infection of the patient by such organisms.

In one embodiment, a polypeptide for use in such a composition comprises no more than about 100 amino acid residues, preferably no more than about 60 residues, more preferably no more than about 30 residues. Peptides can be linear or cyclic.

A subject polypeptide includes any analog, fragment or chemical derivative of a MAT II β subunit polypeptide. Such a polypeptide can be subject to various changes, substitutions, insertions, and deletions where such changes provide for certain advantages in its use. In this regard, an MAT II β subunit polypeptide for use in a therapeutic method of the present invention corresponds to, rather than is identical to, the sequence of a native MAT II β subunit polypeptide where one or more changes are made and it retains the ability to function as a MAT II β subunit polypeptide in one or more of the assays as defined herein. Thus, a polypeptide can be in any of a variety of forms of peptide derivatives, that include amides, conjugates with proteins, cyclized peptides, polymerized peptides, analogs, fragments, chemically modified peptides, and the like derivatives.

The term "analog" includes any polypeptide having an amino acid residue sequence substantially identical to a sequence of an endogenous MAT II β subunit polypeptide in which one or more residues have been conservatively substituted with a functionally similar residue and which displays the MAT II β subunit biological activity as described herein. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another. Such substitutions are described in detail above with respect to the isolated and purified MAT II β subunit polypeptide of the present invention.

The phrase "conservative substitution" also includes the use of a chemically derivatized residue in place of a non-derivatized residue provided that such polypeptide displays the requisite biological activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as chemical derivatives are those peptides which contain one or more naturally occurring amino acid derivatives of the twenty standard amino acids. For examples: 4-hydroxyproline can be substituted for proline; 5-hydroxylysine can be substituted for lysine; 3-methylhistidine can be substituted for histidine; homoserine can be substituted for serine; and ornithine can be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of a MAT II β subunit endogenous polypeptide, it is typically because one or more conservative or non-conservative substitutions have been made, usually no more than about 30 number percent, and preferably no more than 10 number percent of the amino acid residues are substituted. Additional residues can also be added at either terminus of a polypeptide for the purpose of providing a "linker" by which the polypeptides of this invention can be conveniently affixed to a label or solid matrix, or carrier. Labels, solid matrices and carriers that can be used with the polypeptides of this invention are described elsewhere herein.

Amino acid residue linkers are usually at least one residue and can be 40 or more residues, more often 1 to 10 residues, but do not form MAT II β subunit polypeptide epitopes. Typical amino acid residues used for linking are tyrosine, cysteine, lysine, glutamic and aspartic acid, or the like. In addition, a subject polypeptide can differ, unless otherwise specified, from the natural sequence of a MAT II β subunit polypeptide by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases can be present. In this regard, polypeptide cyclization is also a useful terminal modification, and is particularly preferred also because of the stable structures formed by cyclization and in view of the biological activities observed for such cyclic peptides as described herein.

Any peptide of the present invention can be used in the form of a pharmaceutically acceptable salt. Suitable acids which are capable of the peptides with the peptides of the present invention include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl and TFA salts are particularly preferred.

Suitable bases capable of forming salts with the peptides of the present invention include inorganic bases such as sodium hydroxide, ammonium hydroxide, potassium hydroxide and the like; and organic bases such as mono- di- and tri-alkyl and aryl amines (e.g. triethylamine, diisopropyl amine, methyl amine, dimethyl amine and the like), and optionally substituted ethanolamines (e.g. ethanolamine, diethanolamine and the like).

A peptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis", W.H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, *Adv Enzymol*, 32:221–96,1969; Fields et al., *Int. J. Peptide Protein Res.*, 35:161–214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods provided comprise the sequential addition of one or more amino acid residues or suitably protected amino acid residues to a growing peptide chain. Normally, either the amino or carboxyl group of the first amino acid residue is protected by a suitable, selectively removable protecting group. a different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

The resultant linear polypeptides prepared for example as described above can be reacted to form their corresponding cyclic peptides. An exemplary method for cyclizing peptides is described by Zimmer et al., *Peptides* 1992, pp. 393–394, ESCOM Science Publishers, B. V., 1993. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

F.5. Gene Therapy

MAT II β subunit genes can be used for gene therapy in accordance with the present invention. Exemplary gene therapy methods, including liposomal transfection of nucleic acids into host cells, are described in U.S. Pat. Nos. 5,279,833; 5,286,634; 5,399,346; 5,646,008; 5,651,964; 5,641,484; and 5,643,567, the contents of each of which are herein incorporated by reference.

Briefly, gene therapy directed toward modulation of MAT II β subunit levels, to thereby affect or modulate the biological activity of MAT II and/or levels of S-adenosylmethionine (AdoMet), in a target cell is described. Target cells include, but are not limited to, cancer cells and activated alloreactive or autoreactive lymphocytes. This modulation can affect cell growth and differentiation. In one embodiment, a therapeutic method of the present invention provides a process for modulation of MAT II β subunit levels, to thereby affect or modulate the biological activity of MAT II and/or levels of S-adenosylmethionine (AdoMet) in a cell comprising the steps of: (a) delivering to the cell an effective amount of a DNA molecule comprising a polynucleotide that encodes a MAT II β subunit polypeptide that modulates the biological activity of MAT II and/or levels of S-adenosylmethionine (AdoMet); and (b) maintaining the cell under conditions sufficient for expression of said polypeptide.

In a preferred embodiment, the MAT II β subunit polypeptide is selected from any of FIGS. 1–5 (SEQ ID NOs: 17, 19, 21, 23 and 25). Delivery is preferably accomplished by injecting the DNA molecule into the cell. Where the cell is in a subject delivering is preferably administering the DNA molecule into the circulatory system of the subject. In a preferred embodiment, administering comprises the steps of: (a) providing a vehicle that contains the DNA molecule; and (b) administering the vehicle to the subject.

A vehicle is preferably a cell transformed or transfected with the DNA molecule or a transfected cell derived from such a transformed or transfected cell. An exemplary and preferred transformed or transfected cell is a lymphocyte or a tumor cell from the tumor being treated. Means for transforming or transfecting a cell with a DNA molecule of the present invention are set forth above.

Alternatively, the vehicle is a virus or an antibody that specifically infects or immunoreacts with an antigen of the tumor. Retroviruses used to deliver the constructs to the host target tissues generally are viruses in which the 3'-LTR (linear transfer region) has been inactivated. That is, these are enhancerless 3'-LTR's, often referred to as SIN (self-inactivating viruses) because after productive infection into the host cell, the 3'-LTR is transferred to the 5'-end and both viral LTR's are inactive with respect to transcriptional activity. A use of these viruses well known to those skilled in the art is to clone genes for which the regulatory elements of the cloned gene are inserted in the space between the two LTR's. An advantage of a viral infection system is that it allows for a very high level of infection into the appropriate recipient cell.

Antibodies have been used to target and deliver DNA molecules. An N-terminal modified poly-L-lysine (NPLL)-antibody conjugate readily forms a complex with plasmid DNA. A complex of monoclonal antibodies against a cell surface thrombomodulin conjugated with NPLL was used to target a foreign plasmid DNA to an antigen-expressing mouse lung endothelial cell line and mouse lung. Those targeted endothelial cells expressed the product encoded by that foreign DNA.

It is also envisioned that this embodiment of the present invention can be practiced using alternative viral or phage vectors, including retroviral vectors and vaccinia viruses whose genome has been manipulated in alternative ways so as to render the virus non-pathogenic. Methods for creating such a viral mutation are set forth in detail in U.S. Pat. No. 4,769,331, incorporated herein by reference.

FIG. 5.a. Gene Therapy Vector Construct Dosing

A nucleotide sequence of the present invention can be introduced into cells by introducing a virus containing a vector construct bearing the sequence of interest directly into a subject. This process requires the construction of a suitable vector. A suitable vector will contain the sequence of interest, as well as other functional sequences known to those skilled in the art to be required for viable transformation and transfection. A preferred procedure for alleviating a glucose transporter-related condition using a vector construct designed according to the described strategy is as follows.

The maximally tolerated dose (MTD) of vector construct when administered directly into the affected tissue is determined. Primary endpoints are: 1) the rate of transduction in abnormal and/or normal cells, 2) the presence and stability of this vector in the systemic circulation and in affected cells, and 3) the nature of the systemic (fever, myalgias) and local (infections, pain) toxicities induced by the vector. A secondary endpoint is the clinical efficacy of the vector construct.

For example, a 4 ml serum-free volume of viral (e.g. adenoviral, retroviral, etc.) vector construct (containing up to $5 \times 10^7$ viral particles in AIM V media) is administered daily per session. During each session, 1 ml of medium containing the appropriate titer of vector construct is injected into 4 regions of the affected tissue for a total of 4 ml per session in a clinical examination room. This is repeated daily for 4 days (4 sessions). This 16 ml total inoculum volume over 4 days is proportionally well below the one safely tolerated by nude mice (0.5 ml/20 g body weight).

Patient evaluation includes history and physical examination prior to initiation of therapy and daily during the 4-day period of vector construct injection. Toxicity grading is done using the ECOG Common Toxicity Criteria. CBC, SMA-20, urinalysis, and conventional studies are performed daily during this period. Evaluation will include a regular determination of the biological activity of MAT II and an assessment of the progression, if any, of, a condition that is treated.

F.5.b. Dose Escalation and MTD

Patients are treated with $3 \times 10^6$ viral particles×4. Once they have all recovered from all grade 2 or less toxicities (except alopecia), and as long as grade 3–4 toxicity is not encountered, a subsequent dose level is initiated in patients. As one grade 3 or 4 toxicity occurs at a given dose level, a minimum of 6 patients are enrolled at that level. As only 1 of 6 patients has grade 3 or 4 toxicity, dose escalation continues. The MTD of vector construct is defined as the dose where 2 of 6 patients experience grade 3 or 4 toxicity. If 2 of 3, or if 3 of 6 patients experience grade 3 or 4 toxicity, the MTD is defined as the immediately lower dose level.

The following escalation schema is followed: 1) level 1, $3 \times 10^6$ viral particles; 2) level 2, $1 \times 10^7$; 3) level 3, $3 \times 10^7$; 4) level 4, $5 \times 10^7$. Patients with measurable disease are evaluated for a clinical response to vector construct. Histology and local symptoms are followed.

F.6. Method of Modulating In Vivo MAT II β Subunit Levels in the Treatment of Modulate MAT II β Subunit Biological Activity A method for transcriptionally modulating in a multicellular organism the expression of a gene encoding MAT II β subunit to modulate MAT II β subunit biological activity in a vertebrate subject is also provided in accordance with the present invention. This method comprises administering to the vertebrate subject a compound at a concentration effective to transcriptionally modulate expression of MAT II β subunit to thereby modulate MAT II β subunit biological activity. Preferably, the provided method provides for elevated levels of MAT II β subunit by promoting expression of MAT II β subunit in the modulation of MAT II β subunit levels, to thereby affect or modulate the biological activity of MAT II and/or levels of S-adenosylmethionine (AdoMet), particularly in cancer cells and activated alloreactive or autoreactive lymphocytes. This modulation can affect cell growth and differentiation.

In this method the provided compound can optionally comprise an antibody or polypeptide prepared in accordance with the methods described above and which transcriptionally modulates expression of MAT II β subunit. Optionally, the antibody or polypeptide directly binds to DNA or RNA, or directly binds to a protein involved in transcription. Thus, indirect and direct transcriptional modulation are within the scope of the present method.

In an alternative embodiment of the present method the candidate compound does not naturally occur in the cell, specifically transcriptionally modulates expression of the gene encoding the protein of interest, and directly binds to DNA or RNA, or directly binds to a protein at a site on such protein which is not a ligand-binding domain of a receptor which naturally occurs in the cell. Preferably, the cell contacted in accordance with this method is a human cell.

Particular chemical entities (e.g. small molecule mimetics) do not naturally occur in any cell of a lower eucaryotic organism such as yeast. More particularly, the chemical entities do not naturally occur in any cell, whether of a multicellular or a unicellular organism. Even more particularly, the chemical entity is not a naturally occurring molecule, e.g. it is a chemically synthesized entity. Candidate chemical entities are typically about 500–1000 daltons, and can be hydrophobic, polycyclic, or both, molecules.

Optionally, the compound can bind to a modulatable transcription sequence of the gene. For example, the compound can bind to a promoter region upstream of a nucleic acid sequence encoding MAT II β subunit.

In the methods above, modulation of the transcription of MAT II β subunit results in either upregulation or downregulation of expression of the gene encoding the protein of interest, depending on the identity of the molecule which contacts the cell. Preferably, the provided method provides for elevated levels of MAT II β subunit by promoting expression of MAT II β subunit in the modulation of MAT II β subunit levels, to thereby affect or modulate the biological activity of MAT II and/or levels of S-adenosylmethionine (AdoMet), particularly in cancer cells and activated alloreactive or autoreactive lymphocytes. This modulation can affect cell growth and differentiation, i.e. preferably reduces the growth of cancer cells.

F.7. Antisense Oligonulceotide Therapy

It is also provided according to the present invention that expression of a MAT II β subunit can be modulated in a vertebrate subject through the administration of an antisense oligonucleotide derived from a nucleic acid molecule encoding a MAT II β subunit, such as those described in any of FIGS. 1–5 and 6 (corresponding to SEQ ID NOs: 16, 18, 20, 22, 24 and 1, respectively). Therapeutic methods utilizing antisense oligonucleotides have been described in the art, for example, in U.S. Pat. Nos. 5,627,158 and 5,734,033, the contents of each of which are herein incorporated by reference.

In one embodiment of the methods of the invention above the compound comprises an antisense nucleic acid which is complementary to a sequence present in a modulatable, transcriptional sequence. The compound can also be a double-stranded nucleic acid or a nucleic acid capable of forming a triple helix with a double-stranded DNA.

F.8. Formulation of Therapeutic Compositions

The MAT II β subunit biological activity modulating substances, gene therapy vectors, biologically activity MAT II β subunit gene products, and substances that inhibit or promote expression of a MAT II β subunit-encoding nucleic acid segment described above are adapted for administration as a pharmaceutical compositions as described above. Additional formulation and dose preparation techniques have been described in the art, see for example, those described in U.S. Pat. No. 5,326,902 issued to Seipp et al. on Jul. 5, 1994, U.S. Pat. No. 5,234,933 issued to Marnett et al. on Aug. 10, 1993, and PCT Publication WO 93/25521 of Johnson et al. published Dec. 23, 1993, the entire contents of each of which are herein incorporated by reference.

For the purposes described above, the identified substances can normally be administered systemically or partially, usually by oral or parenteral administration. The doses to be administered are determined depending upon age, body weight, symptom, the desired therapeutic effect, the route of administration, and the duration of the treatment etc. In a human adult, the doses per person per administration are generally between 1 mg and 500 mg, by oral administration, up to several times per day, and between 1 mg and 100 mg, by parenteral administration up to several times per day. Since the doses to be used depend upon various conditions, as mentioned above, there can be a case in which doses are lower than or greater than the ranges specified above.

Solid compositions for oral administration include compressed tablets, pills, dispersible powders, capsules, and granules. In such compositions, one or more of the active substance(s) is or are, admixed with at least one inert diluent (lactose, mannitol, glucose, hydroxypropylcellulose, microcrystalline cellulose, starch, polyvinylpyrrolidone, magnesium metasilicate alminate, etc.). The compositions can also comprise, as is normal practice, additional substances other than inert diluents: e.g. lubricating agents (magnesium stearate, etc.), disintegrating agents (cellulose, calcium glycolate etc.), and assisting agent for dissolving (glutamic acid, aspartic acid, etc.) stabilizing agent (lactose etc.). The tablets or pills may, if desired, be coated with gastric or enteric material (sugar, gelatin, hydroxypropylcellulose or hydroxypropylmethyl cellulose phthalate, etc.). Capsules include soft ones and hard ones.

Liquid compositions for oral administration include pharmaceutically-acceptable emulsions, solutions, suspensions, syrups and elixirs. In such compositions, one or more of the active substance(s) is or are admixed with inert diluent(s) commonly used in the art (purified water, ethanol etc.). Besides inert diluents, such compositions can also comprise adjuvants (wetting agents, suspending agents, etc.), sweetening agents, flavoring agents, perfuming agents and preserving agents.

Other compositions for oral administration include spray compositions which can be prepared by known methods and which comprise one or more of the active substance(s). Spray compositions can comprise additional substances other than inert diluents: e.g. preserving agents (sodium sulfite, etc.), isotonic buffer (sodium chloride, sodium citrate, citric acid, etc.). For preparation of such spray compositions, for example, the method described in U.S. Pat. Nos. 2,868,691 or 3,095,355 can be used.

Injections for parenteral administration include sterile aqueous or non-aqueous solution, suspensions and emulsions. In such compositions, one or more of active substance(s) is or are admixed with at least one inert aqueous diluent(s) (distilled water for injection, physiological salt solution etc.) or inert non-aqueous diluent(s) (propylene glycol, polyethylene glycol, olive oil, ethanol, POLYSOLBATE 80® etc.). Injections can comprise additional other than inert diluents: e.g. preserving agents, wetting agents, emulsifying agents, dispersing agents, stabilizing agents (lactose, etc.), assisting agents such as for dissolving (glutamic acid, aspartic acid, etc.). They can be sterilized, for example, by filtration through a bacteria-retaining filter, by incorporation of sterilizing agents in the compositions or by irradiation. They also can be manufactured in the form of sterile solid compositions, for example, by freeze-drying, and which can be dissolved in sterile water or some other sterile diluents for injection immediately before use.

Other compositions for administration include liquids for external use, and endermic linaments (ointment, etc.), suppositories and pessaries which comprise one or more of the active substance(s) and can be prepared by known methods.

G. Detecting a Polynucleotide or a Polypeptide of the Present Invention

Alternatively, the present invention provides a process of detecting a polypeptide of the present invention, wherein the process comprises immunoreacting the polypeptides with antibodies prepared according to the process described above to form antibody-polypeptide conjugates, and detecting the conjugates.

In yet another embodiment, the present invention provides a process of detecting messenger RNA transcripts that encode a polypeptide of the present invention, wherein the process comprises hybridizing the messenger RNA transcripts with polynucleotide sequences that encode the polypeptide to form duplexes; and detecting the duplex. Alternatively, the present invention provides a process of detecting DNA molecules that encode a polypeptide of the present invention, wherein the process comprises hybridizing DNA molecules with a polynucleotide that encodes that polypeptide to form duplexes; and detecting the duplexes.

The detection and screening assays disclosed herein can be used as a prognosis tool. MAT II β subunit-encoding polypeptides and nucleic acids can be readily used in clinical setting as a prognostic indicator for screening for levels of expression of MAT II β subunit and/or levels of S-adenosylmethionine (AdoMet), particularly in cancer cells and activated alloreactive or autoreactive lymphocytes.

The detection and screening assays disclosed herein can be also used as a part of a diagnostic process. MAT II β subunit-encoding polypeptides and nucleic acids can be readily used in clinical setting as a diagnostic indicator for screening for levels of expression of MAT II β subunit and/or levels of S-adenosylmethionine (AdoMet), particularly in cancer cells and activated alloreactive or autoreactive lymphocytes.

In another embodiment of the invention, the nucleic acid sequences which encode a MAT II β subunit polypeptide can also be used to generate hybridization probes which are useful for mapping naturally occurring genomic sequences and/or disease loci. The sequences can be mapped to a particular chromosome or to a specific region of the chromosome using well-known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) *Blood Rev.* 7:127–134, and Trask, B. J. (1991) *Trends Genet.* 7:149–154.

FISH (as described in Verma et al. (1988) *Human Chromosomes: A Manual of Basic Techniques*, Pergamon Press, New York, N.Y.) can be correlated with other physical chromosome mapping techniques and genetic map data. Examples of genetic map data can be found in the 1994 Genome Issue of *Science* (265:1981f). Correlation between the location of the gene encoding a MAT II β subunit polypeptide on a physical chromosomal map and a specific disease, or predisposition to a specific disease, can help delimit the region of DNA associated with that genetic disease. The nucleotide sequences of the subject invention can be used to detect differences in gene sequences between normal, carrier, or affected individuals.

In situ hybridization of chromosomal preparations and physical mapping techniques such as linkage analysis using established chromosomal markers can be used for extending genetic maps. Often the placement of a gene on the chromosome of another mammalian species, such as mouse, reveals associated markers also found in other mammals such as humans even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, ataxia-telangiectasia (A-T) to 11q22–23 (Gatti, R. A. et al. (1988) *Nature* 336:577–580), any sequences mapping to that area can represent associated or regulatory genes for further investigation. The nucleotide sequences of the present invention can thus also be used to detect differences in the chromosomal location due to translocation, inversion, etc. among normal, carrier, or affected individuals.

The mapping methods of the present invention also employ genomic and coding clones of the exons of a MAT II β subunit gene. Coding and genomic sequences for a human MAT II subunit gene are set forth in FIGS. 1–6 (SEQ ID NOs: 16, 18, 20, 22, 24 and 1, respectively). Thus, the present invention also provides genetic assays based on the genomic sequence of the human MAT II β subunit genes. An intronic sequence flanking an individual exons encoding a MAT II β subunit polypeptide is employed in the design of oligonucleotide primers suitable for the mutation analysis of human genomic DNA. Thus, intronic primers can be used to screen for genetic variants by a number of PCR-based techniques, including single-strand conformation polymorphism (SSCP) analysis (Orita, M., et al. (1989) *Proc Natl Acad Sci USA* 86(8): 2766–70), SSCP/heteroduplex analysis, enzyme mismatch cleavage, and direct sequence analysis of amplified exons (Kestila, M., et al. (1998) *Mol Cell* 1(4), 575–82; Yuan, B., et al. (1999) *Hum Mutat* 14(5): 440–6). Similar techniques can be applied to putative 5'-regulatory regions, e.g. the putative promoters 5' of a MAT II β subunit gene (SEQ ID NO: 1 and FIG. 6).

Automated methods can also be applied the large-scale characterization of single nucleotide polymorphisms (SNPs) (Brookes, A. J. (1999) *Gene* 234(2): 177–186; Wang, D. G., et al. (1998) *Science* 280(5366):1077–82) within and near a MAT II β subunit gene. Once genetic variants have been detected in specific patient populations, the present invention provides assays to detect the mutation by methods such as allele-specific hybridization (Stoneking, M., et al. (1991) *Am J Hum Genet* 48(2):370–82), or restriction analysis of amplified genomic DNA containing the specific mutation. Again, these detection methods can be automated using existing technology (Wang, D. G., et al. (1998) *Science* 280(5366): 1077–82). In the case of genetic disease or human phenotypes caused by repeat expansion (Lafreniere, R. G., et al. (1997) *Nat Genet* 15(3):298–302; Timchenko, L. T., and Caskey, C. T. (1996) *Faseb J* 10(14):1589–97, the invention provides an assay based on PCR of genomic DNA with oligonucleotide primers flanking the involved repeat.

As used herein and in the claims, the term "polymorphism" refers to the occurrence of two or more genetically determined alternative sequences or alleles in a population. A polymorphic marker is the locus at which divergence occurs. Preferred markers have at least two alleles, each occurring at frequency of greater than 1%. A polymorphic locus can be as small as one base pair.

The provided nucleic acid molecules can be labeled according to any technique known in the art, such as with radiolabels, fluorescent labels, enzymatic labels, sequence tags, etc. Such molecules can be used as allele-specific oligonucleotide probes. Body samples can be tested to determine whether a MAT II β subunit gene contains a polymorphism. Suitable body samples for testing include those comprising DNA, RNA or protein obtained from biopsies.

H. Screening Assays for a Polypeptide of the Present Invention

The present invention provides a process of screening a biological sample for the presence of a MAT II β subunit polypeptide. Preferably, the MAT II β subunit polypeptide possesses activity in modulating MAT II biological activity in accordance with the present invention. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to an antibody immunoreactive with the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microtiter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4C°. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the polypeptide.

Exposure time will vary inter alia with the biological conditions used, the concentration of antibody and polypeptide and the nature of the sample (e.g., fluid or tissue sample). Means for determining exposure time are well known to one of ordinary skill in the art. Typically, where the sample is fluid and the concentration of polypeptide in that sample is about $10^{-10}$ M, exposure time is from about 10 minutes to about 200 minutes.

The presence of polypeptide in the sample is detected by detecting the formation and presence of antibody-polypeptide conjugates. Means for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}P$, $^{125}I$, $^{14}C$), a second antibody or an enzyme such as horse radish peroxidase. Means for affixing indicators to antibodies are well known in the art. Commercial kits are available.

I. Screening Assay for Anti-Polypeptide Antibody

In another aspect, the present invention provides a process of screening a biological sample for the presence of antibodies immunoreactive with a MAT II β subunit polypeptide. Preferably the MAT II β subunit polypeptide has activity in the modulation of MAT II biological activity in accordance with the present invention. In accordance with such a process, a biological sample is exposed to a MAT II β subunit polypeptide under biological conditions and for a period of time sufficient for antibody-polypeptide conjugate formation and the formed conjugates are detected.

J. Screening Assay for Polynucleotide That Encodes a MAT II β Subunit Polypeptide of the Present Invention A DNA molecule and, particularly a probe molecule, can be used for hybridizing as an oligonucleotide probe to a DNA source suspected of encoding a MAT II β subunit polypeptide of the present invention. Preferably the MAT II II β subunit polypeptide has activity in the modulation of MAT II biological activity in accordance with the present invention. The probing is usually accomplished by hybridizing the oligonucleotide to a DNA source suspected of possessing a MAT II β subunit gene. In some cases, the probes constitute only a single probe, and in others, the probes constitute a collection of probes based on a certain amino acid sequence or sequences of the polypeptide and account in their diversity for the redundancy inherent in the genetic code.

A suitable source of DNA for probing in this manner is capable of expressing a polypeptide of the present invention and can be a genomic library of a cell line of interest. Alternatively, a source of DNA can include total DNA from the cell line of interest. Once the hybridization process of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) means for detecting and isolating other members of the polypeptide family and related polypeptides from a DNA library potentially containing such sequences; (3) primers for hybridizing to related sequences for the purpose of amplifying those sequences; (4) primers for altering native MAT II β subunit DNA sequences; as well as other techniques which rely on the similarity of the DNA sequences to those of the DNA segments herein disclosed.

As set forth above, in certain aspects, DNA sequence information provided by the invention allows for the preparation of relatively short DNA (or RNA) sequences (e.g., probes) that specifically hybridize to encoding sequences of a selected MAT II β subunit gene. In these aspects, nucleic acid probes of an appropriate length are prepared based on a consideration of the encoding sequence for a polypeptide of this invention. The ability of such nucleic acid probes to specifically hybridize to other encoding sequences lend them particular utility in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of a nucleic acid sequence of the present invention, such as a sequence shown in any of FIGS. 1–5 and 6 (SEQ ID NOs: 16, 18, 20, 22, 24 and 1, respectively). A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments can be readily prepared by, for example, directly synthesizing the fragment by chemical means, by application of nucleic acid reproduction technology, such as the PCR technology of U.S. Pat. No. 4,683,202, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M salt (e.g. NaCl), including particularly 200 mM salt, at temperatures of 50° C. to 70° C., including particularly temperatures of about 55° C., about 60° C. and about 65° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate polypeptide coding sequences from related species, functional equivalents, or the like, less stringent hybridization conditions are typically needed to allow formation of the heteroduplex. Under such circumstances, one employs conditions such as 0.15M–0.9M salt, at temperatures ranging from 20° C. to 55° C., including particularly temperatures of about 25° C., about 37° C., about 45° C., and about 50° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend interalia on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

J. Assay Kits

In another aspect, the present invention provides diagnostic assay kits for detecting the presence of a polypeptide of the present invention in biological samples, where the kits comprise a first container containing a first antibody capable of immunoreacting with the polypeptide, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also provides an assay kit for screening agents. Such a kit can contain a polypeptide of the present invention. The kit can contain reagents for detecting an interaction between an agent and a receptor of the present invention. The provided reagent can be radiolabeled. The kit can contain a known radiolabelled agent capable of binding or interacting with a receptor of the present invention.

In an alternative aspect, the present invention provides diagnostic assay kits for detecting the presence, in biological samples, of a polynucleotide that encodes a polypeptide of the present invention, the kits comprising a first container that contains a second polynucleotide identical or complementary to a segment of at least 10 contiguous nucleotide bases of, as a preferred example, any of FIGS. 1–5 and 6 (SEQ ID NO: 16,18, 20, 22, 24 and 1, respectively).

In another embodiment, the present invention provides diagnostic assay kits for detecting the presence, in a biological sample, of antibodies immunoreactive with a polypeptide of the present invention, the kits comprising a first container containing a MAT II β subunit polypeptide, that immunoreacts with the antibodies, with the polypeptide present in an amount sufficient to perform at least one assay. Preferably, the MAT II β subunit polypeptide has activity in the modulation of MAT II biological activity in accordance with the present invention. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide. When the reagent provided is a dry powder, the powder can be reconstituted by the addition of a suitable solvent. The solvent can be provided.

LABORATORY EXAMPLES

The following Laboratory Examples have been included to illustrate preferred modes of the invention. Certain aspects of the Examples are described in terms of techniques and procedures found or provided by the present inventors to work well in the practice of the invention. These Examples are exemplified through the use of standard laboratory practices of the inventors. In light of the present disclosure and the general level of skill in the art, those of skill will appreciate that the Examples are intended to be exemplary only and that numerous changes, modifications and alterations can be employed without departing from the spirit and scope of the invention.

Laboratory Examples 1–7

Cloning, Expression, and Characterization of the β Regulatory Subunit of Human Methionine Adenosyltransferase (MAT II)

The extrahepatic form of the enzyme Methionine adenosyltransferase (MAT), MAT II, consists of catalytic α2/α2' subunits and a non-catalytic β subunit, which is believed to have a regulatory function. The full-length cDNA that encodes the MAT II β subunit of human MAT II was cloned and sequenced. The cDNA sequence from human leukemic Jurkat T-cells, MOLT-4 cells, and normal peripheral blood lymphocytes from several individuals was identical. Thorough analysis of sequence homology failed to unravel similar DNA or protein sequences in the available DNA or protein databases, suggesting a unique sequence for the β subunit protein. The cDNA encodes for 334 amino acid protein with a calculated molecular weight of 37,551.81, and a pI of 6.90.

The β subunit cDNA was cloned into the pQE-30™ expression vector, and the recombinant poly-His tagged protein was expressed in *E. coli*. The expressed protein migrated at the slightly higher molecular size than the native protein due to the presence of the N-terminal His tag, and both the recombinant and native proteins were recognized by antibodies to the human MAT II, to synthetic peptides copying the sequence of native β subunit protein tryptic peptides, and to the recombinant MAT II β subunit protein. There was no immunological crossreactivity between the MAT II α2 or β subunit proteins. Furthermore, none of the anti-β subunit antibodies reacted with protein extracts of *E. coli* host cells that were either untransfected, or that were transfected with the same vector and expressing the human recombinant MAT II α2 subunit cDNA, suggesting that these bacteria have no β subunit protein.

The recombinant MAT II β subunit associated with *E. coli* as well as human MAT II α subunits. This association changed the kinetic properties of the enzyme and lowered the Km of MAT for L-methionine. Together, the data show that we have cloned and expressed the human MAT II β subunit, and confirmed its regulatory function. This knowledge affords a molecular means by which the activity of MAT, and consequently the levels of AdoMet can be modulated in mammalian cells.

Laboratory Example 1

Cloning of the Human MAT II β Subunit cDNA

Degenerate primers (Table 2) were designed based on partial amino acid sequence of two tryptic peptides, which were generated by partial digestion of pure MAT II protein as previously described (De La Rosa et al. (1992) J. Biol. Chem. 267, 10699–704; De La Rosa et al. (1995) J. Biol. Chem. 270, 21860–8; LeGros et al. (1997) J. Biol. Chem. 272, 16040–7). The forward 5' DEG primer (5'-GTNGG NMGNGARAARGARYTNWSNATHCAYTTYGTNCC, SEQ ID NO: 10) was based on the sequence of the N-terminal peptide (VGREKELSIHFVPGSNELV, SEQ ID NO: 9), and the reverse 3' DEG primer (5'-GTYTGYTCRTTNCCNSWCCARTGRMNGTNCCYTT, SEQ ID NO: 15) was based on the sequence of an internal peptide (LDPSIKGTFHWSGNEQT, SEQ ID NO: 14).

Total RNA was extracted from the human T cell leukemia lines, Jurkat (ATCC-8163) or MOLT4 (ATCC-1582) using RNazol B™ (Tel-Test, Inc., Friendswood, Tex.). The RNA (2 μg) was reverse transcribed into cDNA using 25 units of AMV-reverse transcriptase (Promega, Madison, Wis.), Oligo $dT_{(15)}$ (Promega), and 1 mM dNTPs (Pharmacia, Peapack, N.J.). The cDNA was amplified using Taq DNA polymerase and the 5'DEG and 3'DEG primers (Table 2). After 30 cycles of denaturation at 95° C. for 30 seconds, annealing at 48° C. for 1 minute, and extension at 72° C. for 1 minute, a 765 bp PCR product was generated. The amplified PCR product was purified from agarose gel using QIAquick™ gel extraction spin columns (Qiagen, Valencia, Calif.), ligated into the pGEM®-T-easy vector (Promega), and used to transform E. coli strain JM109 (Promega). Positive clones were selected on LB agar (Difco) containing 100 μg/ml Ampicillin, 40 μg/ml Xgal, and 100 μM isopropyl-β-D-thiogalactoside (IPTG) (Sigma, St. Louis, Mo.).

Figure 7:
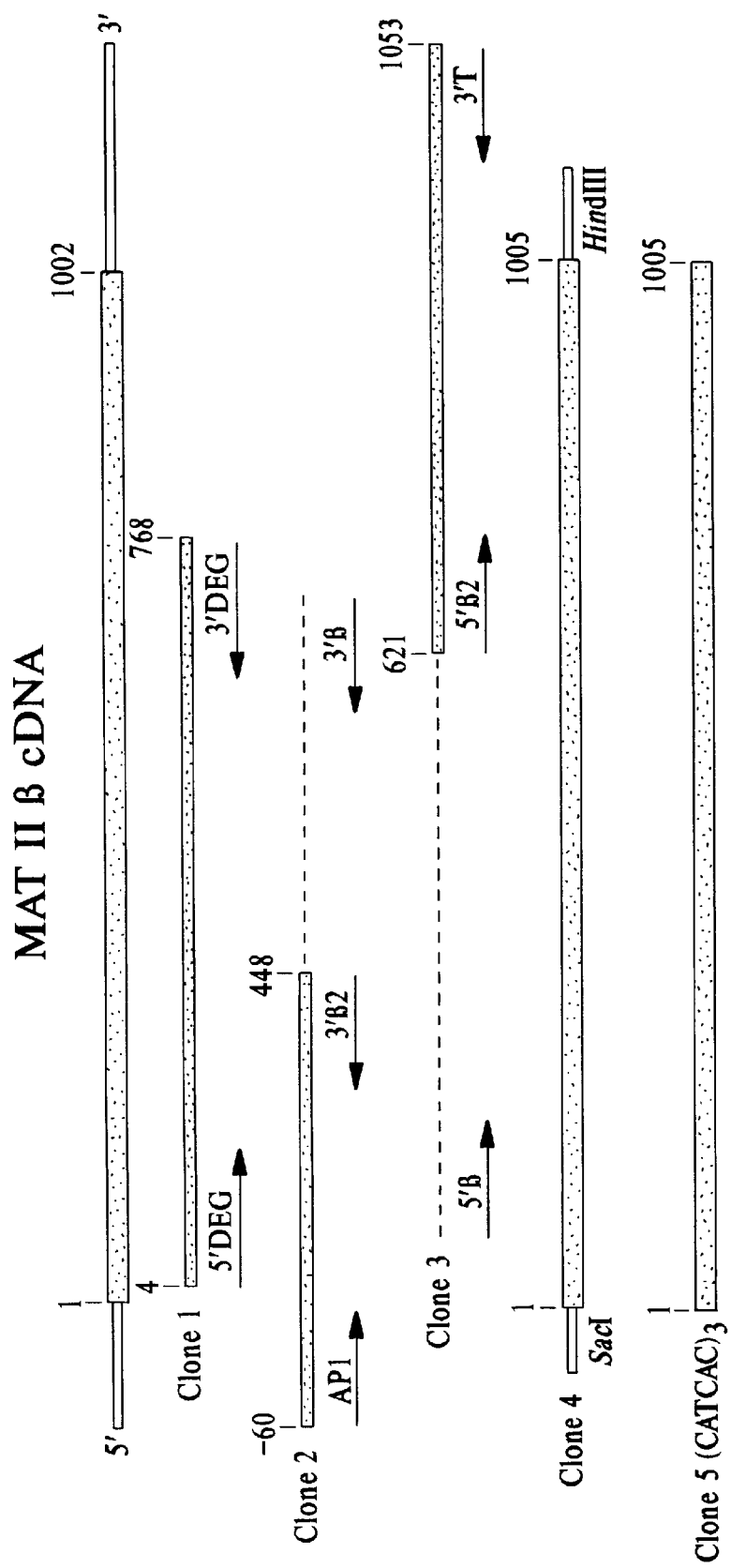
FIG. 7 depicts the cloning strategy and position of various primers used to elucidate the sequence of the β subunit of human lymphocyte MAT II. The sequence of the various primers is indicated in Table 2. The first amplification was conducted using generate primers (5' DEG and 3' DEG), which were designed based on the sequence of the two tryptic peptides of native human MAT II β subunit protein. Subsequent sequencing was performed using the sequence specific primers, indicated.

Plasmid DNA was purified from positive clones and checked by restriction digestion with EcoRI (Promega) to verify the presence of the cloned PCR product. The cloned DNA was sequenced using the fmol cycle sequencing system (Promega). Clone 1, which contained sequences matching both degenerate primers, as well as sequences that encode the remaining aa sequence in the N-terminal and internal β subunit peptides was selected for further sequencing (FIG. 7). Based on the sequence of Clone 1, non-degenerate primers were synthesized (Table 2).

Laboratory Example 2

3' and 5' Rapid Amplification of cDNA Ends (RACE)

Since Clone 1 was a partial sequence, the RACE methodology was employed to obtain overlapping 5' and 3' clones from human Jurkat and MOLT4 cells cDNAs. The missing 5' sequence of the β subunit cDNA was obtained by 5' RACE technique. Marathon Ready™, MOLT4 cDNA (Clontech, Palo Alto, Calif.) was amplified using Marathon Ready™ primer AP1 and a 3' MAT II β subunit-specific (3'β) primer (5'-CATTCTCTTCTCTGCTAGCTGCC, SEQ ID NO: 3). The 776 bp PCR product was purified using QIAquick™ gel purification spin columns (Qiagen) and subjected to nested PCR using the AP1 primer and another β subunit-specific (3'β 2) primer (5'-CTCTCTGTAAGGTGGATTTGT, SEQ ID NO: 2), Table 2. The 508 bp nested PCR product was purified, cloned, and 10 clones were sequenced as described above. The sequence provided the putative ATG intiation signal and verified the previous sequence obtained with the degenerate primers. Clone 2, which represents the consensus sequence, was selected for further studies.

To obtain the DNA sequence that encodes the carboxy terminal end of the -subunit a 3' RACE technique was utilized. RNA from Jurkat cells was reverse transcribed into cDNA as described above, except that a T-tailed primer (5'-GGCCACGCGTCGACTAGTACT$_{17}$, SEQ ID NO:26) was used in place of Oligo $dT_{(15)}$. The cDNA was amplified using the 5' MAT II subunit-specific forward (5') primer (5'-CTGTCGGCTGGTGGAGGAGGAA, SEQ ID NO: 6), and a 3'-primer identical to the primer used to make the cDNA, but lacking the T-tail. The resulting 981 base pair PCR product was subjected to a nested PCR reaction using a 5' 2 forward primer complementary to the internal region of the cloned DNA (5'-GCAACAAGTCAGCAAACATGG, SEQ ID NO: 5). A 433 bp PCR product was generated, ligated into the pGEM® T-easy vector, and used to transform E. coli strain JM109. Positive clones were selected as described above, and the cloned DNA was sequenced using Thermo-Sequence™ (Amersham Pharmacia Biotech AB, Uppsala, Sweden) and the Visible Genetics™ (Visible Genetics, Toronto, Ontario, Canada) cycle sequencing system utilizing fluorescent Cy5 labeled M13-forward and M13-reverse primers. A total of 10 clones were sequenced to verify the "in frame" sequence from base 765 to base 1005—the last base in the stop codon (TAG). Clone 3 was selected for further studies (FIG. 7).

Laboratory Example 3

Cloning and Expression of MAT II β Subunit

The cDNA prepared from resting peripheral blood mononuclear cells (PBMC) total RNA was amplified by PCR using pfu DNA polymerase (Promega), and the MAT II β 5' subunit-specific primer, 5' β r (5'-CGAGCTCATGGTGGGGAGGGAGAAAGAACTGT, SEQ ID NO: 7) and 3' subunit-specific primer, 3' β r (5'-CCCAAGCTTAACCCAACACAAATAAACTAATGA, SEQ ID NO: 4), shown in Table 2. For cloning purposes, the 5' primer contained a SacI restriction site and the 3' primer had a HindIII site. The PCR product was purified using QIAquick™ gel extraction (Qiagen) as described above. Using 200 nM dATP and 2.5 units of Taq DNA polymerase (Promega), A-overhangs were added to the purified PCR product in a reaction carried out at 72° C. for 2 hours. Following cleanup of the modified PCR product, the product was ligated into the pGEM®-T-easy vector (Promega), and subsequently used to transform E. coli strain JM109. Ten positive clones were fully sequenced using the fmol cycle sequencing system (Promega) to rule out any possible base substitutions, and one representative clone, Clone 4, which represented the full length β subunit cDNA, was used for further studies. The sequence of the ORF was identical for cDNA representing RNA from Jurkat cells, MOLT4 cells, and normal human PBMC. The MAT II β cDNA was excised from the pGEM® T-easy vector using SacI and HindIII, and purified.

Expression vector pQE-30™ (Qiagen), which is designed to express proteins containing a six-histidine (His) tag at the N-terminal was used. The vector was linearized by digestion with the restriction enzymes SacI and HindIII for 1 hour at 37° C., then purified from an agarose gel and incubated at 37° C. with 5 units of alkaline phosphatase (Promega) to enhance the efficiency of ligation. SacI and HindIII digested Clone 4 was directionally cloned into unique SacI and HindIII sites in the multiple cloning site of the pQE-30™ vector. Following ligation of the MAT II β cDNA into the prepared pQE-30™ vector, the ligated vector was used to transform *E. coli* expression strain M15 (Qiagen). Cursory sequencing of 20 positive clones was carried out using the fmol cycle sequencing system (Promega) and the clones were verified for proper frame and orientation of the MAT II β cDNA. A representative clone, Clone 5, was inoculated into Luria-Bertani (LB) broth containing 25 μg/ml kanamycin and 100 μg/ml ampicillin. The culture was incubated, with shaking, at 37° C. until an $OD_{600}$ of 0.5–0.7 was reached, then IPTG (Sigma) was added to a final concentration of 1 mM, and the culture was allowed to incubate for an additional 4 hours under the same conditions. Bacterial pellets were disrupted using sonication, then analyzed via Western blot and MAT II β-specific polyclonal antibodies that were generated to the two MAT II β peptides (De La Rosa et al. (1992) J. Biol. Chem. 267,10699–704; De La Rosa et al. (1995) J. Biol. Chem. 270, 21860–68; LeGros et al. (1997) J. Biol. Chem. 272, 16040–μ47).

Laboratory Example 4

Purification of Recombinant MAT II β

The MAT II β expression clone, Clone 5, was inoculated into one liter of LB broth containing 25 μg/ml kanamycin and 100 μg/ml ampicillin, then incubated with shaking at 37° C. until an $OD_{600}$ of 0.5–0.7 was reached. IPTG (Sigma) was added to a final concentration of 1 mM, and the culture was allowed to incubate for an additional 4 hours under the same conditions. Initial attempts to purify His-tagged MAT II β subunit under native conditions via sonication and Ni-NTA agarose resulted in a complex of the *E. coli* MAT α subunit and the recombinant human β subunit. Therefore, subsequent purification of MAT II β away from the endogenous *E. coli* MAT α was performed by two methods. The first, involved purification of the His-tagged protein under denaturing conditions of 8M urea, and the second involved separation of SDS-PAGE and elution of the β subunit protein from the gel.

To purify recombinant MAT II β protein under denaturing conditions, the cell pellet was lysed at room temperature by stirring the pellet in a buffered solution containing 8M urea, pH 8.0. Once the solution became translucent, the cellular debris were removed by centrifugation. The clarified supernatant was loaded onto a Ni-NTA agarose column (Qiagen) to capture the His-tagged protein. The column was washed with several volumes of buffered 8M urea, pH 6.3 until a $OD_{280}$ of 0.001–0.005 is reached. Elution of the recombinant MAT II β (rMAT II β) was carried out using buffered 8M urea, pH 5.9 and pH 4.5. The eluted protein was extensively dialyzed against 50 mM Tris-HCl, pH 7.5, then concentrated and analyzed by Western blots and silver stained SDS-PAGE for determination of size and purity. The pure recombinant human MAT II β subunit protein was used to immunize rabbits and to generate polyclonal antibodies as detailed below.

In some experiments, the Ni-agarose purified proteins were separated on SDS-PAGE and visualized by impregnation in cold 300 mM KCl, and the band corresponding to the 38–39 kDa protein was excised, protein was electroeluted from the gel into Tris-glycine buffer, pH 8, and dialyzed against 10 mM ammonium bicarbonate then lyophilized. The lyophilized protein was reconstituted in 50 mM Tris-HCl, pH 7.5, and analyzed by Western blots and silver stains for size and purity. The purified β subunit protein was also analyzed for functional activity in MAT assays containing *E. coli* MAT α or recombinant human MAT II α protein.

Laboratory Example 5

Production of Polyclonal Antibodies to MAT II β Subunit

Polyclonal antibodies were generated to the β subunit synthetic peptides (VGREKELSIHFVPGSNELV, SEQ ID NO: 9) and (LDPSIKGTFHWSGNEQT, SEQ ID NO:14) (De La Rosa et al. (1992) J. Biol. Chem. 267, 10699–704; De La Rosa et al. (1995) J. Biol. Chem. 270, 21860–68; LeGros et al. (1997) J. Biol. Chem. 272, 16040–47), as well as to the purified rMAT II β protein. Both antibodies were generated in male New Zealand White rabbits (Myrtle's Rabbitry, Thompson Station, Tenn.), weighing 5–6 lb. Prior to initial immunizations, a preimmune blood was drawn and sera were used as a negative control in subsequent Enzyme-linked Immunosorbent Assay (ELISA) titer determinations and in Western blots. The 2 synthetic subunit peptides were combined, emulsified in an equal volume of Freunds Adjuvant Complete (Sigma), and injected into rabbits. The purified rMAT II β subunit was similarly treated. Initial injections were made in 3 sites-each hindquarter and the back of the neck. Boosters were made every 2 weeks following the removal of 10 cc of blood, from the ear vein, for the determination of antibody titers by ELISA. Freunds Adjuvant Incomplete (Sigma) was used in all booster injections.

Antibody titers were determined in an ELISA using the rMAT II β protein diluted in a 50 mM $NaHCO_3$ solution, pH 9.6, and incubated overnight at 37° C. in ELISA titer plates. Following a wash with 1×phosphate buffered saline (PBS) containing 0.05% TWEEN (PBS-T), the wells were blocked for 30 minutes at 37° C. with a solution containing 1×PBS and 1% bovine serum albumin (1% BSA-PBS). After washing, serial dilutions of rabbit antiserum in 1% BSA-PBS were added to wells containing the bound rMAT II β protein and incubated at 37° C. for 1.5 hours. Following a wash with 1×PBS, secondary antibody (goat anti-rabbit/ horseradish peroxidase (HRPO) diluted 1:1000 in 1% BSA-PBS) was added to each well, then incubated for 45 minutes at 37° C. The final wash was made with 1×PBS-T, then followed by a wash with 1×PBS. Color reagent (5 mM 5-aminosalicylic acid, pH 6.0 and 10 μl/ml 0.5% $H_2O_2$) was added to each well, then incubated at room temperature for 30 minutes. Titers were determined by measuring absorbance at 478 nm with a cutoff of 0.1 over control wells containing pre-immune serum. After the titers had reached a plateau (12–14 weeks) the final rabbit serum was collected.

Laboratory Example 6

SDS-PAGE and Western Blotting

*E. coli* cell extracts containing recombinant MAT II β subunit or pure recombinant MAT II β subunit protein were diluted in loading buffer (60 mM Tris-HCl, pH 6.8, 2% SDS, 5% 2-mercaptoethanol, and 5% glycerol), heated in a boiling water bath for 4 minutes, and analyzed by SDS-PAGE (10% total acrylamide, 2.7% bisacrylamide) as previously (De La Rosa et al. (1992) J. Biol. Chem. 267, 10699–704). After electro-blotting the proteins onto the nitrocellulose for 1 hour at 25 to 30 V/cm, the blots were blocked overnight with 6% nonfat dry milk in TBS (50 mM Tris, pH 7.5, and 150 mM NaCl). Following the removal of the blocking solution, the blot was washed in TBS, and incubated with primary polyclonal anti-holoenzyme antisera (Kotb et al. (1990) Biochim. Biophys. Acta 1040, 137–44), or polyclonal antisera generated against either pure human recombinant MAT II α2 or β subunits, or against the two synthetic peptides copying sequences of the β subunits. The blots were developed with secondary anti-rabbit antibodies conjugated to horseradish peroxidase, and the luminol-chemiluminescence reagents ((ECL®, Amersham Pharmacia Biotech AB, Uppsala, Sweden ) as previously described (De La Rosa et al. (1992) J. Biol. Chem. 267, 10699–704). The processed blots were exposed to Kodak X-Omat™ (Eastman Kodak Company, Rochester, N.Y.) film and the autoradiograms were analyzed. For some experiments, the autoradiograms were scanned using a Howtek Scanmaster-3 scanner (Protein Data Base, Inc., Huntington Station, N.Y.) and the intensity of the desired band was integrated and expressed in arbitrary units.

Laboratory Example 7

MAT Assay

MAT activity was assayed as previously described (22, 29,31). The assay contained 5–120 µM L-methionine (L-Met), 5 mM ATP in 50 mM TES buffer, pH 7.4, 50 mM KCl, 15 mM $MgCl_2$, 0.3 mM EDTA, and 4 mM DTT. The L-Met concentration was varied as indicated in the kinetic analysis. One unit (U) of MAT activity is defined as the amount of enzyme that catalyzes the formation of 1 nmol of AdoMet in 1 hour.

Results of Laboratory Examples 1–7 cDNA and Predicted Protein Sequence of the Human MAT II β Subunit

The cloning strategy was based on the design of degenerate primers representing partial amino acid sequence of an N-terminal (19-mer) and an internal (17-mer) peptides of the trypsin digested β subunit protein, purified from human lymphocytes (De La Rosa et al. (1992) J. Biol. Chem. 267, 10699–704; De La Rosa et al. (1995) J. Biol. Chem. 270, 21860–8). Complementary DNA prepared from Jurkat cells mRNA was amplified with the degenerate primers, 5'DEG and 3'DEG (Table 2), that would encode partial sequences of the 2 β subunit peptides. The cDNA from positive clones were isolated at the preparative level and entirely sequenced in both directions. The cDNA clones that contained sequences corresponding to both peptides were selected for further sequencing, and Clone 1 (765 base pairs), which represented the consensus sequence, was fully characterized for the design of non-degenerate primers. Clone 1, which represents a partial sequence of the β subunit cDNA, would be expected to encode for 255 amino acids. However, since the β subunit migrates on SDS-PAGE as a 38 kDa protein it was estimated that at least 60–80 amino acids or 180–240 base pairs were still unaccounted for. Accordingly, sequence-specific primers based on the sequence of Clone 1 were synthesized and used in 3' and 5' RACE to obtain the complete open reading frame (ORF) of the β subunit cDNA, shown in FIG. 8.

TABLE 2

MAT II β Cloning Primers (5'→3')

Degenerate Primers

5'DEG (GTNGGNMGNGARAARGARYTNWSNATHCAYTTYGTNCC)
3'DEG (GTYTGYTCRTTNCCNSWCCARTGRAANGTNCCYTT)

TABLE 2-continued

MAT II β Cloning Primers (5'→3')

5' RACE Primers

AP1 (Clontech-Unknown)
3'β (CATTCTCTTCTCTGCTAGCTGCC)
3'β2 (CTCTCTGTAAGGTGGATTTGT)

3' RACE Primers

5'β (CTGTCGGCTGGTGGAGGAGGAA)
5'β2 (GCAACAAGTCAGCAAACATGG)
3'T (GGCCACGCGTCGACTAGTAC)

MAT II β Cloning Primers

5'rβ (CGAGCTCATGGTGGGAGGGAGAAAGAACTGT)
3'rβ (CCCAAGCTTAACCCAACACAAATAAACTAATGA)

A minimum of 10 positive clones from 3' or 5' RACE were sequenced in both directions, and Clone 2 represented the consensus of the 5' RACE clones; whereas, Clone 3 represented that of the 3' RACE clones. The sequence of Clone 2, which was generated by 5' RACE, showed that Clone 1 was only missing the ATG start codon at its 5' end. The authenticity of this ATG codon as the intiator codon was confirmed in several ways. First, this ATG is in frame with sequences that encode for amino acids found in the N-terminal β subunit peptide (FIG. 8). Second, the sequence of bases flanking this ATG codon are in accordance with sequences identified by Kozak (Kozak, M. (1989) J. Cell Biol. 108, 229–241) as consensus sequences preceeding or following an authentic initiator codon. For example, the sequence (−3)GnnATGG(+4) showed the second highest incidence of functional initiator codons (130 out of 699 tested) in vertebrate mRNAs analyzed (Kozak, M. (1989) J. Cell Biol. 108, 229–241). In addition, the presence of a "C" at position −1 and a "G" at positions −3 and −6, provides further support that the ATG in the 5' GACGGCGGGC ATGG (SEQ ID NO: 11) sequence of Clone 2 is the intiator codon for the β subunit cDNA. Clone 2 also provided 60 base pairs sequence of the 5' untranslated sequence of the cDNA.

Clone 3, which was generated by 3'RACE and represented the consensus sequence of 10 sequenced clones, provided the remaining 3' sequence of the β subunit cDNA. This clone provided an additional 288 base pairs, which included the remaining 3' 237 base pairs of the ORF, followed by the termination codon, TGA, at position 1003 (FIG. 8). Clone 3 also provided and an additional 48 base pairs of 3' untranslated sequence.

Based on the sequence of Clones 1, 2, and 3, specific primers were synthesized to amplify the full length cDNA of the β subunit 1005 base pairs, including the intiator and terminator codons. Ten clones containing the full length cDNA of the β subunit were sequenced in both directions and the consensus sequence, represented by Clone 4, is shown in FIG. 8.

No sequence differences were noted between the sequence of Clone 4 and cDNA prepared from normal human PBMC of several individuals, or cDNA from Jurkat and MOLT-4 cells. Further analysis of the 3' untranslated region of the β subunit cDNA provided 1807 base pairs of untranslated sequence, which included the polyadenylation signal sequence AATAAA (SEQ ID NO:8) (Fitzgerald, M., and Shenk, T. (1981) Cell 24, 251–260; Proudfoot, N. J., and Brownlee, G. G. (1976) Nature 263, 211–214) at position 1766, beginning 24 bp upstream of the poly(A) region, as shown in FIG. 8.

Sequence Comparisons

The cloned full-length cDNA contained standard 5'- and 3'-flanking regions and an open reading frame of 1002 base pairs. The cDNA encodes for 334 amino acids with a calculated molecular weight of 37,551.81, and has a pI of 6.90. Thus, unlike the MAT II α2 and α2' subunits, which migrate at higher than expected molecular weight on SDS-PAGE (Kotb, M., and Kredich, N. M. (1985) J. Biol. Chem. 260, 3923–30; De La Rosa et al. (1992) J. Biol. Chem. 267, 10699–704; De La Rosa et al. (1995) J. Biol. Chem. 270, 21860–8), the MAT II β subunit migrates at its expected molecular mass of 38 kDa.

Analysis of the DNA and the protein sequences on databases from GeneBank™ using, among others, the Advanced Blast program, EMBL, PSI-Blast, Swiss Port, and Cognitor databases, revealed no significant homology between the MAT II β subunit and any previously reported protein. Two short motifs, RVLVTGATGLLG (SEQ ID NO: 12) and DYVFDG (SEQ ID NO: 13) seemed to be shared with dTDP-4-dehydrorhamnose reductase, several nucleoside-diphosphate-sugar epimerases (Maceratesi et al. (1998) Mol. Genet. Metab. 63, 26–30) and other proteins involved in the synthesis of polysaccharides (Pissowotzki et al. (1991) Mol. Gen. Genet. 231, 113–123).

The amino acid composition revealed a relatively high content of hydrophobic amino acids, accounting for more than 30% of the total amino acid composition of the protein (Table 3). The frequency of His, Arg, and Trp in the β subunit protein was almost twice the average frequency of these residues in proteins (Klapper, M. (1977) Biochim. Biophys. Acta 78, 1018–1024), while the frequency of Gly, Ser, and Thr was almost half the normal frequency (Table 3). The hydropathy profile of the MAT II α2 and β subunits, as analyzed by the Kyte-Doolittle method and presented in FIG. 9, revealed that the β subunit has two hydrophobic pockets, and there was no indication that the protein possesses transmembrane regions.

TABLE 3

Amino Acid analysis of the MAT II β subunit protein

| Amino Acid | Amino Acid | Number | Mole % | Weight (%) | Average f (%)* |
|---|---|---|---|---|---|
| A | Ala | 29 | 8.68 | 5.49 | 9.0 |
| C | Cys | 6 | 1.80 | 1.65 | 2.8 |
| D | Asp | 17 | 5.09 | 5.21 | 5.5 |
| E | Glu | 23 | 6.89 | 7.91 | 6.2 |
| F | Phe | 15 | 4.49 | 5.88 | 3.5 |
| G | Gly | 20 | 5.99 | 3.04 | 7.5 |
| H | His | 13 | 3.89 | 4.75 | 2.1 |
| I | Ile | 17 | 5.09 | 5.13 | 4.6 |
| K | Lys | 17 | 5.09 | 5.81 | 7.0 |
| L | Leu | 28 | 8.38 | 8.44 | 7.5 |
| M | Met | 6 | 1.80 | 2.10 | 1.7 |
| N | Asn | 18 | 5.39 | 5.47 | 4.4 |
| P | Pro | 19 | 5.69 | 4.92 | 4.6 |
| Q | Gln | 15 | 4.49 | 5.12 | 3.9 |
| R | Arg | 22 | 6.59 | 9.15 | 4.7 |
| S | Ser | 17 | 5.09 | 3.94 | 7.1 |
| T | Thr | 13 | 3.89 | 3.50 | 6.0 |
| V | Val | 28 | 8.38 | 7.40 | 6.9 |
| W | Trp | 5 | 1.50 | 2.48 | 1.1 |
| Y | Tyr | 6 | 1.80 | 2.6 | 3.5 |

*The average frequency (%) of occurrence of amino acid residues in 207 unrelated proteins of known sequence.

Expression of the Recombinant β Subunit Protein in E. coli

Clone 4, which represented the full length cDNA encoding the complete ORF (1002 base pairs) for the β subunit, was directionally cloned into the pQE-30™ expression vector, which was designed to express the β subunit protein with a poly-His tag at the N-terminal end of the molecule. Clone 5, which represented 20 sequenced clones, provided expression of the β subunit protein in E. coli. Antibodies to synthetic peptides copying the sequence of the N-terminal and internal β subunit protein peptides were found to recognize the recombinant 38-kDa protein in transfected E. coli extracts, as shown in FIGS. 10 and 11. In concordance with our previous studies (Kotb et al. (1990) Biochim. Biophys. Acta 1040, 137–44), there was no immunological crossreactivity between the MAT II α and β subunits. Furthermore, no reactivity was detected between the anti-β peptides and protein extracts of E. coli host cells that were either untransfected, or that were transfected with the same vector and expressing the human recombinant MAT II α2 subunit cDNA (FIG. 10, panel B) (De La Rosa et al. (1995) J. Biol. Chem. 270, 21860–68).

Figure 10A:
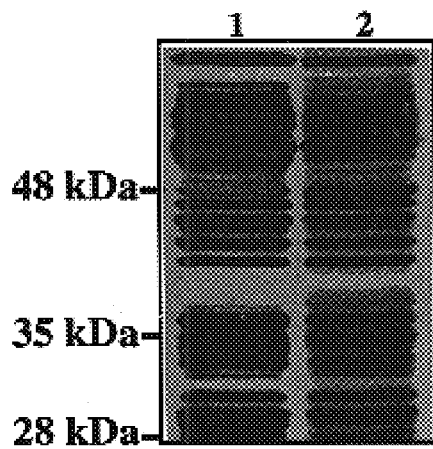
FIGS. 10A–D depict expression of β subunit cDNA in *E. coli*, and purification of recombinant β subunit protein. Clone 4, which represented the full length cDNA encoding the complete ORF for the β subunit, was directionally cloned into the pQE-30™ expression vector, which was designed to express the β subunit protein with a poly-His tag at the N-terminal end of the molecule. Clone 5, which represented 20 sequenced clones, provided expression of the β subunit protein in *E. coli*.
Figure 10B:
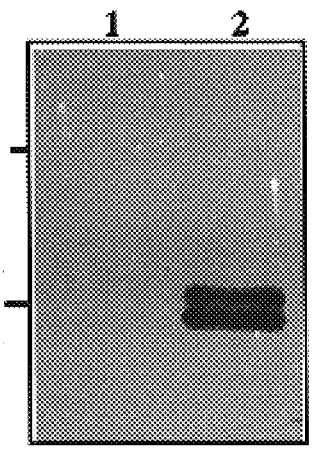
Figure 10C:
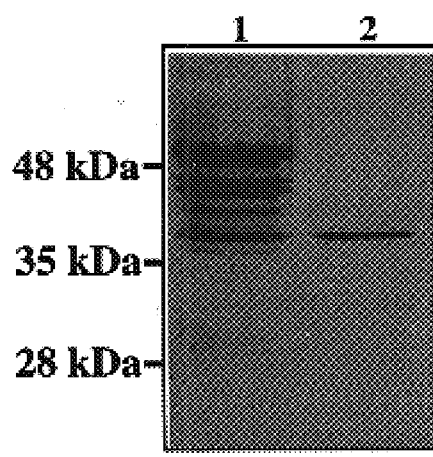
Figure 10D:
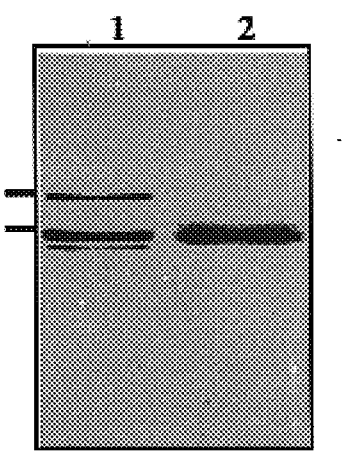
Figure 11A:
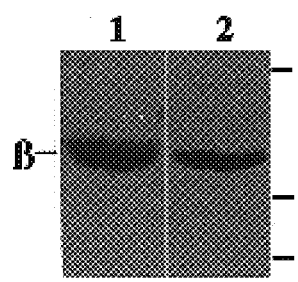
FIGS. 11A and 11B depicts the immunoreactivity of the recombinant and native β subunit protein with anti-β subunit protein antibodies.
Figure 11B:
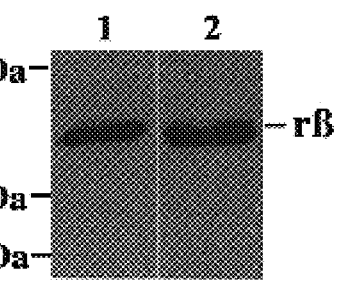

When the six-His-tagged recombinant MAT II β subunit was purified on Ni-NTA agarose column and eluted with 300 mM imidazole, analysis of the dialyzed protein on silver stained SDS-PAGE showed that several protein bands co-purified with the recombinant protein (FIG. 10C, lane 1). Further analysis by Western blot, which was probed with antibodies to both the α and β subunits, showed that the endogenous E. coli MAT α protein was co-purifying with the recombinant human MAT II β subunit protein (FIG. 10D, lane 1). To purify the recombinant MAT II β subunit protein away from the endogenous E. coli MAT α protein, the Ni-agarose purified proteins were separated on SDS-PAGE, the protein bands visualized by impregnation in cold 300 mM KCl, and the band corresponding to the 38–39 kDa protein was excised. The protein was electroeluted from the gel slice into Tris-glycine buffer, pH 8, dialyzed, lyophilized, reconstituted in 50 mM Tris-Cl buffer pH 7.5, and re-analyzed. Analysis of this purified protein on silver stained SDS-PAGE showed the migration of a single 38–39 kDa protein (FIG. 10, panel C, lane 2), and the Western blot revealed that only the recombinant human MAT II β subunit protein was present in this fraction (FIG. 10, panel D, lane 2).

The identity of the immunoreactive band with the MAT II β subunit protein was verified by the fact it was recognized by antibodies generated to either the β subunit partial peptides as well as by antibodies to the whole recombinant human MAT II β subunit protein (FIG. 11). Again, neither antibody to the β subunit showed any reactivity with any E. coli protein (FIG. 10).

Functional Analysis of the Recombinant Human MAT II β Subunit Protein

The recombinant human MAT II β subunit protein was found to have no MAT catalytic activity; however, it modulated the kinetic properties of the MAT II α2 catalytic subunit. The recombinant MAT II β subunit protein associated spontaneously with E. coli as well as with the recombinant human MAT II α subunits.

The effect of the MAT II β subunit protein on the kinetic activity of the E. coli MAT or the recombinant human MAT II α2 was analyzed in standard MAT assays. In the absence of the MAT II β subunit, both the E. coli MAT and the recombinant human MAT II α2 exhibited normal Michaelis and Menten kinetics with the apparent presence of a single catalytic form, and a Km for L-Met of 80–83 μM. In the presence of the MAT II β subunit, however, another kinetic form with a Km for L-Met of 32–34 μM was also apparent, in each case (FIG. 12).

Discussion of Laboratory Examples 1–7

The existence of multiple isozymes of MAT in mammalian tissues is well established (reviewed in Tabor, C. W., and Tabor, H. (1984) Adv. Enzymol. Relat. Areas Mol. Biol. 56, 251–82; Kotb, M., and Geller, A. M. (1993) Pharmacol. Ther. 59, 125–43). Whereas, the liver-specific enzyme appears to be a homodimer or tetramer of a single α1 subunit, the extrahepatic MAT II enzyme, which is expressed in all tissues, appears to consist of no-identical subunits, α2 and β. In 1985, Kotb and Kredich (Kotb, M., and Kredich, N. M. (1985) J. Biol. Chem. 260, 3923–30) reported that native MAT II from human leukemic cells has a molecular weight of 185,000 and consists of two related subunits α2 and α2', which migrated on SDS-PAGE as 53-, and 51-kDa proteins and had an identical V8-protease peptide banding pattern.

By contrast, the β subunit migrated on SDS-PAGE as a 38-kDa protein and had a peptide banding pattern that was quite distinct from that of the two α2 subunits, suggesting that β is distinct from the α2 subunit. Antibodies to the pure MAT II enzyme from human leukemic cells, whose purity was verified by analytical ultracentrifugational analysis, recognized both α2 and β subunits in human lymphocytes, and showed crossreactivity with E. coli and yeast MAT α subunits, which is not surprising given the now known high degree of primary sequence homology of MAT catalytic subunits in the many species analyzed. However, there was no indication that the anti-human MAT II antibodies were recognizing a protein similar to the β subunit in either E. coli or yeast cell extracts (Kotb et al. (1990) Biochim. Biophys. Acta 1040, 137–44). Moreover, polyclonal antibodies to E. coli or yeast MAT reacted with the human MAT I, II and III α subunits, but failed to recognize the MAT II β subunit protein. Together, these findings suggested that the β subunit of MAT II is distinct from the MAT α2/α2' subunits.

Several complementary forms of evidence indicate that the cDNA characterized herein from Jurkat T-cells, MOLT-4 cells, and normal peripheral blood mononuclear cells is that of the human MAT II β subunit. First, the deduced amino acid sequence contains sequences that are identical to those of the two tryptic human lymphocyte β subunit peptide sequences. Second, expression of this cDNA in E. coli gave a protein band that migrated at the expected size of the authentic β subunit in SDS-PAGE (FIG. 5) and reacted with antiserum to the human lymphocyte MAT II, to the tryptic peptides, and to the recombinant MAT II β subunit protein. More important, the fact that the cloned protein lowered the Km (L-Met) of the recombinant human MAT II α2 subunit from 80 μM to 34 μM, confirms the previously described regulatory function of the MAT II β subunit (De La Rosa et al. (1992) J. Biol. Chem. 267, 10699–704; LeGros et al. (1997) J. Biol. Chem. 272, 16040–7).

Detailed kinetic analysis of MAT II from human leukemic cells expressing both the α and β subunits of the enzyme revealed strong regulation of enzyme activity by its products, Pi, PPi and AdoMet (Kotb, M., and Kredich, N. M. (1985) J. Biol. Chem. 260, 3923–30; Kotb, M., and Kredich, N. M. (1990) Biochim. Biophys. Acta 1039(2), 253–60). Specifically, the activity of the enzyme was inhibited by almost 2-fold in the presence of 25 μM AdoMet, and by 3-fold in the presence of 25 μM AdoMet and 30 μM PPi.

In 1995, De La Rosa reported that the α2 subunit was responsible for the catalytic activity of MAT whereas the β subunit lacked activity. However, the present Laboratory Examples revealed that recombinant MAT α2 expressed in E. coli had a Km for L-Met of 80 μM compared to a Km of 4 μM in leukemic cells or 20 μM in resting lymphocytes. These observations suggested that MAT II β subunit can have regulatory properties.

The disappearance of the β subunit was accompanied by a change in MAT kinetic properties with the MAT II α2/α2' enzyme form exhibiting a 3-fold higher Km for L-Met and more importantly, showing resistance to feed back product inhibition by AdoMet, and resulting in a 5–6-fold increase in intracellular AdoMet levels (LeGros et al. (1997) J. Biol. Chem. 272, 16040–7). The data presented here, as well as in accompanying Examples 8–13 provide direct evidence that confirm the regulatory role of the β subunit of MAT II.

Figure 9:
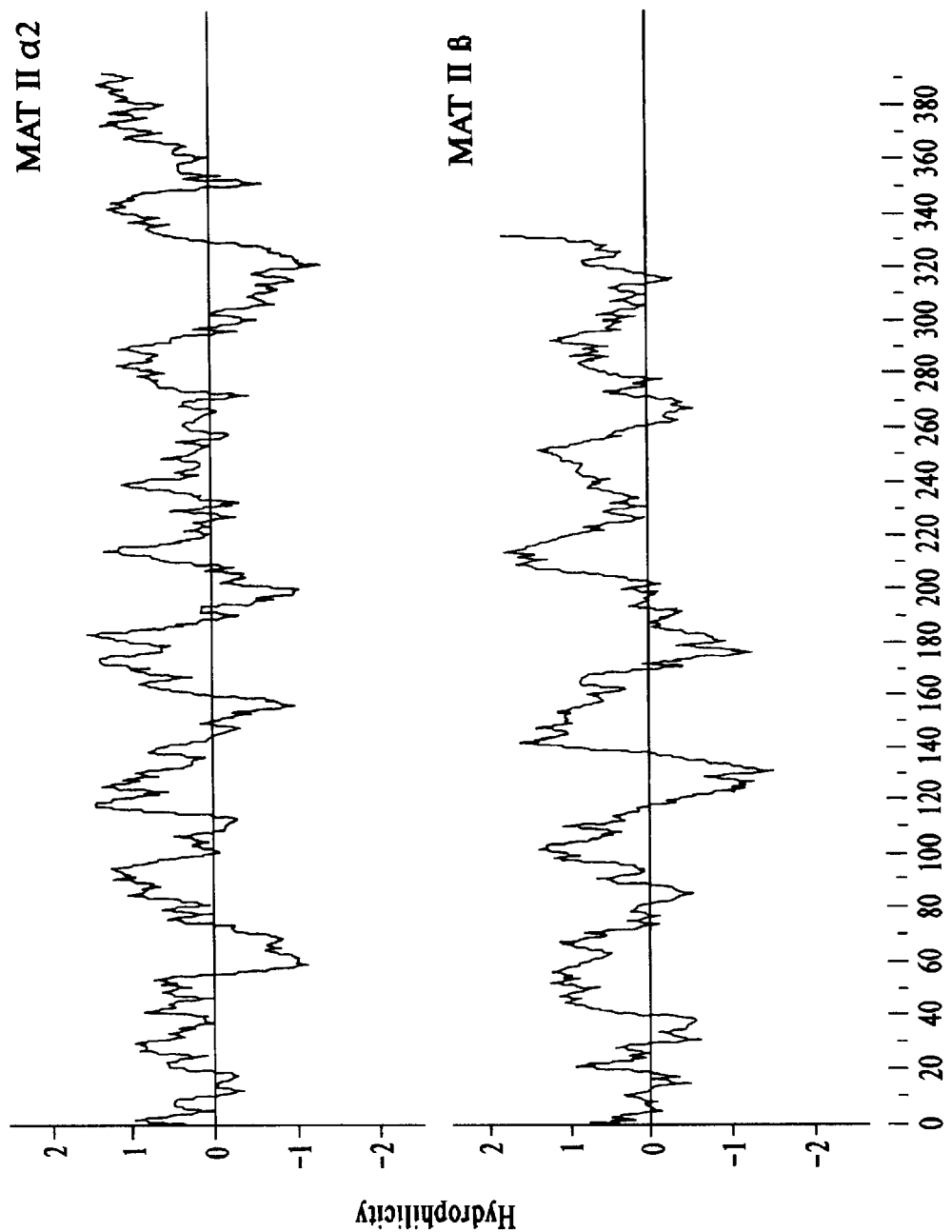
FIG. 9 depicts the hydropathy profile of the human MAT II α2 and β subunits, analyzed by the Kyte-Doolittle plot. The amino acid sequence of the MAT II α subunit, based on previously reported sequence, and the amino acid sequence of the MAT II β subunit, shown in FIG. 8, were analyzed on the Biological Information Resource 2.0 Website, which includes tools for calculating and plotting the hydrophilicity/hydrophobicity of a protein.

The ORF for the MAT II β subunit, which begins with the Met-Val sequence, encodes for a 334 amino acid protein and in concordance with the calculated molecular weight, the recombinant protein migrates on SDS-PAGE as 38-kDa protein. Thus the MAT II subunit, unlike the α2 subunit, migrates at its expected molecular size. The MAT II holoenzyme is known to be very hydrophobic inasmuch as it binds very strongly to phenyl-sepharose columns and can only be eluted with 40% DMSO (Kotb, M., and Kredich, N. M. (1985) J. Biol. Chem. 260, 3923–30). The Kyte-Doolittle hydrophobicity plots of human MAT II β subunit protein revealed two prominent hydrophobic segments; whereas, the α2 subunit has three minor and one major hydrophobic segment, as shown in FIG. 9. It is contemplated that the oligomerization of the MAT II α2 and β subunits is responsible for the strong hydrophobic property of the enzyme.

The sequence of MAT II β subunit represents a unique sequence that has not been previously described for any organism studied to date. The sequence of the β subunit cDNA was identical for Jurkat T cells, MOLT-4 cells, and PBMC from different individuals. Thorough analysis of this sequence against sequences available in various protein and DNA databases failed to detect significant similarities with any other protein.

The presence of the β subunit was detected in human erythrocytes, lymphocytes, bovine brain, Ehrlichs ascites tumor and calf thymus (Kotb, M., and Kredich, N. M. (1985) J. Biol. Chem. 260, 3923–30; Mitsui et al. (1988) J. Biol. Chem. 263, 11211–6). Inasmuch as antibodies to the β subunit did not react with any E. coli protein, it appears that these bacteria lack this subunit. Similarly, applicants were unable to detect the β subunit in yeast cell extracts.

Laboratory Examples 8–13

Expression and Functional Interaction of the Catalytic and Regulatory Subunits of Human Methionine Adenosyltransferase (Mat Ii) in Mammalian Cells Methionine (AdoMet), the active form of the human MAT II isozyme comprises catalytic α2 and regulatory β subunits. The aim of these Examples was to investigate the interaction and kinetic behavior of MAT II subunit proteins in mammalian cells. Cos-1 cells were transiently transfected with pTargeT™ vector harboring full-length cDNA that encodes for the MAT II α2 or β subunits. Expression of the His-tagged rα2 subunit in Cos-1 cells markedly increased MAT II activity and resulted in a shift in the Km for L-Met from 16 μM (endogenous MAT II) to 70 μM (r α2), with the apparent existence of 2 kinetic forms of MAT in transfected Cos-1 cell extracts.

By contrast, expression of the r β subunit had no effect on the Km for L-Met of the endogenous MAT II, while it did cause an increase in endogenous MAT specific activity.

Co-expression of both r α2 and r β subunits resulted in a significant increase of MAT specific activity with the appearance of a single kinetic form of MAT (Km=20 μM). The rMAT II α2 and r β subunit associated spontaneously either in cell free system or in Cos-1 cells co-expressing both subunits. Analysis of Ni-agarose purified His-tagged r α2 subunit from Cos-1 cell extracts showed that the β subunit co-purified with the α2 subunit. Furthermore, the α2 and β subunits co-migrated in native polyacrylamide gels.

Together the data provide evidence for α2 and β MAT subunit association. In addition, the β subunit regulated MAT II activity by reducing its Km for L-Met from 70 μM to 20 μM, and by rendering the enzyme more susceptible to feedback inhibition by AdoMet. Thus, it is contemplated that differential expression of MAT II β subunit is a mechanism by which MAT activity can be modulated to provide different levels of AdoMet that can be required at different stages of cell growth and differentiation.

Laboratory Example 8

Cell Culture

The Cos-1 cells (African green monkey kidney fibroblasts, ATCC CRL 1650) were cultured in Dulbecco's modified Eagle's medium (Gibco-BRL, Grand Island, N.Y.) supplemented with 10% heat-inactivated fetal bovine serum (Atlanta Biologicals, Atlanta, Ga.) and 10 mM L-glutamine (Celigro™, Celigenix, Freiberg, Germany).

Laboratory Example 9

Cloning of Mat II α2 and β Subunits cDNA Into Mammalian Expression Vectors

The full-length cDNA encoding human lymphocyte (HuLy) MAT II α2 protein (De La Rosa et al. (1995) J. Biol. Chem. 270:21860–8) and (LeGros et al. (1999) Submitted) was cloned into the pQE30 vector (Qiagen) designed to express protein with N-terminal 6-histidine (His) tag followed by an enterokinase (EK) site to allow removal of the tag. The HuLy MAT II β cDNA was cloned into the same vector without the poly-histidine or the EK site (LeGros et al. (1999) Submitted). The cloned cDNA encoding rα2 and r β subunits were transferred from the pQE30 vector to the mammalian expression pTargeT™ vector (Promega) to generate pTargeT™/MAT2A and pTargeT™/MAT2B, respectively. Briefly, primers were designed to amplify the full-length cDNA encoding either the α2 or the β subunits from the pQE30 vector. Amplification was done using Taq polymerase (Promega) and pfu (Stratagene) in the ratio of 5:1, and the amplified product containing A-overhang was separated on 1% agarose gel in 0.5xTBE, purified, ligated into the mammalian expression vector, pTargeT™, and used to transform *E. coli* strain JM109 competent cells by heat shock.

Positive colonies were selected and subcultured, and plasmid DNA were purified (Qiagen). The purified plasmid DNA were tested for the presence of the cloned inserts of the correct size and orientation by both PCR and EcoRI restriction site analysis. DNA from 6 colonies containing the proper insert in the right direction were subjected to manual sequencing of the entire cDNA in both directions using DNA cycle sequencing reagents (Promega) and the sequence was compared to the previously confirmed cDNA sequence for the α2 (De La Rosa et al. (1995) J. Biol. Chem. 270:21860–68) and for the β subunit sequence (LeGros et al. (1999) Submitted ) to ensure that no mutations were introduced during amplification. One colony for either the α2 or the β subunits with the proper insert was grown for large-scale preparation of vector (Qiagen).

Laboratory Example 10

Transfection of Cos-1 Cells

Transfection of Cos-1 cells with pTargeT™/MAT2A or pTargeT™/MAT2B was done using the cationic lipid reagent, Transfast™ (Promega). Preliminary experiments were carried out to optimize the transfection conditions. Typically, $1.5 \times 10^6$ cells were plated in 100 mm dish one day prior to transfection. For each plate, 15 mg of vector DNA was applied in the ratio of 1:1 to Transfast™ in a protein-free medium for 2 h. For cells co-transfected with both α2 and β vectors, 12 mg DNA from each was used. For each experiment, one untransfected plate served as a normal control, and a second plate was transfected with the pTargeT™ vector only (mock-transfected cells). After 48 h, cells were harvested by trypsinization with a solution containing 0.05% trypsin and 0.53 mM EDTA in Hank's balanced salt solution (HBSS, from Cellgro). Trypsinization was stopped by the addition of media supplemented with 10% FCS, cells were pelleted, washed three times in 1 ml HBSS, counted, then resuspended in 1× extraction buffer with protease inhibitors (50 mM Tris, pH 7.4, 100 mM NaCl, 5 mM $MgCl_2$, 4 mM dithiothreitol, 0.1 IU/ml aprotinin, 0.5 mM PMSF and 30 mg/ml soybean trypsin inhibitor). Cells were lysed by three cycles of quick freezing and thawing, and the lysate was clarified by centrifugation at 15,000×g for 10 min at 4° C. If not immediately used, cell extracts were stored at −80° C. Protein assays were performed using the bicinchoninic acid reagent (Sigma) following the manufacturer instructions.

Laboratory Example 11

Analysis of Expressed Mat II α2 and β Subunits a. Western Blot

Extracts from normal, mock-transfected, and (α2- or β-transfected Cos-1 cells were prepared as described above, and 40 mg protein from each cell extract were loaded onto 7.5% SDS-polyacrylamide gel (SDS-PAGE) after dilution 1:1 in 2× sample loading buffer (60 mM Tris, pH 6.8, 4% SDS, 5% 2-mercaptoethanol and 5% glycerol) and boiling in a water bath for 5 min. For 17×17 cm gel size, electrophoresis was started at 100 volts and after the tracking dye has left the stacking gel the current was kept constant at 30 mA for the remainder of the run. The gel was electroblotted onto a nitrocellulose membrane (BioRad, Richmond, Calif.) for 1.5 h at 400 mA. After blocking overnight in 6% non-fat dry milk in Tris-buffered saline, the blot was sequentially incubated with primary rabbit anti-α2 or anti-β antibodies prepared as previously described (LeGros et al. (1999) Submitted; De La Rosa et al. (1991) Biochim. Biophys. Acta 1077, 225–32; Kotb et al. (1990) Biochim. Biophys. Acta 1040, 137–44) followed by a secondary goat anti-rabbit antibody conjugated to horse radish peroxidase (Southern Biotechnology Associates, Inc., Birmingham, Ala.). The signal was initiated by the chemiluminescence reagents (ECL®, Amersham Pharmacia Biotech AB, Uppsala, Sweden) and detected using X-Omat™ film from Kodak ((Eastman Kodak Company, Rochester, N.Y.). Molecular weight markers and recombinant MAT II (rMAT II) subunit proteins purified for *E. coli* extracts were used to determine the migration of expressed α2 and β subunits.

b. Kinetic Properties of Expressed Mat II Subunits

MAT activity in cell extracts was assayed as previously described (Kotb, M., and Kredich, N. M. (1985) J. Biol.

Chem. 260, 3923–30). The assay mixture contained 5 mM ATP, 50 mM KCl, 15 mM $MgCl_2$, 0.3 mM EDTA, 4 mM DTT in 50 mM TES buffer, pH 7.4. The concentration of L-Met was varied between 2 mM–80 mM using $^{14}$C-L-Met (57.9 mCi/mmol) to a concentration of up to 20 mM, and supplementary with cold L-Met for higher concentrations.

Laboratory Example 12

Analysis of Expressed Mat Ii-α2 and -β Subunit Interaction

Experiments were designed to determine whether the expressed α2 and β subunits of MAT II associate and if the association alters the kinetic properties of the enzyme. Two methods were used to detect subunit association.

b. Analysis by Native Gel Electrophoresis

Cell extracts were separated on 6% polyacrylamide gel in 1.5 M Tris, pH 8.8 under native conditions (without SDS). After blotting onto nitrocellulose membrane, the blots were probed with anti-α2 antibody, stripped, then reprobed with anti-β antibody. Overlapping signals were taken as an evidence of co-migration of both subunits.

c. Analysis by Ni-Agarose Beads Affinity Capture

The association between the His-tagged α2 subunit and the non-tagged β subunit was analyzed by affinity purification on Ni-agarose beads (Qiagen). In a 15-ml tube, 2 ml of the 50% Ni-agarose slurry was spun down at 1000 rpm for 2 min then the pellet was equilibrated with a buffer containing 300 mM NaCl and 50 mM sodium phosphate, pH 8. Cellular extract containing about 10 mg proteins was added and incubated for 30 min at 4° C. with mixing on a vertical rotator. The gel was then loaded into the column and allowed to settle. The column was washed several times with 5 ml of the equilibration buffer till the $A_{280}$ reading on the through buffer became undetectable. Bound proteins were eluted with 5 ml of 300 mM imidazole, dialyzed against 20 mM Tris, pH 8 and lyophilized. Lyophilized proteins were reconstituted in 25 mM Tris buffer pH 8, and the protein content was assayed by the bicinchoninic acid reagent (Sigma). Two microgram proteins were analyzed by SDS-PAGE as described above.

Laboratory Example 13

Separation of Recombinant and Endogenous Mat II Subunits from Cos-1 Cell Extracts and Determination of Adomet Feedback Inhibition of Enzyme Activity Experiments were designed to test the effect of β subunit on the inhibitory action of AdoMet on the enzymatic activity of the α2 subunit. However, due to association of r α2 with endogenous β as well as the association of the r β with the endogenous α2 protein, it was necessary to purify the subunits away from each other and to test them separately and in combination for kinetic properties and inhibition by AdoMet.

Protein extracts from COS-1 cells co-expressing α2 and β subunits was fractionated on Ni-agarose column (Qiagen) as described above. The purified proteins were loaded onto preparative 7.5% SDS-PAGE and after separation was complete, protein bands were visualized by impregnation in cold 300 mM KCl, and the α2 or β bands were excised, and proteins were electroeluted from the gel separately into Tris-glycine buffer, pH 8, and dialyzed against 10 mM ammonium bicarbonate then lyophilized. The lyophilized subunits were reconstituted and MAT assay was performed at 20 mM L-Met for α2 subunit alone or α2 plus β subunits (combined at a molar ratio of 1:1) in the absence, or the presence of 25–50 μM AdoMet.

Results of Laboratory Examples 8–13

Detection and Kinetic Analysis of rMat IIα2 Subunit Expressed in Cos-1 Cells

Cos-1 cells were transfected with pTargeT™/MAT2A plasmid DNA. Protein extracts from untransfected, mock-transfected, and MAT2A-transfected cells were analyzed by Western blots. In untransfected and mock-transfected cells, small amounts of endogenous α2, α2' and β subunits were detected (FIG. 13, Lanes 1 and 2), however, cells transfected with MAT2A expressed abundant amounts of the r α2 protein which migrated with a higher molecular weight due to the additional N-terminal polyhistidine tag and the enterokinase site (FIG. 13, Lane 3). To study the effect of over-expression of rα2 on MAT kinetics, extracts from untransfected and transfected cells were assayed for MAT activity at different concentrations of L-Met ranging from 2 to 80 mM. Transfection with pTargeT™/MAT2A caused 3–4 fold increase in MAT activity, compared to untransfected cells (see FIG. 19 below). In addition, expression of the rα2 affected the enzyme Km for L-Met. MAT II in untransfected and mock-transfected cells had Km of 15.6 and 16.1 mM, respectively (FIG. 14A and FIG. 14B), which are within the range found in resting human lymphocytes (De La Rosa et al. (1992) J. Biol. Chem. 267, 10699–704; LeGros et al. (1997) J. Biol. Chem. 272, 16040–47). However, in cells expressing high levels of rMAT II α2 protein, two kinetic forms with Km for L-Met of 15.1 and 70 μM could be discerned (FIG. 14C).

Detection and Kinetic Analysis of Mat II β Expressed in Cos-1 Cells

Cos-1 cells were transfected with pTargeT™/MAT2B plasmid DNA, and the protein extracts from untransfected or transfected cells were analyzed by Western blots. Cells transfected with pTargeT™/MAT2B expressed higher amounts of the rβ protein compared to untransfected cells (Inset, FIG. 15). Expression of MAT II β protein did not significantly affect the kinetic behavior of MAT II in normal cells (FIG. 15) inasmuch as the Km for L-Met was 20 μM; however, expression of rβ caused ~2-fold increase in the MAT activity at different concentrations of L-Met (see FIG. 19 below).

Co-expression of Mat IIα2 and β Subunits.

Cos-1 cells were co-transfected with pTargeT™/MAT2A and pTargeT™/MAT2B plasmid DNA, and the protein extracts from untransfected and transfected cells were analyzed by Western blots. As shown in FIG. 16, cells co-transfected with both vectors expressed abundant amounts of the rα2 and rβ proteins compared to untransfected or mock-transfected cells.

Evidence for Association of Mat IIα2 and β Subunits.

The association between α2 and β subunits was assessed by different means. First, extracts from Cos-1 cells co-transfected with vectors encoding α2 and β subunits were subjected to PAGE gel separation under native conditions and blotted onto nitrocellulose membrane that was sequentially probed with antibodies to r α2 followed by antibodies to β subunit with stripping in between probing. Both antibodies recognized the same bands on the transblot (FIG. 17) which indicated co-migration of both subunits under native conditions.

Second, applicants took advantage of the selective His-tag on the r α2 subunit but not on the β subunit and used Ni-agarose to affinity purify the α2 subunit from extracts of Cos-1 cells co-expressing r α2 and rβ subunits to test whether the β subunit is associated with it. As shown in FIG. 18A, analysis of the protein purified on Ni-agarose columns by SDS-PAGE shows that the rβ subunit co-purified with the rβ 2 subunit. Interestingly, when extracts from cells individually expressing r α2 or rβ proteins were simply mixed in a protein ratio of 1:1, the α2 and β subunits also associated and co-purified on Ni-agarose column (FIG. 18B) indicating spontaneous association of these proteins.

Together, the data provide evidence that the r α2 subunit associates with the β subunit of MAT II. Interestingly, some of the native α2 and α2' subunits were also captured by the His-tagged r α2 protein suggesting heterologous oligomerization of α2, α2' subunits with each other as well as with the β subunit.

Kinetic Analysis of Mat in Extracts from Cos-1 Cells Co-expressing rMat II α2 and Rβ Subunits MAT activity was assayed in extracts of Cos-1 cells expressing rα2 only, or co-expressing both r α2 and rβ subunits. MAT activity was increased by approximately 5-fold in the co-transfected cells compared to untransfected or mock-transfected cells, as shown in FIG. 19. Further, co-expression of rβ subunit caused an increase in MAT activity over that which was found in cells transfected with r α2 alone. The Km for L-Met in extracts from Cos-1 cells co-expressing both subunits indicated the presence of a single kinetic form of MAT II with Km of 20.8 μM, as shown in FIG. 20.

Next it was investigated whether the β subunit alters the feedback inhibition by the enzyme product, AdoMet. The activity of purified r α2 with and without rβ was tested in the absence or presence of AdoMet. To rule out the possible association of either r α2 or rβ subunits with the endogenous MAT II subunits, we performed Ni-agarose column purification of extracts from Cos-1 cells co-transfected with both subunits, separated the products on SDS-PAGE, and excised the α2 and β bands from the gel, electroeluted the protein and purified each subunit separately. The purified subunits were mixed in equimolar ratio, and assayed for MAT activity in the presence and absence of AdoMet. While the addition of the β subunit significantly increased the catalytic activity of r α2 by almost 2-fold (FIG. 21), the presence of the β subunit rendered the enzyme more susceptible to AdoMet inhibition with more than 2-fold increase in the inhibitory effect of AdoMet seen when α2 and β were combined.

Discussion of Laboratory Examples 8–13

The essential role of AdoMet in cellular metabolism is underscored by the fact that it participates in as many reactions as ATP, and regulates the function of many key molecules and pathways (Tabor, C. W., and Tabor, H. (1984) Adv. Enzymol. Relat. Areas Mol. Biol. 56, 251–82; Kotb, M., and Geller, A. M. (1993) Pharmacol. Ther. 59, 125–43; Mato et al. (1997) Pharmacol. Ther. 73, 265–80; Finkelstein et al. (1975) Biochem. Biophys. Res. Commun. 66, 81–87). It follows that understanding the regulation of synthesis of this pivotal compound is important. AdoMet is synthesized by MAT, which exists in mammalian cells in at least 2 isozymes; MAT I/III are confined to hepatic tissue and MAT II is found in all tissues (Kotb, M., and Geller, A. M. (1993) Pharmacol. Ther. 59,125–43; Mato et al. (1997) Pharmacol. Ther. 73, 265–80; Finkelstein et al. (1975) Biochem. Biophys. Res. Commun. 66, 81–87). An emerging theme in the regulation of MAT activity in mammalian cells is that the differential oligomerization of the enzyme subunits can profoundly alter the enzyme physical properties, activity, and kinetic regulation.

For example, the α1 catalytic subunit of the hepatic form of MAT exists either as a dimer (MAT III) or a tetramer (MAT I). This difference in oligomeric forms results in profound changes in the hydrophobic properties of the enzyme; MAT I is non-hydrophobic whereas MAT III is strongly hydrophobic (Hoffman, J. L. (1983) Methods Enzymol. 94, 223–8; Mingorance et al. (1997) Int. J. Biochem. Cell. Biol. 29, 485–91). Furthermore, MAT I is inhibited, while MAT III is activated by AdoMet, and the Km for L-Met for these two forms is 3–14 μM and 100–200 μM, respectively (Sullivan, D. M., and Hoffman, J. L. (1983) Biochemistry 22, 1636–41; De La Rosa et al. (1992) J. Biol. Chem. 267, 10699–704; Suma et al. (1986) J. Biochem. (Tokyo) 100, 67–75; Pajares et al. (1992) FEBS Lett. 309, 1–4). Although several elegant studies (Mato et al. (1994) Adv. Exp. Med. Biol. 368, 113–7; Mingorance et al. (1997) Int. J. Biochem. Cell. Biol. 29, 485–91; Pajares et al. (1992) FEBS Lett. 309, 1–4; Corrales et al. (1990) Hepatology 11, 216–22; Corrales eta!. (1991) Hepatology 14, 528–33) have described means for the interconversion of MAT I and III, the physiologic relevance of the need to have these two forms of MAT in the liver remains unclear.

Unlike the hepatic forms of MAT, MAT II that is present in all mammalian tissues, comprises non-identical subunits α2 and β (Kotb, M., and Kredich, N. M. (1985) J. Biol. Chem. 260: 3923–30). Previously it has been reported that the α2 subunit is catalytic, while the properties of the β subunit were not as apparent (Kotb, M., and Kredich, N. M. (1985) J. Biol. Chem. 260: 3923–30; De La Rosa et al. (1992) J. Biol. Chem. 267: 10699–704; De La Rosa et al. (1995) J. Biol. Chem. 270:21860–68; LeGros et al. (1997) J. Biol. Chem. 272: 16040–47; LeGros et al. (1999) Submitted). To directly assess the role of each MAT subunit in enzyme activity, these subunits were expressed in mammalian cells to ensure proper post-translational modification to study whether they associate and determine the consequence of this association on the kinetic properties of MAT II.

In Examples 8–13, evidence is thus provided that the α2 and β subunits of MAT II associate spontaneously, and that this association alters the kinetic properties of the enzyme. Ni-agarose capture purification of the His-tagged rα2 subunit from Cos-1 cells co-expressing rα2 and rβ showed that the β subunit co-purified with the α2 subunit. Interestingly, rα2 oligomerized also with the endogenous α2 and α2' subunits suggesting heterologous oligomerization of α2, α2' and β subunits of MAT II. It is noteworthy that in cells expressing abundant amounts of rα2 and low levels of endogenous β subunit two kinetic forms of MAT II with Km's for L-Met of 15 and 70 μM were detected.

By contrast, in cells co-expressing rα2 and rβ, only one kinetic form of MAT II is detected with a Km for L-Met of 20 mM. It is envisioned that the lower Km form represents α2/α2'β MAT II, and the higher Km form found in cells overexpressing rα2 protein represents homo-oligomeric α2 subunits which are in great excess of the endogenous β subunit. This conclusion is consistent with previous findings that the Km for rα2 is 80 μM (De La Rosa et al. (1995) J. Biol. Chem. 270:21860–68), and that in physiologically stimulated PBMCs where the expression of the β subunit is downregulated and only the α2 subunit is expressed, the Km for L-Met shifts from 20 μM to 55–67 μM (LeGros et al. (1997) J. Biol. Chem. 272: 16040–47).

Together, the data provides evidence that the MAT II β subunit associates with the α2 subunit, and lowers the Km for L-Met. The association between the α2 and β subunit does not appear to require metabolically active cells as it occurs spontaneously when purified r α2- and rβ protein are mixed. However, the molar ratio of each subunit in the holoenzyme remains to be determined. It is contemplated, based on the data presented herein, that α2 can exist in homo-oligomers (dimers or tetramers) or as α2β hetero-oligomers. The relative ratio of either form would depend on the relative molar concentration of α2 to β subunits, which can vary at different stages of lymphocyte activation. It is thus contemplated that this can be a mechanism by which MAT II can change its kinetic properties to synthesize different amounts of AdoMet because on addition to its effect on lowering the Km for L-Met, the β subunit renders the enzyme more sensitive to AdoMet feedback inhibition.

The findings in this study provide an explanation for the observation that downregulation of β subunit expression in activated lymphocytes results in a 5-fold higher AdoMet levels in these cells. In these physiologically stimulated cells, the β subunit disappears after 72 hours, and the α2/α2' subunits retain MAT activity with a Km for L-Met of 55–67 mM, and are at least 2-fold more resistant to AdoMet feedback inhibition. As a result, there is an accumulation of higher amounts of intracellular AdoMet reaching up to 100 μM compared to resting lymphocyte levels of 20 mM. It is also interesting to note that certain methyltransferases, including specific DNA methyltransferases that have a relatively high Km for AdoMet (Fujioka, M. (1992) Int. J. Biochem. 24: 1917–24; Roth et al. (1998) J. Biol. Chem. 273: 17333–42) might be more active at the concentration attained in cells expressing only MAT II α2 subunits.

In conclusion, the data reported in Examples 8–13 show that the association of MAT II α2 and β subunits alters the kinetic and regulatory properties of the enzyme. This mode of regulation is implicated in adjusting the levels of AdoMet to meet the cellular requirements in different stages of differentiation. This mode of regulation is also implicated in the regulation of expression of certain genes and/or the function of gene products.

REFERENCES

The publications and other materials used herein to illuminate the background of the invention, and in particular cases, to provide additional details respecting the practice, are incorporated herein by reference, and for convenience, are referenced by numeral in the following text, and respectively grouped according to the numerals in the appended list of references.

Adelman et al. (1983) DNA 2:183.
Ahuja et al., Cancer Res. (1998) 23:5489–94.
Alvarez, L., et al. (1993) Biochem. J. 293, 481–6
Ausubel et al. (1992) Current Protocols in Molecular Biology, (J. Wylie & Sons, N.Y.)
Belinsky et al., Proc. Natl. Acad. Sci. USA (1998) 20:11891–6.
Bitgood et al. (1996) Curr. Biol. 6, 298–304.
Bodanszky, et al., "Peptide Synthesis", John Wiley & Sons, Second Edition, 1976.
Cantoni, G. L. (1953) J. Biol. Chem. 204, 403–416
Chiang, P. K., et al. (1996) FASEB J. 10, 471–80
Corrales, F., et al. (1990) Hepatology 11, 216–22
Crea et al. (1978) Proc. Natl. Acad. Sci. U.S.A, 75:5765.
De La Rosa, J.,et al. (1991) Biochim. Biophys. Acta 1077, 225–32
De La Rosa, J.,et al. (1992) J. Biol. Chem. 267, 10699–704
De La Rosa, J., et al. (1995) J. Biol. Chem. 270:21860–8
Eichenlaub et al. (1979) J. Bacteriol 138:559–566.
Fields et al., Int. J. Peptide Protein Res., 35:161–214, 1990
Finkelstein, J. D., et al. (1975) Biochem. Biophys. Res. Commun. 66, 81–7
Fitzgerald, M., and Shenk, T. (1981) Cell 24, 251–260
Fujioka, M. (1992) Int. J. Biochem. 24, 1917–24
Gil, B., et al. (1996) Hepatology 24, 876–81
Hoffman, J. L. (1983) Methods Enzymol. 94, 223–8
Hopp, U.S. Pat. No. 4,554,101.
Horikawa, S., and Tsukada, K. (1991) Biochem. Int. 25, 81–90
Horikawa, S., et al. (1990) J. Biol. Chem. 265, 13683–6
Howell et al. (1988) Antibodies A Laboratory Manual, (Cold Spring Harbor Laboratory).
Klapper, M. (1977) Biochim. Biophys. Acta 78, 1018–1024
Kotb, M., and Kredich, N. M. (1985) J. Biol. Chem. 260, 3923–30
Kotb, M., Mudd, S. H., Mato, J. M., Geller, A. M., Kredich, N. M., Chou, J. Y., and Cantoni, G. L. (1997) Trends Genet. 13, 51–2
Kotb, M., and Geller, A. M. (1993) Pharmacol. Ther. 59, 125–43
Kotb, M., and Kredich, N. M. (1990) Biochim. Biophys. Acta 1039(2), 253–60
Kotb, M., and Kredich, N. M. (1985) J. Biol. Chem. 260, 3923–30
Kotb, M., et al. (1990) Biochim. Biophys. Acta 1040, 137–44
Kotb, M., et al. (1997) Trends Genet. 13, 51–2
Kozak, M. (1989) J. Cell Biol. 108, 229–241
Kyte et al. (1982) J. Mol. Biol. 157:105.
Langkamp-Henken, B., et al. (1994) Biochim. Biophys. Acta 1201, 397–404
LeGros, H. L., Jr., Geller, A. M., and Kotb, M. (1997) J. Biol. Chem. 272, 16040–7
Liau, M. C., et al. (1998) Mol. Genet. Metab. 63, 26–30
Maniatis et al. (1978) Cell 15:687–701.
Mato, J. M., et al. (1994) Adv. Exp. Med. Biol. 368, 113–7
Mato, J. M., et al. (1997) Pharmacol. Ther. 73, 265–80
McOmie (1973) Protective Groups in Organic Chemistry, Plenum Press, New York,
Meienhofer, Hormonal Proteins and Peptides, Vol. 2, p. 46, Academic Press, New York, (1983)
Merrifield (1969) Adv Enzymol 32:221–96.
Messing et al. (1981) Third Cleveland Symposium on Macromolecules and
Mingorance, J., et al. (1997) Int. J. Biochem. Cell. Biol. 29, 485–91
Mitsui, K., Teraoka, H., and Tsukada, K. (1988) J. Biol. Chem. 263, 11211–6
Mudd, S. H. (1973) The Adenosyltransferases, Third Edition Ed. The Enzymes, Group Transfer (Part A) (Bayer, P. D., Ed.), III,
Mudd, S. H., Levy, H. L., and Skovby, F. (1995) Disorders of transsulfuration, 7th Ed. The Molecular and Metabolic Basis of Inherited Diseases (Scriver, C. R., Beaudet, A. L., Sly, W. S., and Valle, D., Eds.), McGraw-Hill Inc., New York.
Needleman et al. (1970) J. Mol. Biol. 48:443.
Ochman et al. (1990) Amplification of flanking sequences by Inverse PCR, in PCR protocols: a Guide to Methods and Applications (Innis et al., eds.), pp. 219–227. Academic Press, San Diego, Calif.
Oden, K., and Clarke, S. (1983) Biochemistry 22, 2978–2986
Okada, G., Teraoka, H., and Tsukada, K. (1981) Biochemistry 20, 934–40
Pajares, M. A., et al. (1992) FEBS Lett. 309, 1–4
Pissowotzki, K., et al. (1991) Mol. Gen. Genet. 231, 113–123
Proudfoot, N. J., and Brownlee, G. G. (1976) Nature 263, 211–214 Recombinant DNA, Editor A. Walton, (Elsevier, Amsterdam).
Roth, M., et al. (1998) J. Biol. Chem. 273, 17333–42
Sakata, S. F., et al. (1993) J. Biol. Chem. 268, 13978–86
Sambrook et al. (1989) Molecular Cloning: A Laboratory Manual (Cold Spring Harbor Laboratory Press, Cold Spring Harbor, N.Y.).
Schroder et al., "The Peptides", Vol. 1, Academic Press (New York) (1965).
Smith et al., Adv. Appl. Math. 2:482 (1981).
Steward et al. (1969) Solid Phase Peptide Synthesis, W.H. Freeman Co., San Francisco.
Sullivan, D. M., and Hoffman, J. L. (1983) Biochemistry 22, 1636–41
Suma, Y., Shimizu, K., and Tsukada, K. (1986) J. Biochem. (Tokyo) 100, 67–75
Tabor, C. W., and Tabor, H. (1984) Adv. Enzymol. Relat. Areas Mol. Biol. 56, 251–82
U.S. Pat. No. 5,786,152
U.S. Pat. No. 5,120,535
U.S. Pat. No. 4,769,331
U.S. Pat. No. 5,352,660
U.S. Pat. No. 5,489,742
U.S. Pat. No. 5,780,436
U.S. Pat. No. 5,776,902
U.S. Pat. No. 5,399,346
U.S. Pat. No. 5,326,902
U.S. Pat. No. 5,734,033
U.S. Pat. No. 5,741,957
U.S. Pat. No. 5,286,634
U.S. Pat. No. 5,646,008
U.S. Pat. No. 5,693,488
U.S. Pat. No. 5,770,609
U.S. Pat. No. 5,753,687
U.S. Pat. No. 5,723,593
U.S. Pat. No. 5,436,288
U.S. Pat. No. 2,868,691
U.S. Pat. No. 3,095,355
U.S. Pat. No. 4,196,265
U.S. Pat. No. 4,244,946
U.S. Pat. No. 4,683,202
U.S. Pat. No. 4,686,283
U.S. Pat. No. 4,736,866
U.S. Pat. No. 5,580,979
U.S. Pat. No. 5,162,215
U.S. Pat. No. 5,234,933
U.S. Pat. No. 5,279,833
U.S. Pat. No. 5,648,061
U.S. Pat. No. 5,583,103
U.S. Pat. No. 5,589,375
U.S. Pat. No. 5,651,964
U.S. Pat. No. 5,643,567
U.S. Pat. No. 5,739,278
U.S. Pat. No. 5,550,316
U.S. Pat. No. 5,573,933
U.S. Pat. No. 5,641,484
U.S. Pat. No. 5,625,125
U.S. Pat. No. 5,614,396
U.S. Pat. No. 5,624,816
U.S. Pat. No. 5,837,479
U.S. Pat. No. 5,627,158
U.S. Pat. No. 5,645,999
Ubagai, T., et al. (1995) J. Clin. Invest. 96, 1943–7
Wetmur & Davidson (1968) J. Mol. Biol. 31:349–370.
WO 96/40276
WO 93/25521
Zimmer et al., Peptides 1992, pp. 393–394, ESCOM Science Publishers, B.V. 1993.

It will be understood that various details of the invention can be changed without departing from the scope of the invention. Furthermore, the foregoing description is for the purpose of illustration only, and not for the purpose of limitation—the invention being defined by the claims.

What is claimed is:

1. An isolated and purified polynucleic acid encoding a methionine adenosyltransferase II (MAT II) β subunit polypeptide capable of modulating methionine adenosyltransferase II (MAT II) catalytic activity, wherein the polynucleic acid is selected from the group consisting of:
   (a) a polynucleic acid encoding a polypeptide comprising of an amino acid sequence at least 90% identical to an amino acid sequence selected from the group consisting of SEQ ID NOs.: 17, 19, 21, 23, and 25;
   (b) a polynucleic acid having a sequence selected from the group consisting of SEQ ID NOs.: 16, 18, 20, 22, and 24; and
   (c) a polynucleic acid capable of hybridizing to a polynucleic acid of (a) or (b) above under high stringency conditions with a washing step in 0.1×SSC at 65° C., or a polynucleic acid that is fully complementary to (a), (b) or (c).

2. The polynucleic acid of claim 1, wherein the encoded polypeptide comprises a human methionine adenosyltransferase II (MAT II) β subunit polypeptide.

3. The polynucleic acid of claim 1, wherein the encoded polypeptide comprises an amino acid sequence selected from the group consisting of SEQ ID NOs: 17, 19, 21, 23, and 25.

4. The polynucleic acid of claim 1, comprising a polynucleic acid selected from the group consisting of SEQ ID NOs: 16, 18, 20, 22, 24 and a sequence fully complementary to one of SEQ ID NOs: 16, 18, 20, 22 and 24.

5. The polynucleic acid of claim 1, wherein the polynucleic acid comprises DNA.

6. The polynucleic acid of claim 1, wherein the polynucleic acid is operably linked to a promoter.

7. A recombinant host cell comprising the polynucleic acid of claim 1.

8. The recombinant host cell of claim 7, wherein the host cell is a prokaryotic cell.

9. The recombinant host cell of claim 7, wherein the host cell is a eukaryotic cell.

10. A method of producing a methionine adenosyltransferase II (MAT II) β subunit polypeptide, comprising: transforming a cell with the polynucleic acid of claim 1 and culturing said cell under conditions suitable for the expression of said polypeptide.

11. A method of detecting in a sample an RNA that encodes the methionine adenosyltransferase II (MAT II) β subunit polypeptide encoded by the nucleic acid of claim 1, said method comprising:
(a) contacting said sample under hybridizing conditions with the polynucleic acid of claim 1 to form a duplex; and
(b) detecting the presence of said duplex.

12. A method of detecting a messenger RNA transcript that encodes a methionine adenosyltransferase II (MAT II) β subunit polypeptide, the method comprising hybridizing the messenger RNA transcript with the polynucleic acid of claim 1 to form a duplex; and detecting the duplex.

13. A method of detecting a DNA molecule that encodes a methionine adenosyltransferase II (MAT II) β subunit polypeptide, the method comprising hybridizing DNA molecules with the polynucleic acid of claim 1 to form a duplex; and detecting the duplex.

14. An assay kit for detecting the presence, in biological samples, of a polynucleotide acid encoding a methionine adenosyltransferase II (MAT II) β subunit polypeptide, the kit comprising a container that contains the polynucleic acid of claim 1.

15. A method for modulating methionine adenosyltransferase II (MAT II) biological activity in a cell, said method comprising:
(a) delivering to the cell an effective amount of a DNA molecule comprising a polynucleotide that encodes a methionine adenosyltransferase II (MAT II) β subunit polypeptide that modulates methionine adenosyltransferase II (MAT II) biological activity, the polynucleotide selected from the group consisting of:
(i) a polynucleic acid encoding a polypeptide comprising an amino acid sequence at least 90% identical to an amino acid sequence selected from the group consisting of SEQ ID NOs.: 17, 19, 21, 23, and 25;
(ii) a polynucleic acid having a sequence selected from the group consisting of SEQ ID NOs.: 16, 18, 20, 22, and 24;
(iii) a polynucleic acid capable of hybridizing to a polynucleic acid of (i) or (ii) above under high stringency conditions with a washing step in 0.1× SSC at 65° C.; and
(b) maintaining the cell under conditions sufficient for expression of said polypeptide.

16. The method of claim 15, wherein the polypeptide comprises a polypeptide selected from the group consisting of SEQ ID NOs: 17, 19, 21, 23, and 25.

17. The method of claim 15, wherein the polynucleotide comprises a polynucleic acid sequence selected from the group consisting of SEQ ID NOs: 16, 18, 20, 22, 24 and a sequence fully complementary to one of SEQ ID NOs: 16, 18, 20, 22 and 24.

18. A recombinant vector comprising a polynucleic acid of claim 1.

19. An isolated and purified polynucleic acid encoding a methionine adenosyltransferase II (MAT II) β subunit polypeptide capable of modulating methionine adenosyltransferase II (MAT II) catalytic activity, wherein the polynucleic acid is selected from the group consisting of:
(a) a polynucleic acid encoding a polypeptide comprising of an amino acid sequence at least 90% identical to an amino acid sequence selected from the group consisting of SEQ ID NOs: 17, 19, 21, 23, and 25;
(b) a polynucleic acid having a sequence selected from the group consisting of SEQ ID NOs: 16, 18, 20, 22, and 24; and
(c) a polynucleic acid capable of hybridizing to a polynucleic acid of (a) or (b) above under high stringency conditions with a washing step in 0.1×SSC at 65° C.

* * * * *

SEQUENCE LISTING

<160> NUMBER OF SEQ ID NOS: 27

<210> SEQ ID NO 1
<211> LENGTH: 2660
<212> TYPE: DNA
<213> ORGANISM: Homo sapiens

<400> SEQUENCE: 1

```
tttgcaaaag aaactccagg attcttgaca gaaagttgtt gggttttggt tttggttttg      60
ttaagtagtt agttctacca atagtttgca aatagaccca ggcttgactg gcaattaacc     120
atgaaacttc tcattgggta ttttcgagac tactacgggg aatcagctac cagctttact     180
gccatgtgga gaactgcacg agattccggg attggaatca aaatgctaat ttaaaaggtc     240
aagtgaagct gctcctcacg ttttggcgtg cctgcgctct ctgcaggcag aagcgaacaa     300
agacccagca agagaaggca gaggctaaga cccatcccgt atctgctctc ctgaaataat     360
tctggagtca tgcctgaaat gccagaggac atggagcagg taagaactag caattcaaga     420
```

```
aatgaagcat tctagagtaa gagatgcttt aaaagcattc cagtgaacgc ctgctaaaac    480
cagaattgtt gtgtaaagaa aatagaaacg ggtgtcattc atttccttaa aacataacct    540
cgggacatgg aagaataagc caactttagt tactgacccg gagaaccagg ttatgaaggg    600
ctcagctaag tctcactagc tgacaataca gaattgcact ttcatttacc attttaaatg    660
caattatgta tataaagttt ctacataaat aaggatttta tctgtagtgt gttcccttcc    720
agatgttctt tgtctttgta tgaattgaat ctgctaacat aacttttagt ttcaggctgc    780
tctcttttaaa tgtatagact tagccaccac acgaagttga atattgtcta tgttaagaat    840
ggcgtttgat tcgcatagac cctaccatca ttaaagaaaa tgattaaaaa ccatatccaa    900
acatatgccc ctagaactgt acccaacttt tacgggaaaa gtatcaagtc agattttcaa    960
aagcagccaa gttaaattct ttctgttcct caagactagg ctgctctgag aatcagaatg   1020
ctaattgcat atgcttgccc ttaaacctgc ttcacgttga agaatgaaga attaattttc   1080
ttttctccca tagaaaggta agattacatc acgtgttgcg actagaaact ttaaaccgaa   1140
ttcccagtta agagaaaaag tagtaagatg atccttggctg ctcccccggc cctcttcccg   1200
ccctcttctt tgttgtcccc tgattatgct tgtttagcgc tggggcagtc ctcaaggatt   1260
ccctaaataa agccaaactg atgaacagta atagcctgtg tttaaaaaaa aaaaaatcgg   1320
aacataagaa acctcaggct gtcttcgatt actgttctag agaaacttta tgtttacacg   1380
aataaggaaa tgagttttg ttgggggttg aggaggaagg aaagtcatgg tgttctgacg   1440
tggaaaactt cttaaaagg ctgcttagtc tttagtttga aaataaacca aaaggttta   1500
ggagtcgggg aaaggcccta ggaaaatcca gacagtggtc acgtttgtgg acgacgttta   1560
gagcttgcta tcctgggcac acaagaaccc ttggactgtt cggtgcaaag ttggcaaatc   1620
ctacacggcc tgtgccaggg tttactttct gcatcaattt cacaggcgtc cagcctggct   1680
gaggactttt tgcggttttt aactggaagg gaaataagtc ggcatcagca cttagggctg   1740
cttaactttt aaaaggtggt agaacgccca gccttacacg ctgctgctta aattctcggt   1800
gctcaccaag gctgggctcg tgtggcccaa tcctgcaatc cccgaggcgg tgtttcttaa   1860
agagtgggct tgattctggt taaacccatt aagaagtcgg accccgggct cgtttcttgt   1920
tctgtaatta tgggtaaagt ccaaggatct gcgttttgaa gaggtaccta agtagttcat   1980
cttccttccc cctacaactt tttatttttta attagttaaa aatagtttta catttttgat   2040
atctcacaca caggtttttt ctttttttaa gcatcccagg aagacaaatg gctcagacgc   2100
caaccctttt attttattc cttgtctttt tctaaatctt tcaaaccccc cacctagagc   2160
tctagagatg tgtccattat gctctaccca cctccgcccc cgcccccatg actttaaaat   2220
gcttttttatt ccactttta tattgctcag tcgatcctca tgcactgcgc agtctgcaaa   2280
cttgaaactc aaggcgatcc acttcaatct tttcccgagt caagaaaaaa aggaaaaaaa   2340
gtagaataaaa aagcactcaa ataaaatctc cgaaacaaaa cctgaattca ctgcctaagg   2400
tcagggcctt tcttttgtgt gtcgctttaa gcatcgcgc gtgggctggg ggcagaccgc   2460
gcgtacccgc cctctttctg gggcgtcggc ggagcgtggc caatcaacgg gcgcggctat   2520
ggcagcggaa gccggaagcg gcgagcgggg tcgttctggg cctaggggag gcgggccgag   2580
ggcgtctgag ctgaggcccg cgtcgatcct gggttggagg aggtggcggc cgctgaggct   2640
gcggcgtgaa gacggcgggc                                              2660
```

<210> SEQ ID NO 2

-continued

```
<211> LENGTH: 21
<212> TYPE: DNA
<213> ORGANISM: Homo sapiens

<400> SEQUENCE: 2
ctctctgtaa ggtggatttg t                                              21

<210> SEQ ID NO 3
<211> LENGTH: 23
<212> TYPE: DNA
<213> ORGANISM: Homo sapiens

<400> SEQUENCE: 3
cattctcttc tctgctagct gcc                                            23

<210> SEQ ID NO 4
<211> LENGTH: 33
<212> TYPE: DNA
<213> ORGANISM: Homo sapiens

<400> SEQUENCE: 4
cccaagctta acccaacaca aataaactaa tga                                 33

<210> SEQ ID NO 5
<211> LENGTH: 21
<212> TYPE: DNA
<213> ORGANISM: Homo sapiens

<400> SEQUENCE: 5
gcaacaagtc agcaaacatg g                                              21

<210> SEQ ID NO 6
<211> LENGTH: 22
<212> TYPE: DNA
<213> ORGANISM: Homo sapiens

<400> SEQUENCE: 6
ctgtcggctg gtggaggagg aa                                             22

<210> SEQ ID NO 7
<211> LENGTH: 32
<212> TYPE: DNA
<213> ORGANISM: Homo sapiens

<400> SEQUENCE: 7
cgagctcatg gtggggaggg agaaagaact gt                                  32

<210> SEQ ID NO 8
<211> LENGTH: 6
<212> TYPE: DNA
<213> ORGANISM: Homo sapiens

<400> SEQUENCE: 8 aataaa                                                                6

<210> SEQ ID NO 9
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: synthesized peptide

<400> SEQUENCE: 9
```

Val Gly Arg Glu Lys Glu Leu Ser Ile His Phe Val Pro Gly Ser Asn
1               5                   10                  15

Glu Leu Val

<210> SEQ ID NO 10
<211> LENGTH: 38
<212> TYPE: DNA
<213> ORGANISM: Homo sapiens
<220> FEATURE:
<221> NAME/KEY: misc_feature
<222> LOCATION: (1)..(38)
<223> OTHER INFORMATION: y = t or c; r = g or a; n = g or a or t or c;
      s = g or c; w = a o r t; m = a or c; h = a or c or t

<400> SEQUENCE: 10
gtnggnmgng araargaryt nwsnathcay ttygtncc                               38

<210> SEQ ID NO 11
<211> LENGTH: 14
<212> TYPE: DNA
<213> ORGANISM: Homo sapiens

<400> SEQUENCE: 11
gacggcgggc atgg                                                          14

<210> SEQ ID NO 12
<211> LENGTH: 12
<212> TYPE: PRT
<213> ORGANISM: Homo sapiens

<400> SEQUENCE: 12

Arg Val Leu Val Thr Gly Ala Thr Gly Leu Leu Gly
1               5                   10

<210> SEQ ID NO 13
<211> LENGTH: 6
<212> TYPE: PRT
<213> ORGANISM: Homo sapiens

<400> SEQUENCE: 13

Asp Tyr Val Phe Asp Gly
1               5

<210> SEQ ID NO 14
<211> LENGTH: 17
<212> TYPE: PRT
<213> ORGANISM: Homo sapiens

<400> SEQUENCE: 14

Leu Asp Pro Ser Ile Lys Gly Thr Phe His Trp Ser Gly Asn Glu Gln
1               5                   10                  15

Thr

<210> SEQ ID NO 15
<211> LENGTH: 35
<212> TYPE: DNA
<213> ORGANISM: Homo sapiens
<220> FEATURE:
<221> NAME/KEY: misc_feature
<222> LOCATION: (1)..(35)
<223> OTHER INFORMATION: y = t or c; r = g or a; n = g or a or t or c;
      s = g or c; w = a o r t;

<400> SEQUENCE: 15

-continued

```
gtytgytcrt tnccnswcca rtgraangtn ccytt                         35

<210> SEQ ID NO 16
<211> LENGTH: 1867
<212> TYPE: DNA
<213> ORGANISM: Homo sapiens
<220> FEATURE:
<221> NAME/KEY: CDS
<222> LOCATION: (61)..(1062)
<223> OTHER INFORMATION:

<400> SEQUENCE: 16
cgtcgatcct gggttggagg aggtggcggc cgctgaggct gcggcgtgaa gacggcgggc    60 atg gtg ggg cgg gag aaa gaa ctg tct ata cac ttt gtt ccc ggg agc    108
Met Val Gly Arg Glu Lys Glu Leu Ser Ile His Phe Val Pro Gly Ser
 1               5                  10                  15 tgt cgg ctg gtg gag gag gaa gtt aac atc cct aat agg agg gtt ctg    156
Cys Arg Leu Val Glu Glu Glu Val Asn Ile Pro Asn Arg Arg Val Leu
             20                  25                  30 gtt act ggt gcc act ggg ctt ctt ggc aga gct gta cac aaa gaa ttt    204
Val Thr Gly Ala Thr Gly Leu Leu Gly Arg Ala Val His Lys Glu Phe
         35                  40                  45 cag cag aat aat tgg cat gca gtt ggc tgt ggt ttc aga aga gca aga    252
Gln Gln Asn Asn Trp His Ala Val Gly Cys Gly Phe Arg Arg Ala Arg
     50                  55                  60 cca aaa ttt gaa cag gtt aat ctg ttg gat tct aat gca gtt cat cac    300
Pro Lys Phe Glu Gln Val Asn Leu Leu Asp Ser Asn Ala Val His His
 65                  70                  75                  80 atc att cat gat ttt cag ccc cat gtt ata gta cat tgt gca gca gag    348
Ile Ile His Asp Phe Gln Pro His Val Ile Val His Cys Ala Ala Glu
                 85                  90                  95 aga aga cca gat gtt gta gaa aat cag cca gat gct gcc tct caa ctt    396
Arg Arg Pro Asp Val Val Glu Asn Gln Pro Asp Ala Ala Ser Gln Leu
            100                 105                 110 aat gtg gat gct tct ggg aat tta gca aag gaa gca gct gct gtt gga    444
Asn Val Asp Ala Ser Gly Asn Leu Ala Lys Glu Ala Ala Ala Val Gly
        115                 120                 125 gca ttt ctc atc tac att agc tca gat tat gta ttt gat gga aca aat    492
Ala Phe Leu Ile Tyr Ile Ser Ser Asp Tyr Val Phe Asp Gly Thr Asn
    130                 135                 140 cca cct tac aga gag gaa gac ata cca gct ccc cta aat ttg tat ggc    540
Pro Pro Tyr Arg Glu Glu Asp Ile Pro Ala Pro Leu Asn Leu Tyr Gly
145                 150                 155                 160 aaa aca aaa tta gat gga gaa aag gct gtc ctg gag aac aat cta gga    588
Lys Thr Lys Leu Asp Gly Glu Lys Ala Val Leu Glu Asn Asn Leu Gly
                165                 170                 175 gct gct gtt ttg agg att cct att ctg tat ggg gaa gtt gaa aag ctc    636
Ala Ala Val Leu Arg Ile Pro Ile Leu Tyr Gly Glu Val Glu Lys Leu
            180                 185                 190 gaa gaa agt gct gtg act gtt atg ttt gat aaa gtg cag ttc agc aac    684
Glu Glu Ser Ala Val Thr Val Met Phe Asp Lys Val Gln Phe Ser Asn
        195                 200                 205 aag tca gca aac atg gat cac tgg cag cag agg ttc ccc aca cat gtc    732
Lys Ser Ala Asn Met Asp His Trp Gln Gln Arg Phe Pro Thr His Val
    210                 215                 220 aaa gat gtg gcc act gtg tgc cgg cag cta gca gag aag aga atg ctg    780
Lys Asp Val Ala Thr Val Cys Arg Gln Leu Ala Glu Lys Arg Met Leu
225                 230                 235                 240 gat cca tca att aag gga acc ttt cac tgg tct ggc aat gaa cag atg    828
Asp Pro Ser Ile Lys Gly Thr Phe His Trp Ser Gly Asn Glu Gln Met
                245                 250                 255
```

-continued

```
act aag tat gaa atg gca tgt gca att gca gat gcc ttc aac ctc ccc      876
Thr Lys Tyr Glu Met Ala Cys Ala Ile Ala Asp Ala Phe Asn Leu Pro
            260                 265                 270 agc agt cac tta aga cct att act gac agc cct gtc cta gga gca caa      924
Ser Ser His Leu Arg Pro Ile Thr Asp Ser Pro Val Leu Gly Ala Gln
        275                 280                 285 cgt ccg aga aat gct cag ctt gac tgc tcc aaa ttg gag acc ttg ggc      972
Arg Pro Arg Asn Ala Gln Leu Asp Cys Ser Lys Leu Glu Thr Leu Gly
    290                 295                 300 att ggc caa cga aca cca ttt cga att gga atc aaa gaa tca ctt tgg     1020
Ile Gly Gln Arg Thr Pro Phe Arg Ile Gly Ile Lys Glu Ser Leu Trp
305                 310                 315                 320 cct ttc ctc att gac aag aga tgg aga caa acg gtc ttt cat             1062
Pro Phe Leu Ile Asp Lys Arg Trp Arg Gln Thr Val Phe His
                325                 330 tagtctattt gtgttgggtt cttttttttt taaatgaaaa gtatagtatg tggcactttt    1122
taaagaacaa aggaaatagt tttgtatgag tactttaatt gtgactctta ggatctttca    1182
ggtaaatgat gctcttgcac tagtgaaatt gtctaaagaa actaaagggc agtcatgccc    1242
tgtttgcagt aattttcctt tttatcattt tgtttgtcct ggctaaactt ggagtttgag    1302
tatagtaaat tatgatcctt aaatatttga gagtcaggat gaagcagacc tgctgtagac    1362
ttttcagatg aaattgttca ttctcgtaac ctccatattt tcaggatttt tgaagctgtt    1422
gacctttca tgttgattat tttaaattgt gtgaaatagt ataaaaatca ttggtgtaca     1482
ttatttgctt tgcctgagct cagatcaaaa tgtttgaaga aggaactttt attttttgcaa   1542
gttacgtaca gttttatgc ttgagatatt tcaacatgtt atgtatattg gaacttctac     1602
agcttgatgc ctcctgcttt tatagcagtt tatggggagc acttgaaaga gcgtgtgtac    1662
atgtatttt tttctaggca aacattgaat gcaaacgtgt atttttttaa tataaatata    1722
taactgtcct tttcatccca tgttgccgct aagtgatatt tcatatgtgt ggttatactc    1782
ataataatgg gccttgtaag ccttttcacc attcatgaat aataaaat atgtactgct     1842
ggcatgtaaa aaaaaaaaa aaaaa                                           1867
```

<210> SEQ ID NO 17
<211> LENGTH: 334
<212> TYPE: PRT
<213> ORGANISM: Homo sapiens

<400> SEQUENCE: 17

```
Met Val Gly Arg Glu Lys Glu Leu Ser Ile His Phe Val Pro Gly Ser
1               5                   10                  15

Cys Arg Leu Val Glu Glu Val Asn Ile Pro Asn Arg Arg Val Leu
                20                  25                  30

Val Thr Gly Ala Thr Gly Leu Leu Gly Arg Ala Val His Lys Glu Phe
            35                  40                  45

Gln Gln Asn Asn Trp His Ala Val Gly Cys Gly Phe Arg Arg Ala Arg
        50                  55                  60

Pro Lys Phe Glu Gln Val Asn Leu Leu Asp Ser Asn Ala Val His His
65                  70                  75                  80

Ile Ile His Asp Phe Gln Pro His Val Ile Val His Cys Ala Ala Glu
                85                  90                  95

Arg Arg Pro Asp Val Val Glu Asn Gln Pro Asp Ala Ala Ser Gln Leu
            100                 105                 110

Asn Val Asp Ala Ser Gly Asn Leu Ala Lys Glu Ala Ala Ala Val Gly
```

```
                115                 120                 125
Ala Phe Leu Ile Tyr Ile Ser Ser Asp Tyr Val Phe Asp Gly Thr Asn
    130                 135                 140

Pro Pro Tyr Arg Glu Glu Asp Ile Pro Ala Pro Leu Asn Leu Tyr Gly
145                 150                 155                 160

Lys Thr Lys Leu Asp Gly Glu Lys Ala Val Leu Glu Asn Asn Leu Gly
                165                 170                 175

Ala Ala Val Leu Arg Ile Pro Ile Leu Tyr Gly Val Glu Lys Leu
            180                 185                 190

Glu Glu Ser Ala Val Thr Val Met Phe Asp Lys Val Gln Phe Ser Asn
        195                 200                 205

Lys Ser Ala Asn Met Asp His Trp Gln Gln Arg Phe Pro Thr His Val
    210                 215                 220

Lys Asp Val Ala Thr Val Cys Arg Gln Leu Ala Glu Lys Arg Met Leu
225                 230                 235                 240

Asp Pro Ser Ile Lys Gly Thr Phe His Trp Ser Gly Asn Glu Gln Met
                245                 250                 255

Thr Lys Tyr Glu Met Ala Cys Ala Ile Ala Asp Ala Phe Asn Leu Pro
            260                 265                 270

Ser Ser His Leu Arg Pro Ile Thr Asp Ser Pro Val Leu Gly Ala Gln
        275                 280                 285

Arg Pro Arg Asn Ala Gln Leu Asp Cys Ser Lys Leu Glu Thr Leu Gly
    290                 295                 300

Ile Gly Gln Arg Thr Pro Phe Arg Ile Gly Ile Lys Glu Ser Leu Trp
305                 310                 315                 320

Pro Phe Leu Ile Asp Lys Arg Trp Arg Gln Thr Val Phe His
                325                 330

<210> SEQ ID NO 18
<211> LENGTH: 1867
<212> TYPE: DNA
<213> ORGANISM: Homo sapiens
<220> FEATURE:
<221> NAME/KEY: CDS
<222> LOCATION: (61)..(1062)
<223> OTHER INFORMATION:

<400> SEQUENCE: 18
cgtcgatcct gggttggagg aggtggcggc cgctgaggct gcggcgtgaa gacggcgggc      60 atg gtg ggg cgg gag aaa gaa atc tct ata cac ttt gtt ccc ggg agc     108
Met Val Gly Arg Glu Lys Glu Ile Ser Ile His Phe Val Pro Gly Ser
1               5                   10                  15 tgt cgg ctg gtg gag gag gaa gtt aac atc cct aat agg agg gtt ctg     156
Cys Arg Leu Val Glu Glu Glu Val Asn Ile Pro Asn Arg Arg Val Leu
            20                  25                  30 gtt act ggt gcc act ggg ctt ctt ggc aga gct gta cac aaa gaa ttt     204
Val Thr Gly Ala Thr Gly Leu Leu Gly Arg Ala Val His Lys Glu Phe
        35                  40                  45 cag cag aat aat tgg cat gca gtt ggc tgt ggt ttc aga aga gca aga     252
Gln Gln Asn Asn Trp His Ala Val Gly Cys Gly Phe Arg Arg Ala Arg
    50                  55                  60 cca aaa ttt gaa cag gtt aat ctg ttg gat tct aat gca gtt cat cac     300
Pro Lys Phe Glu Gln Val Asn Leu Leu Asp Ser Asn Ala Val His His
65                  70                  75                  80 atc att cat gat ttt cag ccc cat gtt ata gta cat tgt gca gca gag     348
Ile Ile His Asp Phe Gln Pro His Val Ile Val His Cys Ala Ala Glu
                85                  90                  95
```

-continued

| | | |
|---|---|---|
| aga aga cca gat gtt gta gaa aat cag cca gat gct gcc tct caa ctt<br>Arg Arg Pro Asp Val Val Glu Asn Gln Pro Asp Ala Ala Ser Gln Leu<br>100 105 110 | 396 |
| aat gtg gat gct tct ggg aat tta gca aag gaa gca gct gct gtt gga<br>Asn Val Asp Ala Ser Gly Asn Leu Ala Lys Glu Ala Ala Ala Val Gly<br>115 120 125 | 444 |
| gca ttt ctc atc tac att agc tca gat tat gta ttt gat gga aca aat<br>Ala Phe Leu Ile Tyr Ile Ser Ser Asp Tyr Val Phe Asp Gly Thr Asn<br>130 135 140 | 492 |
| cca cct tac aga gag gaa gac ata cca gct ccc cta aat ttg tat ggc<br>Pro Pro Tyr Arg Glu Glu Asp Ile Pro Ala Pro Leu Asn Leu Tyr Gly<br>145 150 155 160 | 540 |
| aaa aca aaa tta gat gga gaa aag gct gtc ctg gag aac aat cta gga<br>Lys Thr Lys Leu Asp Gly Glu Lys Ala Val Leu Glu Asn Asn Leu Gly<br>165 170 175 | 588 |
| gct gct gtt ttg agg att cct att ctg tat ggg gaa gtt gaa aag ctc<br>Ala Ala Val Leu Arg Ile Pro Ile Leu Tyr Gly Glu Val Glu Lys Leu<br>180 185 190 | 636 |
| gaa gaa agt gct gtg act gtt atg ttt gat aaa gtg cag ttc agc aac<br>Glu Glu Ser Ala Val Thr Val Met Phe Asp Lys Val Gln Phe Ser Asn<br>195 200 205 | 684 |
| aag tca gca aac atg gat cac tgg cag cag agg ttc ccc aca cat gtc<br>Lys Ser Ala Asn Met Asp His Trp Gln Gln Arg Phe Pro Thr His Val<br>210 215 220 | 732 |
| aaa gat gtg gcc act gtg tgc cgg cag cta gca gag aag aga atg ctg<br>Lys Asp Val Ala Thr Val Cys Arg Gln Leu Ala Glu Lys Arg Met Leu<br>225 230 235 240 | 780 |
| gat cca tca att aag gga acc ttt cac tgg tct ggc aat gaa cag atg<br>Asp Pro Ser Ile Lys Gly Thr Phe His Trp Ser Gly Asn Glu Gln Met<br>245 250 255 | 828 |
| act aag tat gaa atg gca tgt gca att gca gat gcc ttc aac ctc ccc<br>Thr Lys Tyr Glu Met Ala Cys Ala Ile Ala Asp Ala Phe Asn Leu Pro<br>260 265 270 | 876 |
| agc agt cac tta aga cct att act gac agc cct gtc cta gga gca caa<br>Ser Ser His Leu Arg Pro Ile Thr Asp Ser Pro Val Leu Gly Ala Gln<br>275 280 285 | 924 |
| cgt ccg aga aat gct cag ctt gac tgc tcc aaa ttg gag acc ttg ggc<br>Arg Pro Arg Asn Ala Gln Leu Asp Cys Ser Lys Leu Glu Thr Leu Gly<br>290 295 300 | 972 |
| att ggc caa cga aca cca ttt cga att gga atc aaa gaa tca ctt tgg<br>Ile Gly Gln Arg Thr Pro Phe Arg Ile Gly Ile Lys Glu Ser Leu Trp<br>305 310 315 320 | 1020 |
| cct ttc ctc att gac aag aga tgg aga caa acg gtc ttt cat<br>Pro Phe Leu Ile Asp Lys Arg Trp Arg Gln Thr Val Phe His<br>325 330 | 1062 |
| tagtctattt gtgttgggtt cttttttttt taaatgaaaa gtatagtatg tggcactttt | 1122 |
| taaagaacaa aggaaatagt tttgtatgag tactttaatt gtgactctta ggatctttca | 1182 |
| ggtaaatgat gctcttgcac tagtgaaatt gtctaaagaa actaaagggc agtcatgccc | 1242 |
| tgtttgcagt aattttctt tttatcattt tgtttgtcct ggctaaactt ggagtttgag | 1302 |
| tatagtaaat tatgatcctt aaatatttga gagtcaggat gaagcagacc tgctgtagac | 1362 |
| ttttcagatg aaattgttca ttctcgtaac ctccatattt tcaggatttt tgaagctgtt | 1422 |
| gacctttca tgttgattat tttaaattgt gtgaaatagt ataaaaatca ttggtgtaca | 1482 |
| ttatttgctt tgcctgagct cagatcaaaa tgtttgaaga aggaactttt attttttgcaa | 1542 |
| gttacgtaca gttttttatgc ttgagatatt tcaacatgtt atgtatattg gaacttctac | 1602 |
| agcttgatgc ctcctgcttt tatagcagtt tatggggagc acttgaaaga gcgtgtgtac | 1662 |

-continued

```
atgtattttt tttctaggca aacattgaat gcaaacgtgt atttttttaa tataaatata      1722
taactgtcct tttcatccca tgttgccgct aagtgatatt tcatatgtgt ggttatactc      1782
ataataatgg gccttgtaag cctttcacc attcatgaat aataataaat atgtactgct       1842
ggcatgtaaa aaaaaaaaaa aaaaa                                            1867
```

<210> SEQ ID NO 19
<211> LENGTH: 334
<212> TYPE: PRT
<213> ORGANISM: Homo sapiens

<400> SEQUENCE: 19

```
Met Val Gly Arg Glu Lys Glu Ile Ser Ile His Phe Val Pro Gly Ser
1               5                   10                  15

Cys Arg Leu Val Glu Glu Val Asn Ile Pro Asn Arg Arg Val Leu
                20                  25                  30

Val Thr Gly Ala Thr Gly Leu Leu Gly Arg Ala Val His Lys Glu Phe
            35                  40                  45

Gln Gln Asn Asn Trp His Ala Val Gly Cys Gly Phe Arg Arg Ala Arg
        50                  55                  60

Pro Lys Phe Glu Gln Val Asn Leu Leu Asp Ser Asn Ala Val His His
65                  70                  75                  80

Ile Ile His Asp Phe Gln Pro His Val Ile Val His Cys Ala Ala Glu
                85                  90                  95

Arg Arg Pro Asp Val Val Glu Asn Gln Pro Asp Ala Ala Ser Gln Leu
                100                 105                 110

Asn Val Asp Ala Ser Gly Asn Leu Ala Lys Glu Ala Ala Ala Val Gly
            115                 120                 125

Ala Phe Leu Ile Tyr Ile Ser Ser Asp Tyr Val Phe Asp Gly Thr Asn
        130                 135                 140

Pro Pro Tyr Arg Glu Glu Asp Ile Pro Ala Pro Leu Asn Leu Tyr Gly
145                 150                 155                 160

Lys Thr Lys Leu Asp Gly Glu Lys Ala Val Leu Glu Asn Asn Leu Gly
                165                 170                 175

Ala Ala Val Leu Arg Ile Pro Ile Leu Tyr Gly Glu Val Glu Lys Leu
            180                 185                 190

Glu Glu Ser Ala Val Thr Val Met Phe Asp Lys Val Gln Phe Ser Asn
        195                 200                 205

Lys Ser Ala Asn Met Asp His Trp Gln Gln Arg Phe Pro Thr His Val
    210                 215                 220

Lys Asp Val Ala Thr Val Cys Arg Gln Leu Ala Glu Lys Arg Met Leu
225                 230                 235                 240

Asp Pro Ser Ile Lys Gly Thr Phe His Trp Ser Gly Asn Glu Gln Met
                245                 250                 255

Thr Lys Tyr Glu Met Ala Cys Ala Ile Ala Asp Ala Phe Asn Leu Pro
            260                 265                 270

Ser Ser His Leu Arg Pro Ile Thr Asp Ser Pro Val Leu Gly Ala Gln
        275                 280                 285

Arg Pro Arg Asn Ala Gln Leu Asp Cys Ser Lys Leu Glu Thr Leu Gly
    290                 295                 300

Ile Gly Gln Arg Thr Pro Phe Arg Ile Gly Ile Lys Glu Ser Leu Trp
305                 310                 315                 320

Pro Phe Leu Ile Asp Lys Arg Trp Arg Gln Thr Val Phe His
                325                 330
```

<210> SEQ ID NO 20
<211> LENGTH: 1867
<212> TYPE: DNA
<213> ORGANISM: Homo sapiens
<220> FEATURE:
<221> NAME/KEY: CDS
<222> LOCATION: (61)..(1062)
<223> OTHER INFORMATION:

<400> SEQUENCE: 20

| | | |
|---|---|---|
| cgtcgatcct gggttggagg aggtggcggc cgctgaggct gcggcgtgaa gacggcgggc | | 60 |
| atg gtg ggg cgg gag aaa gaa ctg tct ata cac ttt gtt ccc ggg agc<br>Met Val Gly Arg Glu Lys Glu Leu Ser Ile His Phe Val Pro Gly Ser<br>1                      5                   10                 15 | | 108 |
| tgt cgg ctg gtg gag gag gaa gtt aac atc cct aat agg agg gtt atc<br>Cys Arg Leu Val Glu Glu Glu Val Asn Ile Pro Asn Arg Arg Val Ile<br>             20                   25                   30 | | 156 |
| gtt act ggt gcc act ggg ctt ctt ggc aga gct gta cac aaa gaa ttt<br>Val Thr Gly Ala Thr Gly Leu Leu Gly Arg Ala Val His Lys Glu Phe<br>                 35                 40                  45 | | 204 |
| cag cag aat aat tgg cat gca gtt ggc tgt ggt ttc aga aga gca aga<br>Gln Gln Asn Asn Trp His Ala Val Gly Cys Gly Phe Arg Arg Ala Arg<br> 50                     55                   60 | | 252 |
| cca aaa ttt gaa cag gtt aat ctg ttg gat tct aat gca gtt cat cac<br>Pro Lys Phe Glu Gln Val Asn Leu Leu Asp Ser Asn Ala Val His His<br>65                    70                   75                  80 | | 300 |
| atc att cat gat ttt cag ccc cat gtt ata gta cat tgt gca gca gag<br>Ile Ile His Asp Phe Gln Pro His Val Ile Val His Cys Ala Ala Glu<br>                       85                 90                  95 | | 348 |
| aga aga cca gat gtt gta gaa aat cag cca gat gct gcc tct caa ctt<br>Arg Arg Pro Asp Val Val Glu Asn Gln Pro Asp Ala Ala Ser Gln Leu<br>            100                  105               110 | | 396 |
| aat gtg gat gct tct ggg aat tta gca aag gaa gca gct gct gtt gga<br>Asn Val Asp Ala Ser Gly Asn Leu Ala Lys Glu Ala Ala Ala Val Gly<br>        115                  120               125 | | 444 |
| gca ttt ctc atc tac att agc tca gat tat gta ttt gat gga aca aat<br>Ala Phe Leu Ile Tyr Ile Ser Ser Asp Tyr Val Phe Asp Gly Thr Asn<br>130                   135                  140 | | 492 |
| cca cct tac aga gag gaa gac ata cca gct ccc cta aat ttg tat ggc<br>Pro Pro Tyr Arg Glu Glu Asp Ile Pro Ala Pro Leu Asn Leu Tyr Gly<br>145                   150                  155               160 | | 540 |
| aaa aca aaa tta gat gga gaa aag gct gtc ctg gag aac aat cta gga<br>Lys Thr Lys Leu Asp Gly Glu Lys Ala Val Leu Glu Asn Asn Leu Gly<br>                 165                  170               175 | | 588 |
| gct gct gtt ttg agg att cct att ctg tat ggg gaa gtt gaa aag ctc<br>Ala Ala Val Leu Arg Ile Pro Ile Leu Tyr Gly Glu Val Glu Lys Leu<br>            180                  185               190 | | 636 |
| gaa gaa agt gct gtg act gtt atg ttt gat aaa gtg cag ttc agc aac<br>Glu Glu Ser Ala Val Thr Val Met Phe Asp Lys Val Gln Phe Ser Asn<br>        195                  200               205 | | 684 |
| aag tca gca aac atg gat cac tgg cag cag agg ttc ccc aca cat gtc<br>Lys Ser Ala Asn Met Asp His Trp Gln Gln Arg Phe Pro Thr His Val<br>210                   215                  220 | | 732 |
| aaa gat gtg gcc act gtg tgc cgg cag cta gca gag aag aga atg ctg<br>Lys Asp Val Ala Thr Val Cys Arg Gln Leu Ala Glu Lys Arg Met Leu<br>225                   230                  235               240 | | 780 |
| gat cca tca att aag gga acc ttt cac tgg tct ggc aat gaa cag atg<br>Asp Pro Ser Ile Lys Gly Thr Phe His Trp Ser Gly Asn Glu Gln Met<br>                 245                  250               255 | | 828 |

```
act aag tat gaa atg gca tgt gca att gca gat gcc ttc aac ctc ccc      876
Thr Lys Tyr Glu Met Ala Cys Ala Ile Ala Asp Ala Phe Asn Leu Pro
        260                 265                 270 agc agt cac tta aga cct att act gac agc cct gtc cta gga gca caa      924
Ser Ser His Leu Arg Pro Ile Thr Asp Ser Pro Val Leu Gly Ala Gln
            275                 280                 285 cgt ccg aga aat gct cag ctt gac tgc tcc aaa ttg gag acc ttg ggc      972
Arg Pro Arg Asn Ala Gln Leu Asp Cys Ser Lys Leu Glu Thr Leu Gly
290                 295                 300 att ggc caa cga aca cca ttt cga att gga atc aaa gaa tca ctt tgg     1020
Ile Gly Gln Arg Thr Pro Phe Arg Ile Gly Ile Lys Glu Ser Leu Trp
305                 310                 315                 320 cct ttc ctc att gac aag aga tgg aga caa acg gtc ttt cat             1062
Pro Phe Leu Ile Asp Lys Arg Trp Arg Gln Thr Val Phe His
                325                 330 tagtctattt gtgttgggtt ctttttttt taaatgaaaa gtatagtatg tggcactttt    1122
taaagaacaa aggaaatagt tttgtatgag tactttaatt gtgactctta ggatctttca   1182
ggtaaatgat gctcttgcac tagtgaaatt gtctaaagaa actaaagggc agtcatgccc   1242
tgtttgcagt aattttctt tttatcattt tgtttgtcct ggctaaactt ggagtttgag    1302
tatagtaaat tatgatcctt aaatatttga gagtcaggat gaagcagacc tgctgtagac   1362
ttttcagatg aaattgttca ttctcgtaac ctccatattt tcaggatttt tgaagctgtt   1422
gaccttttca tgttgattat tttaaattgt gtgaaatagt ataaaaatca ttggtgtaca   1482
ttatttgctt tgcctgagct cagatcaaaa tgtttgaaga aaggaacttt attttttgcaa  1542 gttacgtaca gttttttatgc ttgagatatt tcaacatgtt atgtatattg gaacttctac  1602
agcttgatgc ctcctgctt tatagcagtt tatggggagc acttgaaaga gcgtgtgtac    1662 atgtatttt tttctaggca aacattgaat gcaaacgtgt attttttaa tataaatata     1722 taactgtcct tttcatccca tgttgccgct aagtgatatt tcatatgtgt ggttatactc   1782
ataataatgg gccttgtaag cctttcacc attcatgaat aataataaat atgtactgct    1842
ggcatgtaaa aaaaaaaaaa aaaaa                                         1867

<210> SEQ ID NO 21
<211> LENGTH: 334
<212> TYPE: PRT
<213> ORGANISM: Homo sapiens

<400> SEQUENCE: 21

Met Val Gly Arg Glu Lys Glu Leu Ser Ile His Phe Val Pro Gly Ser
1               5                   10                  15

Cys Arg Leu Val Glu Glu Val Asn Ile Pro Asn Arg Arg Val Ile
                20                  25                  30

Val Thr Gly Ala Thr Gly Leu Leu Gly Arg Ala Val His Lys Glu Phe
            35                  40                  45

Gln Gln Asn Asn Trp His Ala Val Gly Cys Gly Phe Arg Arg Ala Arg
        50                  55                  60

Pro Lys Phe Glu Gln Val Asn Leu Leu Asp Ser Asn Ala Val His His
65                  70                  75                  80

Ile Ile His Asp Phe Gln Pro Val Ile Val His Cys Ala Ala Glu
                85                  90                  95

Arg Arg Pro Asp Val Val Glu Asn Gln Pro Asp Ala Ala Ser Gln Leu
                100                 105                 110

Asn Val Asp Ala Ser Gly Asn Leu Ala Lys Glu Ala Ala Val Gly
            115                 120                 125
```

```
Ala Phe Leu Ile Tyr Ile Ser Ser Asp Tyr Val Phe Asp Gly Thr Asn
        130                 135                 140

Pro Pro Tyr Arg Glu Glu Asp Ile Pro Ala Pro Leu Asn Leu Tyr Gly
145                 150                 155                 160

Lys Thr Lys Leu Asp Gly Glu Lys Ala Val Leu Glu Asn Asn Leu Gly
                165                 170                 175

Ala Ala Val Leu Arg Ile Pro Ile Leu Tyr Gly Val Glu Lys Leu
            180                 185                 190

Glu Glu Ser Ala Val Thr Val Met Phe Asp Lys Val Gln Phe Ser Asn
            195                 200                 205

Lys Ser Ala Asn Met Asp His Trp Gln Gln Arg Phe Pro Thr His Val
    210                 215                 220

Lys Asp Val Ala Thr Val Cys Arg Gln Leu Ala Glu Lys Arg Met Leu
225                 230                 235                 240

Asp Pro Ser Ile Lys Gly Thr Phe His Trp Ser Gly Asn Glu Gln Met
                245                 250                 255

Thr Lys Tyr Glu Met Ala Cys Ala Ile Ala Asp Ala Phe Asn Leu Pro
            260                 265                 270

Ser Ser His Leu Arg Pro Ile Thr Asp Ser Pro Val Leu Gly Ala Gln
        275                 280                 285

Arg Pro Arg Asn Ala Gln Leu Asp Cys Ser Lys Leu Glu Thr Leu Gly
290                 295                 300

Ile Gly Gln Arg Thr Pro Phe Arg Ile Gly Ile Lys Glu Ser Leu Trp
305                 310                 315                 320

Pro Phe Leu Ile Asp Lys Arg Trp Arg Gln Thr Val Phe His
                325                 330

<210> SEQ ID NO 22
<211> LENGTH: 1867
<212> TYPE: DNA
<213> ORGANISM: Homo sapiens
<220> FEATURE:
<221> NAME/KEY: CDS
<222> LOCATION: (61)..(1062)
<223> OTHER INFORMATION:

<400> SEQUENCE: 22
cgtcgatcct gggttggagg aggtggcggc cgctgaggct gcggcgtgaa gacggcgggc      60 atg gtg ggg cgg gag aaa gaa ctg tct ata cac ttt gtt ccc ggg agc      108
Met Val Gly Arg Glu Lys Glu Leu Ser Ile His Phe Val Pro Gly Ser
1               5                   10                  15 tgt cgg ctg gtg gag gag gaa gtt aac atc cct aat agg agg gtt ctg      156
Cys Arg Leu Val Glu Glu Glu Val Asn Ile Pro Asn Arg Arg Val Leu
                20                  25                  30 gtt act ggt gcc act ggg ctt ctt ggc aga gct gta cac aaa gaa ttt      204
Val Thr Gly Ala Thr Gly Leu Leu Gly Arg Ala Val His Lys Glu Phe
            35                  40                  45 cag cag aat aat tgg cat gca gtt ggc tgt ggt ttc aga aga gca aga      252
Gln Gln Asn Asn Trp His Ala Val Gly Cys Gly Phe Arg Arg Ala Arg
        50                  55                  60 cca aaa ttt gaa cag gtt aat ctg ttg gat tct aat gca gtt cat cac      300
Pro Lys Phe Glu Gln Val Asn Leu Leu Asp Ser Asn Ala Val His His
65                  70                  75                  80 atc att cat gat ttt cag ccc cat gtt ata gta cat tgt gca gca gag      348
Ile Ile His Asp Phe Gln Pro His Val Ile Val His Cys Ala Ala Glu
                85                  90                  95 aga aga cca gat gtt gta gaa aat cag cca gat gct gcc tct caa ctt      396
```

```
Arg Arg Pro Asp Val Val Glu Asn Gln Pro Asp Ala Ala Ser Gln Leu
            100                 105                 110 aat gtg gat gct tct ggg aat tta gca aag gaa gca gct gtt gga        444
Asn Val Asp Ala Ser Gly Asn Leu Ala Lys Glu Ala Ala Val Gly
        115                 120                 125 gca ttt ctc atc tac att agc tca gat tat gta ttt gat gga aca aat    492
Ala Phe Leu Ile Tyr Ile Ser Ser Asp Tyr Val Phe Asp Gly Thr Asn
130                 135                 140 cca cct tac aga gag gaa gac ata cca gct ccc cta aat ttg tat ggc    540
Pro Pro Tyr Arg Glu Glu Asp Ile Pro Ala Pro Leu Asn Leu Tyr Gly
145                 150                 155                 160 aaa aca aaa tta gat gga gaa aag gct gtc ctg gag aac aat atc gga    588
Lys Thr Lys Leu Asp Gly Glu Lys Ala Val Leu Glu Asn Asn Ile Gly
                165                 170                 175 gct gct gtt ttg agg att cct att ctg tat ggg gaa gtt gaa aag ctc    636
Ala Ala Val Leu Arg Ile Pro Ile Leu Tyr Gly Glu Val Glu Lys Leu
            180                 185                 190 gaa gaa agt gct gtg act gtt atg ttt gat aaa gtg cag ttc agc aac    684
Glu Glu Ser Ala Val Thr Val Met Phe Asp Lys Val Gln Phe Ser Asn
        195                 200                 205 aag tca gca aac atg gat cac tgg cag cag agg ttc ccc aca cat gtc    732
Lys Ser Ala Asn Met Asp His Trp Gln Gln Arg Phe Pro Thr His Val
210                 215                 220 aaa gat gtg gcc act gtg tgc cgg cag cta gca gag aag aga atg ctg    780
Lys Asp Val Ala Thr Val Cys Arg Gln Leu Ala Glu Lys Arg Met Leu
225                 230                 235                 240 gat cca tca att aag gga acc ttt cac tgg tct ggc aat gaa cag atg    828
Asp Pro Ser Ile Lys Gly Thr Phe His Trp Ser Gly Asn Glu Gln Met
                245                 250                 255 act aag tat gaa atg gca tgt gca att gca gat gcc ttc aac ctc ccc    876
Thr Lys Tyr Glu Met Ala Cys Ala Ile Ala Asp Ala Phe Asn Leu Pro
            260                 265                 270 agc agt cac tta aga cct att act gac agc cct gtc cta gga gca caa    924
Ser Ser His Leu Arg Pro Ile Thr Asp Ser Pro Val Leu Gly Ala Gln
        275                 280                 285 cgt ccg aga aat gct cag ctt gac tgc tcc aaa ttg gag acc ttg ggc    972
Arg Pro Arg Asn Ala Gln Leu Asp Cys Ser Lys Leu Glu Thr Leu Gly
290                 295                 300 att ggc caa cga aca cca ttt cga att gga atc aaa gaa tca ctt tgg    1020
Ile Gly Gln Arg Thr Pro Phe Arg Ile Gly Ile Lys Glu Ser Leu Trp
305                 310                 315                 320 cct ttc ctc att gac aag aga tgg aga caa acg gtc ttt cat             1062
Pro Phe Leu Ile Asp Lys Arg Trp Arg Gln Thr Val Phe His
                325                 330 tagtctattt gtgttgggtt cttttttttt taaatgaaaa gtatagtatg tggcactttt    1122
taaagaacaa aggaaatagt tttgtatgag tactttaatt gtgactctta ggatctttca    1182
ggtaaatgat gctcttgcac tagtgaaatt gtctaaagaa actaaagggc agtcatgccc    1242
tgtttgcagt aattttctt tttatcattt tgtttgtcct ggctaaactt ggagtttgag     1302
tatagtaaat tatgatcctt aaatatttga gagtcaggat gaagcagacc tgctgtagac    1362
ttttcagatg aaattgttca ttctcgtaac ctccatattt tcaggatttt tgaagctgtt    1422
gaccttttca tgttgattat tttaaattgt gtgaaatagt ataaaaatca ttggtgtaca    1482
ttatttgctt tgcctgagct cagatcaaaa tgtttgaaga aggaactttt attttttgcaa   1542 gttacgtaca gttttttatgc ttgagatatt tcaacatgtt atgtatattg gaacttctac   1602
agcttgatgc ctcctgcttt tatagcagtt tatggggagc acttgaaaga gcgtgtgtac    1662
```

```
atgtattttt tttctaggca aacattgaat gcaaacgtgt atttttttaa tataaatata   1722
taactgtcct tttcatccca tgttgccgct aagtgatatt tcatatgtgt ggttatactc   1782
ataataatgg gccttgtaag cctttcacc attcatgaat aataataaat atgtactgct   1842
ggcatgtaaa aaaaaaaaaa aaaaa                                          1867

<210> SEQ ID NO 23
<211> LENGTH: 334
<212> TYPE: PRT
<213> ORGANISM: Homo sapiens

<400> SEQUENCE: 23

Met Val Gly Arg Glu Lys Glu Leu Ser Ile His Phe Val Pro Gly Ser
1               5                   10                  15

Cys Arg Leu Val Glu Glu Val Asn Ile Pro Asn Arg Arg Val Leu
            20                  25                  30

Val Thr Gly Ala Thr Gly Leu Leu Gly Arg Ala Val His Lys Glu Phe
        35                  40                  45

Gln Gln Asn Asn Trp His Ala Val Gly Cys Gly Phe Arg Arg Ala Arg
    50                  55                  60

Pro Lys Phe Glu Gln Val Asn Leu Leu Asp Ser Asn Ala Val His His
65                  70                  75                  80

Ile Ile His Asp Phe Gln Pro His Val Ile Val His Cys Ala Ala Glu
                85                  90                  95

Arg Arg Pro Asp Val Val Glu Asn Gln Pro Asp Ala Ala Ser Gln Leu
            100                 105                 110

Asn Val Asp Ala Ser Gly Asn Leu Ala Lys Glu Ala Ala Ala Val Gly
        115                 120                 125

Ala Phe Leu Ile Tyr Ile Ser Ser Asp Tyr Val Phe Asp Gly Thr Asn
    130                 135                 140

Pro Pro Tyr Arg Glu Glu Asp Ile Pro Ala Pro Leu Asn Leu Tyr Gly
145                 150                 155                 160

Lys Thr Lys Leu Asp Gly Glu Lys Ala Val Leu Glu Asn Asn Ile Gly
                165                 170                 175

Ala Ala Val Leu Arg Ile Pro Ile Leu Tyr Gly Glu Val Glu Lys Leu
            180                 185                 190

Glu Glu Ser Ala Val Thr Val Met Phe Asp Lys Val Gln Phe Ser Asn
        195                 200                 205

Lys Ser Ala Asn Met Asp His Trp Gln Gln Arg Phe Pro Thr His Val
    210                 215                 220

Lys Asp Val Ala Thr Val Cys Arg Gln Leu Ala Glu Lys Arg Met Leu
225                 230                 235                 240

Asp Pro Ser Ile Lys Gly Thr Phe His Trp Ser Gly Asn Glu Gln Met
                245                 250                 255

Thr Lys Tyr Glu Met Ala Cys Ala Ile Ala Asp Ala Phe Asn Leu Pro
            260                 265                 270

Ser Ser His Leu Arg Pro Ile Thr Asp Ser Pro Val Leu Gly Ala Gln
        275                 280                 285

Arg Pro Arg Asn Ala Gln Leu Asp Cys Ser Lys Leu Glu Thr Leu Gly
    290                 295                 300

Ile Gly Gln Arg Thr Pro Phe Arg Ile Gly Ile Lys Glu Ser Leu Trp
305                 310                 315                 320

Pro Phe Leu Ile Asp Lys Arg Trp Arg Gln Thr Val Phe His
                325                 330
```

-continued

```
<210> SEQ ID NO 24
<211> LENGTH: 1850
<212> TYPE: DNA
<213> ORGANISM: Homo sapiens
<220> FEATURE:
<221> NAME/KEY: CDS
<222> LOCATION: (61)..(1062)
<223> OTHER INFORMATION:

<400> SEQUENCE: 24
cgtcgatcct gggttggagg aggtggcggc cgctgaggct gcggcgtgaa gacggcgggc       60 atg gtg ggg cgg gag aaa gaa ctg tct ata cac ttt gtt ccc ggg agc      108
Met Val Gly Arg Glu Lys Glu Leu Ser Ile His Phe Val Pro Gly Ser
1               5                   10                  15 tgt cgg ctg gtg gag gag gaa gtt aac atc cct aat agg agg gtt ctg      156
Cys Arg Leu Val Glu Glu Glu Val Asn Ile Pro Asn Arg Arg Val Leu
            20                  25                  30 gtt act ggt gcc act ggg ctt ctt ggc aga gct gta cac aaa gaa ttt      204
Val Thr Gly Ala Thr Gly Leu Leu Gly Arg Ala Val His Lys Glu Phe
        35                  40                  45 cag cag aat aat tgg cat gca gtt ggc tgt ggt ttc aga aga gca aga      252
Gln Gln Asn Asn Trp His Ala Val Gly Cys Gly Phe Arg Arg Ala Arg
    50                  55                  60 cca aaa ttt gaa cag gtt aat ctg ttg gat tct aat gca gtt cat cac      300
Pro Lys Phe Glu Gln Val Asn Leu Leu Asp Ser Asn Ala Val His His
65              70                  75                  80 atc att cat gat ttt cag ccc cat gtt ata gta cat tgt gca gca gag      348
Ile Ile His Asp Phe Gln Pro His Val Ile Val His Cys Ala Ala Glu
                85                  90                  95 aga aga cca gat gtt gta gaa aat cag cca gat gct gcc tct caa ctt      396
Arg Arg Pro Asp Val Val Glu Asn Gln Pro Asp Ala Ala Ser Gln Leu
            100                 105                 110 aat gtg gat gct tct ggg aat tta gca aag gaa gca gct gct gtt gga      444
Asn Val Asp Ala Ser Gly Asn Leu Ala Lys Glu Ala Ala Ala Val Gly
        115                 120                 125 gca ttt ctc atc tac att agc tca gat tat gta ttt gat gga aca aat      492
Ala Phe Leu Ile Tyr Ile Ser Ser Asp Tyr Val Phe Asp Gly Thr Asn
    130                 135                 140 cca cct tac aga gag gaa gac ata cca gct ccc cta aat ttg tat ggc      540
Pro Pro Tyr Arg Glu Glu Asp Ile Pro Ala Pro Leu Asn Leu Tyr Gly
145             150                 155                 160 aaa aca aaa tta gat gga gaa aag gct gtc ctg gag aac aat cta gga      588
Lys Thr Lys Leu Asp Gly Glu Lys Ala Val Leu Glu Asn Asn Leu Gly
                165                 170                 175 gct gct gtt ttg agg att cct att ctg tat ggg gaa gtt gaa aag ctc      636
Ala Ala Val Leu Arg Ile Pro Ile Leu Tyr Gly Glu Val Glu Lys Leu
            180                 185                 190 gaa gaa agt gct gtg act gtt atg ttt gat aaa gtg cag ttc agc aac      684
Glu Glu Ser Ala Val Thr Val Met Phe Asp Lys Val Gln Phe Ser Asn
        195                 200                 205 aag tca gca aac atg gat cac tgg cag cag agg ttc ccc aca cat gtc      732
Lys Ser Ala Asn Met Asp His Trp Gln Gln Arg Phe Pro Thr His Val
    210                 215                 220 aaa gat gtg gcc act gtg tgc cgg cag cta gca gag aag aga atg ctg      780
Lys Asp Val Ala Thr Val Cys Arg Gln Leu Ala Glu Lys Arg Met Leu
225             230                 235                 240 gat cca tca att aag gga acc ttt cac tgg tct ggc aat gaa cag atg      828
Asp Pro Ser Ile Lys Gly Thr Phe His Trp Ser Gly Asn Glu Gln Met
                245                 250                 255 act aag tat gaa atg gca tgt gca att gca gat gcc ttc aac atc ccc      876
Thr Lys Tyr Glu Met Ala Cys Ala Ile Ala Asp Ala Phe Asn Ile Pro
```

-continued

```
Thr Lys Tyr Glu Met Ala Cys Ala Ile Ala Asp Ala Phe Asn Ile Pro
            260                 265                 270 agc agt cac tta aga cct att act gac agc cct gtc cta gga gca caa         924
Ser Ser His Leu Arg Pro Ile Thr Asp Ser Pro Val Leu Gly Ala Gln
            275                 280                 285 cgt ccg aga aat gct cag ctt gac tgc tcc aaa ttg gag acc ttg ggc         972
Arg Pro Arg Asn Ala Gln Leu Asp Cys Ser Lys Leu Glu Thr Leu Gly
        290                 295                 300 att ggc caa cga aca cca ttt cga att gga atc aaa gaa tca ctt tgg        1020
Ile Gly Gln Arg Thr Pro Phe Arg Ile Gly Ile Lys Glu Ser Leu Trp
305                 310                 315                 320 cct ttc ctc att gac aag aga tgg aga caa acg gtc ttt cat                1062
Pro Phe Leu Ile Asp Lys Arg Trp Arg Gln Thr Val Phe His
                325                 330 tagtctattt gtgttgggtt ctttttttt taaatgaaaa gtatagtatg tggcactttt       1122
taaagaacaa aggaaatagt tttgtatgag tactttaatt gtgactctta ggatctttca      1182
ggtaaatgat gctcttgcac tagtgaaatt gtctaaagaa actaaagggc agtcatgccc      1242
tgtttgcagt aattttctt tttatcattt tgtttgtcct ggctaaactt ggagtttgag       1302
tatagtaaat tatgatcctt aaatatttga gagtcaggat gaagcagacc tgctgtagac      1362
ttttcagatg aaattgttca ttctcgtaac ctccatattt tcaggatttt tgaagctgtt     1422
gaccttttca tgttgattat tttaaattgt gtgaaatagt ataaaaatca ttggtgtaca      1482
ttatttgctt tgcctgagct cagatcaaaa tgtttgaaga aggaacttt attttttgcaa     1542 gttacgtaca gttttatgc ttgagatatt tcaacatgtt atgtatattg gaacttctac      1602
agcttgatgc ctcctgcttt tatagcagtt tatggggagc acttgaaaga gcgtgtgtac      1662
atgtattttt tttctaggca aacattgaat gcaaacgtgt attttttaa tataaatata      1722 taactgtcct tttcatccca tgttgccgct aagtgatatt tcatatgtgt ggttatactc     1782
ataataatgg gccttgtaag cctttcacc attcatgaat aataataaat atgtactgct      1842
ggcatgta                                                                1850

<210> SEQ ID NO 25
<211> LENGTH: 334
<212> TYPE: PRT
<213> ORGANISM: Homo sapiens

<400> SEQUENCE: 25

Met Val Gly Arg Glu Lys Glu Leu Ser Ile His Phe Val Pro Gly Ser
1               5                   10                  15

Cys Arg Leu Val Glu Glu Val Asn Ile Pro Asn Arg Arg Val Leu
            20                  25                  30

Val Thr Gly Ala Thr Gly Leu Leu Gly Arg Ala Val His Lys Glu Phe
        35                  40                  45

Gln Gln Asn Asn Trp His Ala Val Gly Cys Gly Phe Arg Arg Ala Arg
    50                  55                  60

Pro Lys Phe Glu Gln Val Asn Leu Leu Asp Ser Asn Ala Val His His
65                  70                  75                  80

Ile Ile His Asp Phe Gln Pro His Val Ile Val His Cys Ala Ala Glu
                85                  90                  95

Arg Arg Pro Asp Val Val Glu Asn Gln Pro Asp Ala Ala Ser Gln Leu
            100                 105                 110

Asn Val Asp Ala Ser Gly Asn Leu Ala Lys Glu Ala Ala Val Gly
        115                 120                 125
```

-continued

```
Ala Phe Leu Ile Tyr Ile Ser Ser Asp Tyr Val Phe Asp Gly Thr Asn
        130                 135                 140

Pro Pro Tyr Arg Glu Glu Asp Ile Pro Ala Pro Leu Asn Leu Tyr Gly
145                 150                 155                 160

Lys Thr Lys Leu Asp Gly Glu Lys Ala Val Leu Glu Asn Asn Leu Gly
                165                 170                 175

Ala Ala Val Leu Arg Ile Pro Ile Leu Tyr Gly Glu Val Glu Lys Leu
                180                 185                 190

Glu Glu Ser Ala Val Thr Val Met Phe Asp Lys Val Gln Phe Ser Asn
            195                 200                 205

Lys Ser Ala Asn Met Asp His Trp Gln Gln Arg Phe Pro Thr His Val
        210                 215                 220

Lys Asp Val Ala Thr Val Cys Arg Gln Leu Ala Glu Lys Arg Met Leu
225                 230                 235                 240

Asp Pro Ser Ile Lys Gly Thr Phe His Trp Ser Gly Asn Glu Gln Met
                245                 250                 255

Thr Lys Tyr Glu Met Ala Cys Ala Ile Ala Asp Ala Phe Asn Ile Pro
                260                 265                 270

Ser Ser His Leu Arg Pro Ile Thr Asp Ser Pro Val Leu Gly Ala Gln
            275                 280                 285

Arg Pro Arg Asn Ala Gln Leu Asp Cys Ser Lys Leu Glu Thr Leu Gly
        290                 295                 300

Ile Gly Gln Arg Thr Pro Phe Arg Ile Gly Ile Lys Glu Ser Leu Trp
305                 310                 315                 320

Pro Phe Leu Ile Asp Lys Arg Trp Arg Gln Thr Val Phe His
                325                 330
```

<210> SEQ ID NO 26
<211> LENGTH: 38
<212> TYPE: DNA
<213> ORGANISM: Homo sapiens

<400> SEQUENCE: 26
ggccacgcgt cgactagtac ttttttttt tttttttt                    38

<210> SEQ ID NO 27
<211> LENGTH: 7
<212> TYPE: DNA
<213> ORGANISM: Homo sapiens
<220> FEATURE:
<221> NAME/KEY: misc_feature
<222> LOCATION: (1)..(7)
<223> OTHER INFORMATION: n = g or a or t or c

<400> SEQUENCE: 27 gnnatgg                                                      7